US009469679B2

United States Patent
Runeberg-Roos et al.

(10) Patent No.: US 9,469,679 B2
(45) Date of Patent: *Oct. 18, 2016

(54) NEURTURIN MOLECULES

(71) Applicant: NTF Therapeutics, Inc., Woodbury, MN (US)

(72) Inventors: Pia Runeberg-Roos, Esbo (FI); Maxim M. Bespalov, Segrate (IT); Richard Penn, Chicago, IL (US); Mart Saarma, Helsinki (FI)

(73) Assignee: NTF Therapeutics, Inc., Chicago, IL (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/469,358

(22) Filed: Aug. 26, 2014

(65) Prior Publication Data

US 2015/0202263 A1    Jul. 23, 2015

Related U.S. Application Data

(60) Continuation of application No. 13/846,281, filed on Mar. 18, 2013, now Pat. No. 9,127,083, which is a division of application No. 12/946,167, filed on Nov. 15, 2010, now Pat. No. 8,445,432, which is a continuation-in-part of application No. 12/914,038, filed on Oct. 28, 2010, now abandoned.

(60) Provisional application No. 61/256,352, filed on Oct. 30, 2009.

(51) Int. Cl.
| | |
|---|---|
| *C07K 14/18* | (2006.01) |
| *C07K 14/475* | (2006.01) |
| *C07K 14/48* | (2006.01) |
| *A61K 38/18* | (2006.01) |
| *A61K 48/00* | (2006.01) |

(52) U.S. Cl.
CPC ............ *C07K 14/48* (2013.01); *A61K 38/185* (2013.01); *A61K 48/00* (2013.01); *C07K 14/475* (2013.01); *C07K 14/4756* (2013.01); *C07K 2319/02* (2013.01)

(58) Field of Classification Search
None
See application file for complete search history.

(56) References Cited

U.S. PATENT DOCUMENTS

| | | | |
|---|---|---|---|
| 5,739,307 A | 4/1998 | Johnson, Jr. et al. | |
| 5,747,655 A | 5/1998 | Johnson, Jr. et al. | |
| 5,814,622 A | 9/1998 | de Nanteuil et al. | |
| 5,843,914 A | 12/1998 | Johnson, Jr. et al. | |
| 6,090,778 A | 7/2000 | Johnson, Jr. et al. | |
| 6,743,628 B1 | 6/2004 | Johnson, Jr. et al. | |
| 7,015,311 B1 | 3/2006 | Johnson, Jr. et al. | |
| 2008/0057516 A1 | 3/2008 | Saarm et al. | |
| 2011/0003741 A1 | 1/2011 | Austen et al. | |
| 2011/0277045 A1 | 11/2011 | Dohrmann et al. | |

FOREIGN PATENT DOCUMENTS

| | | |
|---|---|---|
| WO | 2005051415 A1 | 6/2005 |
| WO | 2008000447 A1 | 1/2008 |
| WO | 2009059755 A1 | 5/2009 |

OTHER PUBLICATIONS

Abstract Book, NGF2010 Neurotrophic Factors in Health and Disease, Jun. 10-13, 2010 Helsinki Findland.
Adler, et al., "Modulation of Neuropathic Pain by a Glial Derived Factor", Pin Med 10(7), 1229-36, 2009.
Adly, et al., "Modulation of Neuropathic Pain by a Glial Derived Factor", J. Am. Acad. Dermatol., 58(2), 238-250, 2008.
Alfano et al, The major determinant of the heparin binding of glial cell-line derived neurotrophic factor is near the N-terminus and is dispensable for receptor binding, Biochem. J. 404 131-140, 2007.
Ai et al, SULF1 and SULF2 regulate heparan sulfate-mediated GDNF signaling for esophageal innervation, Devel 134 3327-3338, 2007.
Airaksinen et al , GDNF family neurotrophic factor signaling: four masters one servant, Mol. Cell. Neurosci. 13 313-325, 1999.
Baloh et al, Functional mapping of receptor specificity domains of glial cell line derived neurotrophic factor (GDNF) family ligands and production of GFRalpha1 RET specific agonists, J. Biol. Chem. 275 (5) 3412-3420, 2000.
Bespalov and Saarma, GDNF family receptor complexes are emerging drug targets, Trends Pharm Sci. 28(2) 68-74, 2008.
Bespalov, Ph.D. Thesis, 2009.
Botchkareva et al, New Roles for glial cell line derived neurotrophic factor and neurturin, Am. J. Pathol. 156(3) D 1041-53, 2000.
Grodin et al, Intraputamental infusion of exogenous neurturin protein restores motor and dopaminergic function in the globus pallidus of MPTP-lesioned rhesus monkeys, Cell Transplanation 17 373-381, 2008.
Davies et al, Structual determinants of heparan sulphae modulation of GDNF signalling, Growth Factors 21 (3-4) D 109-19, 2003.
Delacoux et al , Unraveling the Amino acid sequence crucial for Heparin binding to collagen V, J. Biol. Chem 275 (38) 29377-29382, 2000.
Eigenbrot & Gerber, X-ray structure of glial cell-derived neurotrophic factor at 1.9 A resolution and implications for receptor binding, Nature (Structural Biol) 4(6) 434-438, 1997.
Eketjall et al, Distinct structural in GDNF mediate binding to GFRalpha1 and activation of the GFRalpha1-c-Ret D receptor complex, EMBO J. 18 5901, 1999.
Fernandez et al, Polymorphisms in the genes encoding the 4 RET ligands GDNF, NTN, ARTN, PSPN, and susceptibility to Hirschsprung disease, J. Ped. Surgery 43 2042-2047, 2008.

(Continued)

*Primary Examiner* — Satyanarayana R Gudibande
*Assistant Examiner* — Jia-Hai Lee
(74) *Attorney, Agent, or Firm* — Dennis A. Bennett

(57) ABSTRACT

Neurturin polypeptides which possess reduced heparin and heparan sulfate binding affinity but retain neurotrophic activity, nucleic acids which encode the neurturin variants and vectors and host cells which express the enhanced neurturin polypeptides. Use of the enhanced neurturin polypeptides, nucleic acids and host cells in the treatment or prevention of disease.

6 Claims, 11 Drawing Sheets

(56) References Cited

OTHER PUBLICATIONS

Fjord-Larsen et al, Efficient in vivo protection of nigral dopaminergic neurons by lentivirus gene transfer of a modified Neurturin construct, Exp. Neurol 195 49-60, 2005.
Hadaczek et al, Pharmacokinetics and bioavailability of glial cell line derived factor (GDNF) and neurturin (NTN) infused into the rat brain, Neuropharm 58 114-1121, 2010.
Hamilton, Heparin co infusion during convection-enhanced delivery (CED) increases the distribution of the glial derived neurotrophic factor (GDNF) ligand family in rat striatum and enhances the pharmacological activity of neurturin, Exp. Neural. 168 155-161, 2001.
Hileman et al, Glycosaminoglycan-protein interactions: definition of consensus sites in glycosaminoglycan binding proteins, BioEssays 20 156-167, 1998.
Hoane et al, Mammalian cell produced neurturin (NTN) is more potent then purified *E. coli* produced NTN, Exp. Neurol 162 189-193, 2000.
Igarahi et al, Expression of receptors for glial cell line derived neurotrophic factor (GDNF) and neurturin in the inner blood retinal barrier of rats, Cell. Struct Fun ct 25(4) 237-41, 2000.
Kato et al, Herpes simplex virus vector mediated delivery of neurturin rescues ericle dysfunction of cavernous nerve injury, Gene Therapy 16(1) 26-33, 2009.
Knowles, Structure and chemical inhibition of the RET tyrosine kinase domain, J. Biol. Chem. 281 33577-33587, 2006.
Laurikainen et al, Glial cell line derived neurotrophic factor is expressed in penis of adult rat and retrogradely transported in penile parasymathetic and sensory nerves, Cell. Tiss. Res. 302(3) 321-9, 2000.
Laurikainen et al, Neuturin is a neurotrophic factor for penile parasympathetic neurons in adult rat, J. Neurobiol. 43(2) 198-205, 2000.
Li et al, Study of the construction, expression, and biological activity of recombiant adenovirus of neurturin, Prep. Biochem. Biotech. 39 439-452, 2009.
Lindholm et al, Novel neurotrophic factor CDNF protects and rescues midbrain dopamine neurons in vivo, Nature 448 73-78, 2007.
May et al, GDNF transduced schwann cell grafts enhance regreration of erectile nerves, Eur. Ural. 54(5) 1179-87, 2008.
Mwangi et al, Glial cell line derived neurotrophic factor enhances neurogenin3 gene expression and beta cell proliferation in the developing mouse pancreas., Am. J. Physiol. Gastrointest. Liver Physiol. 299 (1) G283-92, 2010.
Mwangi et al, Glial cell line derived neurotropnic factor increases beta cell mass and improves glucose tolerance, Gastroent 134(3) 727-37, 2008.
Nishikiori et al, Glial cell derived cytokines attenuate the breakdown of vascular integrity in diabetic retinopathy, Diabetes 56(6) 1333-40, 2007.
Parkash et al, The structure of the Glial cell line derived neurotrophic factor-co receptor complex, J. Biol. Chem. 283 (50)35164-35172, 2008.
Paratcha et al, The neural cell adhesion molecule NCAM is an alternative signalling receptor for GDNF family ligands, Cell 113 867-879, 2003.
Pasha & Gupta, Various drug delivery approaches to the central nervous system, Expert Opinion 7(1) 113-135, 2010.
Paveliev et al, GDNF family ligands activate multiple events during axonal growth in mature sensory neurons, Mol. Cell. Neurosci. 25 453-459, 2004.
Piltonen et al, Heparin-binding determinants of GDNF reduce its tissue distribution but are beneficial for the protection of nigral dopaminergic neurons, Exp. Neurol. 219 499-506, 2009.
Rickard et al, The binding of human glial cell line-derived neurotrophic factor (GDNF) to heparin and heparan sulfate, Glycobiology 13 419-426, 2003.
Rider, Interaction between glial-cell-line derived neurotrophic factor (GDNF) and 2-)-sulphates heparin related glycosaminoglycans, Biochem. Soc. Trans. 31(2) 337-9, 2003.
Rider, Heparin/heparan suphate binding in the TGF-beta cytokine superfamily, Biochem. Soc. Trans. 34(3) 458-460, 2006.
Roberts et al, Disturbances of colonic motility in mouse models of Hirschsprung's disease, Am. J. Physiol. Gastrointest. Liver Physiol. 294(4) G996-G1008, 2008.
Rossi et al, Parasympathetic innervation and function of Endocrine pancreas requires the glial cell line derived factor family receptor alpha2, Diabetes 54(5) 1324-30, 2005.
Schober et al, GDNF applied to the MPTP lesioned nigrostriatal system requires TGF-beta for its neuroprotective action, Neurobiol Dis. 25 378-391, 2007.
Silvian et al, Artemin crystal structure reveals insignts into heparan sufate binding, Biochem. 45 6801-6812, 2006.
Stover et al, Expression of the GDNF family members and their receptors in the mature rat cochlea, Brain Res Mol Brain Res 76(1) 25-35, 2000.
Stover et al, Glial cell line derived neurotrophic factor (GDNF) and its receptor complex are expressed in the auditory nerve of the mature rat cochlea, Hear Res 155(1-2) 143-51, 2001.
Tanaka et al, Heparin faciltates glial cell line derived neurotrophic factor signal transduction, Neuroreport 13(15) D 1913-1916, 2002.
Taraviras, Signalling by the RET receptor tyrosine kinase and its role in the development of the mammalian enteric nervous system, Devel. 126(12) 2785-97, 1999.
Vastag, Crossing the barrier, Nature 466 916-918, 2010.
Virtanen et al, The first cysteine rich domain of the receptor GFR alpha1 stabilizes the binding of GDNF, Biochem. J. 387 817-824, 2005.
Ylikoski et al, Guinea pig auditory neurons are protected by glial cell line derived growth factor from degeneration after noise trauma, Hear Res. 124(1-2) 17-26, 1998.
Yu et al, GDNF deprived symathetic neurons die via a novel nonmitochondrial pathway, J. Cell Biol 163 987-997, 2003.
Wang et al. (2004) Identification of the key amino acids of glial cell line-derived neurotrophic factor family receptor alpha 1 involved in its biological function. J. Biol. Chem. 279(1):109-116.
International Search Report and Written Opinion, PCT Application No. PCT/US2010/054419, Jul. 1, 2011, 12 pgs.
Cardin and Weintraub, "Molecular Modeling of Protein-Glycoasminoglycan Interactions", Arteriosclerosis 9, 1989, pp. 21-32.

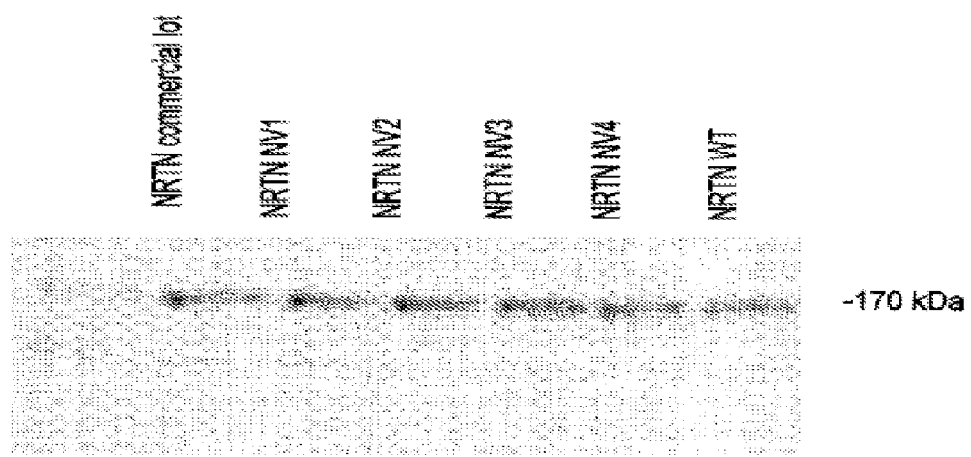

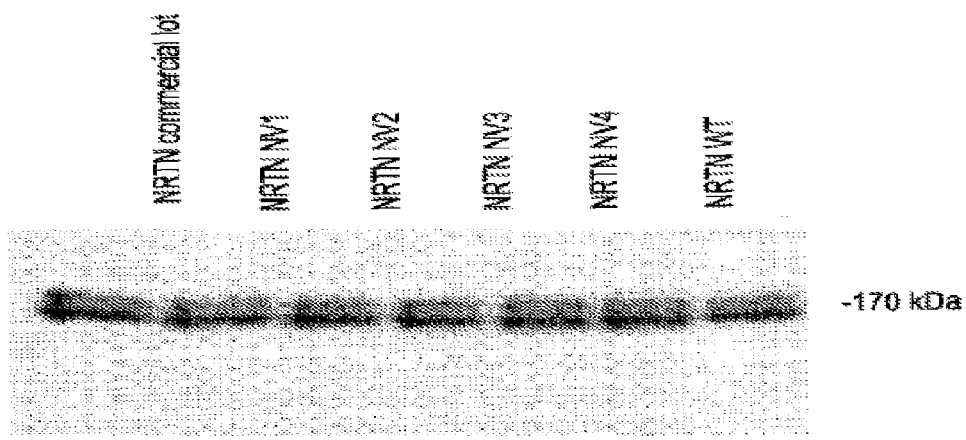

NEURTURIN MOLECULES

CROSS-REFERENCE TO RELATED APPLICATIONS

This application is a Continuation of U.S. application Ser. No. 13/846,281, filed Mar. 18, 2013, which is a Divisional of U.S. application Ser. No. 12/946,167, filed Nov. 15, 2010, now U.S. Pat. No. 8,445,432, which is a Continuation-In-Part of U.S. application Ser. No. 12/914,038, filed Oct. 28, 2010, abandoned, which is a non-provisional of U.S. application Ser. No. 61/256,352, filed Oct. 30, 2009. The contents of each of these previous applications is herein incorporated by reference in their entirety.

INCORPORATION OF SEQUENCE LISTING

This application contains a sequence listing submitted herewith electronically via EFS web containing the filed named "NTF0005-201C1-US_Seq_Listing_2014826" which is 21,149 bytes in size measured in MS Word, which was created on Aug. 26, 2014 and which is herein incorporated by reference in its entirety.

STATEMENT REGARDING FEDERALLY SPONSORED RESEARCH OR DEVELOPMENT

Not Applicable.

BACKGROUND OF THE INVENTION

Field of the Invention

The present invention relates to the development and use of enhanced neurturin polypeptides which possess reduced heparin and heparan sulfate binding affinity but retain neurotrophic activity; nucleic acids which encode the neurturin variants and vectors and host cells which express the enhanced neurturin polypeptides. Also encompassed within the invention is the use of the enhanced neurturin polypeptides, nucleic acids and host cells in the treatment of disease.

The glial cell line-derived neurotrophic factor (GDNF) family ligands (GFLs) are distant members of the TGF-β superfamily that are potent neurotrophic factors in vitro and are critical for the development of distinct neuronal populations in vivo (Airaksinen, M. S., et al., (1999) "GDNF family neurotrophic factor signaling: four masters, one servant?" *Mol. Cell. Neurosci.* 13, 313-325). There are four known members of this family with high sequence similarity; GDNF, neurturin (NRTN), artemin (ARTN) and persephin (PSPN). These factors all function through the activation of the transmembrane receptor tyrosine kinase rearranged during transfection (RET), which activates multiple signaling pathways. (Knowles, P P. (2006) "Structure and chemical inhibition of the RET tyrosine kinase domain", *J. Biol. Chem.* 281 33577-33587. Included in the receptor complex is a high affinity glycosylphosphatidylinositol (GPI)-anchored cell surface protein designated as GFRα (GDNF family receptor a), although there is one GFRα for each GFL, cross signaling occurs between the receptor complexes (Airaksinen et al, ibid). The GFLs also share an affinity for heparin except for PSPN which appears to have little or no affinity (Maxim M. Bespalov PhD thesis, 18.12. 2009, University of Helsinki). Heparin is a sulfated polysaccharide that is primarily confined to mast cells. However, the highly related heparan-sulfate (HS) is more ubiquitous, residing on cell surfaces and the extracellular matrix. It has been shown that the interaction between GDNF and heparin/HS demonstrates a particularly high dependence on the presence of 2-O-sulfates (Rickard et al., (2003) "The binding of human glial cell line-derived neurotrophic factor (GDNF) to heparin and heparan sulfate: importance of 2-O-sulfate groups and effects on its interaction with its receptor GFRα1". *Glycobiology* 13, 419-426).

Because of their neurotrophic qualities, the GFLs are emerging candidates for the treatment of diseases, and injuries of the central and peripheral nervous systems Central to the therapeutic utility of GFLs such as neurturin is the ability of these molecules to stimulate the survival and growth of a broad array of neurons, including for example, dopaminergic, sympathetic, parasympathetic, sensory neurons, and spinal motor neurons. (Bespalov, M M & Saarma, M. (2007) "GDNF family receptor complexes are emerging drug targets" Trends in Pharm. Sci. 28(2) 68-74). For instance both GDNF protein, and NRTN in a gene therapy vector, have been administered to patients in clinical trials for treatment of Parkinson's disease, and have been shown to stimulate dopamine turnover in animal models. (Hadaczek et al., (2010) Pharmacokinetics and bioactivity of glial cell line-derived factor (GDNF) and neurturin (NTN) infused into rat brain" Neuropharm. 58 1114-1121). Additionally diseases such as Alzheimer's, ALS, epilepsy, addiction, chronic pain and stroke may also benefit from treatment with neurturin based on the ability of neurturin to promote neuron survival and growth.

Furthermore there is increasing support for the concept that neurturin treatment may be useful for the treatment of diabetes (Rossi, et al., (2005) Diabetes 54(5) 1324-30; Mwangi et al., (2008) Gastroenterology 134(3) 727-37; Mwangi et al., (2010) Am. J. Physiol. Gastrointest Liver Physiol. 299(1) G283-92); erectile dysfunction (Laurikainen et al., (2000) Cell. Tissue. Res. 302(3) 321-9, Laurikainen et al., (2000) J. Neurobiol. 43(2) 198-205, May et al., (2008) Eur. Urol. 54(5) 1179-87; Kato et al., (2009) Gene Therapy 16(1) 26-33); hair loss (Botchkareva et al., (2000) Am. J. Pathol. 156(3) 1041-53, Adly et al., (2008) J. Am. Acad. Dermatol. 58(2) 238-50); hearing loss (Ylikoski et al., (1998) Hear Res. 124(1-2) 17-26, Stover et al., (2001) Hear Res. 155(1-2) 143-51, Stover et al., (2000) Brain Res Mol Brain Res. 76(1) 25-35; Hirschsprung's disease, (Taraviras et al., (1999) Development 126(12) 2785-97, Roberts et al., (2008) Am. J. Physiol. Gastrointest. Liver Physiol. 294(4) G996-G1008; Neuropathic pain, Adler et al., (2009) Pain. Med. 10(7) 1229-36; and retinopathy (Igarahi et al., (2000) Cell. Struct. Funct. 25(4) 237-41, Nishikiori et al., (2007) 56(5) 1333-40).

In a recent phase II clinical trial NRTN was administered to Parkinson's disease patients using a viral vector (CERE-120). CERE-120 was delivered by stereotactic injection to the putaminal region of the brain, providing stable, long-lasting expression of NRTN in a highly targeted fashion. However, the results of the double-blinded controlled trial indicated that there was no appreciable difference between patients treated with CERE-120 versus those in the control group. Both groups showed an approximate 7 point improvement in the protocol-defined primary endpoint (Unified Parkinson's Disease Rating Scale—motor off score at 12 months), relative to a mean at baseline of approximately 39 points. Both groups had a substantial number of patients who demonstrated a meaningful clinical improvement from baseline. CERE-120 appeared to be safe and well tolerated. In an 18 month follow-up of the CERE-120 trial, a modest clinical benefit was observed versus placebo.

The reasons for the trial failure are not fully understood. One hypothesis is that despite direct injection into affected areas of the brain, the high affinity of neurturin for heparan sulfate prevents adequate diffusion of the molecule to a broad enough region to be efficacious. In support of this hypothesis, the analysis of the distribution of neurturin in the brains of two treated patients, as well as animal studies suggest that neurturin fails to distribute evenly after infusion in the brain (Hadaczek et al., (2010) Pharmacokinetics and bioactivity of glial cell line-derived factor (GDNF) and neurturin (NTN) infused into rat brain" Neuropharm. 58 1114-1121; Ceregene Press Release May 27, 2009) again suggesting that wider biodistribution might be favorable.

Moreover, recent animal studies have included the co-infusion of heparin with neurturin into the brain in rhesus monkey models of Parkinson's disease (Grodin et al., "Intra-putamenal infusion of exogenous neurturin protein restores motor and dopaminergic function in the globus pallidus of MPTP-lesioned rhesus monkeys. *Cell Transplantation* 17: 373-381, 2008). In theory, the co-infused heparin would prevent the binding of the neurturin to the extracellular matrix while still allowing binding to the RET/GFRα receptor complex on target cells. Therefore, the co-injected neurturin might diffuse to a broader area.

Another approach to improving the efficacy and biodistribution of neurturin would be to alter the heparin binding affinity of the molecule without affecting its neurotrophic properties. However prior to the applicant's discovery, the location and identity of the actual amino acids involved in mediating heparin binding in neurturin were not known. Moreover it was not known whether the mutation of the heparin binding domain would disrupt the folding, and/or three dimensional structure of the protein, and result in a loss of the biological function, and more specifically the neurotrophic activity of the mutated molecules. Accordingly there remains the need for improved neurturin polypeptides that exhibit improved biodistribution while retaining high biological activity.

Despite the attractiveness of this approach, previous studies that have investigated the functional impact of the heparin binding characteristics of neurturin and other members of the GDNF family have provided mixed and contradictory results. (Rider, C C, (2006) Biochem. Soc. Trans. 34(3) 458-460; Rickard S M et al., (2003) Glycobiology 13(6) 419-26, Davies J A et al., (2003) Growth Factors 21(3-4) 109-19, Rider C C, (2003) Biochem. Soc. Trans. 31(2) 337-9, Tanaka M et al., (2002) Neuroreport 13(15) 1913-1916, Hamilton J F et al (2001) Exp. Neurol. 168(1) 155-61, Ai X et al., (2007) Development 134(18) 3327-38).

For example, although previous studies have shown that the motif "BBXB" or "BBBXXB", where "B" is a basic amino acid and "X" is any amino acid, is important for heparin binding, others have shown that proteins that do not contain this motif can also bind heparin and HS (Delacoux et al. "Unraveling the amino acid sequence crucial for heparin binding to collagen V." *J. Biol. Chem.* 2000 275 (38):29377-82). Additionally the lack of a detailed 3 dimensional structure of neurturin prevents a detailed analysis of whether any of the corresponding positively charged residues in neurturin are actually surface exposed and orientated in the mature protein such that their side chains are correctly aligned to interact with heparin.

Moreover studies with other GFL members have suggested that heparin binding may originate primarily in the N-terminal region of this protein family, or be distributed over several regions. (Alfano et al. ("The major determinant of the heparin binding of glial cell-line derived neurotrophic factor is near the N-terminus and is dispensable for receptor binding" Biochem. J. 404: 131-140, 2007); Silvian et al., ("Artemin crystal structure reveals insights into heparan sulfate binding" *Biochemistry* 45:6801-6812, 2006)).

Silvian et al. explored the heparin binding characteristics of ARTN, and showed that a series of arginine residues in a pre-alpha-helical region were shown to contact sulfate atoms in the crystal structure. They found that the amino terminal region of ARTN (amino acids 1-9), which was disordered in the crystal, was responsible for some HS binding activity. In addition, they mutagenized the three arginines (Arg48, Arg49 and Arg51) in the pre-alpha-helical region of ARTN by substituting these with glutamic acid residues. Incorporation of glutamic acids, reduced the affinity for heparin molecules suggesting that this pre-helical region may play a role in heparan sulfate interaction. However, this pre-helical region of ARTN is not well conserved in neurturin suggesting that the function of this region in neurturin may not be preserved.

In studies reported by Alfano et al., deletion of the N-terminal region of GDNF resulted in a marked reduction in heparin binding. Additionally Alfano et al. conducted alanine scanning mutagenesis on pairs of positively charged amino acids (K81A/K84A and R88A/R90A) in a region in GDNF containing several basic amino acids that reside on one face of an alpha-helical region of the mature GDNF protein. Alfano et al., found that both sets of two amino acid changes, either individually or combined, failed to significantly reduce the binding affinity of GDNF to heparin.

Although GDNF, ARTN and NRTN, are homologous, and comprise a generally similar structure, both the N-terminal regions of the mature proteins, and the regions around the theoretical heparin binding sequences are not well conserved. Accordingly precise predictions as to the role of these protein domains in NRTN, cannot be accurately inferred from studies from either GDNF or ARTN.

The present invention is based in part on the discovery of the amino acids in neurturin, comprising amino acids 51 to 63 (numbered as in mature human neurturin), which play a significant role in mediating the interaction of neurturin with heparin. Moreover, the present applicants have surprisingly discovered that the mutation of amino acids in this region leads to enhanced neurturin polypeptides that exhibit both a reduced affinity for heparin and yet retain neurotrophic activity, and specifically the ability to interact with GFRα1 or GFRα2, to induce the phosphorylation of RET and to induce cellular effects. Accordingly the present invention provides new neurturin polypeptides with improved biological activity, polynucleotides encoding such polypeptides, and cells expressing such polypeptides and methods for their use in the treatment and prevention of disease.

SUMMARY OF THE INVENTION

The invention is based, in part, on the discovery of neurturin molecules that have reduced heparin, heparan sulfate and heparan sulfated proteoglycan binding ability but retain the ability to induce phosphorylation of the RET protein upon binding of the receptor complex. Accordingly, in one embodiment, the invention comprises purified neurturin polypeptides comprising neurturin variants which possess the ability to induce phosphorylation of RET and possess reduced heparin binding activity. In another embodiment, the purified neurturin polypeptide variants comprise one or more substitutions at amino acids 51, 52, 54, 55, 56, 57, 58, 60, 61, 62 or 63. In another embodiment, the purified polypeptides comprising neurturin variants comprise SEQ. ID. NO. 1, 2, 3 and 4.

In another embodiment, the invention includes a neurturin polypeptide, wherein the neurturin polypeptide differs from mature wild type neurturin (SEQ. ID. NO. 5) by at least one mutation of a positively charged amino acid in a region comprising amino acids 51 to 63 of the mature wild type neurturin, and wherein the neurturin polypeptide has a decreased affinity to heparin compared to the mature wild type neurturin.

In one aspect, the neurturin polypeptide has the ability to induce the phosphorylation of RET when added to fibroblasts at a concentration of 100 ng/ml for 10 minutes at 37 C, wherein the fibroblasts express RET and either GFRalpha1 or GFRalpha2.

In one aspect, the neurturin polypeptide can be eluted from a heparin affinity column at a NaCl concentration of less than 1 M NaCl at pH 7.2.

In one aspect, the neurturin polypeptide has at least one mutation of at a position selected from the group consisting of R52, R54, R56, R58, R61, and R63.

In one aspect, the neurturin polypeptide has at least one mutation of at a position selected from the group consisting of R51, R54, Q55, R56, R57, R58, R60, R61 and E62. In one aspect, the mutation introduces at least one neutral, zwitterionic or negatively charged aliphatic amino acid. In another aspect, the mutation introduces at least one amino acid independently selected from the group consisting of glycine, alanine, leucine, valine, serine, and glutamine.

In one aspect, the neurturin polypeptide comprises mutations R52A, R56A and R58A. In one aspect, the neurturin polypeptide the polypeptide comprises mutations R54A, R61A and R63A. In one aspect, the neurturin polypeptide comprises mutations R52A, R54A, R56A, R58A and R61A. In one aspect, the neurturin polypeptide comprises mutations R51A, R54Q, Q55G, R56Q, R57G, R58A, R60V, R61G and E62S. In one aspect, the neurturin polypeptide comprises a replacement of amino acids 51 to 62 by the sequence ARLQGQGALVGS.

In another aspect of any of these neurturin polypeptides, the polypeptide is an enhanced neurturin polypeptide. In another aspect of any of these neurturin polypeptides, the polypeptide is an enhanced human neurturin polypeptide.

In another aspect of any of these neurturin polypeptides, the neurturin polypeptide is substantially homologous, or substantially similar to (SEQ. ID. NO. 5), over the amino acid sequence of the mature wild type neurturin, except for the 13 amino acids encompassed by residues 51 to 63 of mature human neurturin.

In one aspect, the neurturin polypeptide comprises SEQ ID. No 1. In one aspect the neurturin polypeptide comprises SEQ ID. No 2. In one aspect, the neurturin polypeptide comprises SEQ ID. No 3. In one aspect, the neurturin polypeptide comprises SEQ ID. No 4.

In another aspect of any of these neurturin polypeptides, the neurturin polypeptide is a fusion protein with another protein.

In another embodiment, the invention includes a method of treating cellular degeneration or insufficiency comprising administering to a patient in need of such treatment a therapeutically effective amount of any of the preceding neurturin polypeptides.

In one aspect, the patient has a disease or disorder selected from the group consisting of peripheral neuropathy, amyotrophic lateral sclerosis, Alzheimer's disease, Parkinson's disease, Huntington's disease, ischemic stroke, acute brain injury, acute spinal cord injury, neuropathic pain, diabetes, erectile dysfunction, hair loss, Hirschsprung's disease nervous systems tumors, multiple sclerosis, hearing loss, retinopathy and infection.

In one aspect, the cellular degeneration or insufficiency is comprised of hematopoietic cell degeneration or insufficiency selected from the group consisting of eosinopenia, basopenia, lymphopenia, monocytopenia, neutropenia, anemias, thrombocytopenia, and stem-cell insufficiencies.

In one aspect of any of these methods, the neurturin polypeptide is administered by systemic administration. In another aspect, the neurturin polypeptide is administered by intrathecal administration. In another aspect, the neurturin polypeptide is administered by intranasal administration. In another aspect, the neurturin polypeptide is administered by intraparenchymal administration. In another aspect, the neurturin polypeptide is administered by a sustained composition or device.

In another embodiment, the invention includes a pharmaceutical composition comprising any of the preceding neurturin peptides and a pharmaceutically acceptable carrier.

In another embodiment the invention includes an isolated polynucleotide encoding a neurturin polypeptide, wherein the neurturin polypeptide differs from mature wild type neurturin (SEQ. ID. NO. 5) by at least one mutation of a positively charged amino acid in a region comprising amino acids 51 to 63 of the mature wild type neurturin, and wherein the neurturin polypeptide has a decreased affinity to heparin compared to the mature wild type neurturin.

In one aspect, the polynucleotide encodes a neurturin polypeptide wherein the neurturin polypeptide has the ability to induce the phosphorylation of RET when added to fibroblasts at a concentration of 100 ng/ml for 10 minutes at 37 C, wherein the fibroblasts express RET and either GFRalpha1 or GFRalpha2.

In one aspect, the polynucleotide encodes a neurturin polypeptide wherein the neurturin polypeptide can be eluted from a heparin affinity column at a NaCl concentration of less than 1 M NaCl at pH 7.2.

In one aspect, the polynucleotide encodes a neurturin polypeptide wherein the polypeptide has at least one mutation of at a position selected from the group consisting of R52, R54, R56, R58, R61, and R63. In one aspect, the polynucleotide encodes a neurturin polypeptide wherein the neurturin polypeptide has at least one mutation of at a position selected from the group consisting of R51, R54, Q55, R56, R57, R58, R60, R61 and E62. In one aspect, the polynucleotide encodes a neurturin polypeptide wherein the mutation introduces at least one neutral, zwitterionic or negatively charged aliphatic amino acid. In one aspect, the polynucleotide encodes a neurturin polypeptide wherein the mutation introduces at least one amino acid independently selected from the group consisting of glycine, alanine, leucine, valine, serine, and glutamine.

In one aspect, the polynucleotide encodes a neurturin polypeptide wherein the polypeptide comprises mutations R52A, R56A and R58A. In one aspect the polynucleotide encodes a neurturin polypeptide wherein the neurturin polypeptide comprises mutations R54A, R61A and R63A. In one aspect the polynucleotide encodes a neurturin polypeptide wherein the neurturin polypeptide comprises mutations R52A, R54A, R56A, R58A and R61A. In one aspect the polynucleotide encodes a neurturin polypeptide wherein the neurturin polypeptide comprises mutations R51A, R54Q, Q55G, R56Q, R57G, R58A, R60V, R61G and E62S. In one aspect, the polynucleotide encodes a neurturin polypeptide wherein the polypeptide comprises a replacement of amino acids 51 to 62 by the sequence ARLQGQGALVGS.

In another aspect of any of the claimed polynucleotides, the polynucleotide encodes a neurturin polypeptide wherein the neurturin polypeptide is substantially homologous, or substantially similar to (SEQ. ID. NO. 5), over the amino acid sequence of the mature wild type neurturin, except for the 13 amino acids encompassed by residues 51 to 63 of mature human neurturin.

In one aspect the polynucleotide comprises SEQ ID. No 6. In one aspect the polynucleotide comprises SEQ ID. No 7. In one aspect the polynucleotide comprises SEQ ID. No 8. In one aspect the polynucleotide comprises SEQ ID. No 9.

In another embodiment, the invention includes a recombinant vector comprising the preceding polynucleotides. In one aspect, the recombinant vector further comprises expression control sequences operably linked to the polynucleotides. In one aspect, the recombinant vector is a viral vector.

In another embodiment, the invention includes a method of treating cellular degeneration or insufficiency comprising administering to a patient in need of such treatment a therapeutically effective amount of any of the preceding recombinant vectors.

In one aspect of this method, the patient has a disease or disorder selected from the group consisting of peripheral neuropathy, amyotrophic lateral sclerosis, Alzheimer's disease, Parkinson's disease, Huntington's disease, ischemic stroke, acute brain injury, acute spinal cord injury, neuropathic pain, diabetes, erectile dysfunction, hair loss, Hirschsprung's disease, nervous systems tumors, multiple sclerosis, hearing loss, retinopathy and infection.

In another aspect of this method, the cellular degeneration or insufficiency is comprised of hematopoietic cell degeneration or insufficiency selected from the group consisting of eosinopenia, basopenia, lymphopenia, monocytopenia, neutropenia, anemias, thrombocytopenia, and stem-cell insufficiencies.

In one aspect, the recombinant vector is administered by systemic administration. In one aspect, the recombinant vector is administered by intrathecal administration. In one aspect, the recombinant vector is administered by intranasal administration. In one aspect, the recombinant vector is administered by intraparenchymal administration. In one aspect, the recombinant vector is administered by a sustained composition or device.

In another embodiment the invention includes a pharmaceutical composition comprising any of the preceding recombinant vectors and a pharmaceutically acceptable carrier.

In another embodiment, the invention includes a host cell comprising the polynucleotide of any of the embodiments described herein. In one aspect, the host has been transformed or transfected with any of the preceding recombinant vectors. In one aspect, the host cell secretes any of the preceding neurturin polypeptides.

In another embodiment, the invention includes a method of treating cellular degeneration or insufficiency comprising administering to a patient in need of such treatment a therapeutically effective amount of any of the preceding host cells.

In one aspect, the patient has a disease or disorder selected from the group consisting of peripheral neuropathy, amyotrophic lateral sclerosis, Alzheimer's disease, Parkinson's disease, Huntington's disease, ischemic stroke, acute brain injury, acute spinal cord injury, neuropathic pain, diabetes, erectile dysfunction, hair loss, Hirschsprung's disease nervous systems tumors, multiple sclerosis, hearing loss, retinopathy and infection.

In one aspect, the cellular degeneration or insufficiency is comprised of hematopoietic cell degeneration or insufficiency selected from the group consisting of eosinopenia, basopenia, lymphopenia, monocytopenia, neutropenia, anemias, thrombocytopenia, and stem-cell insufficiencies.

In one aspect, the host cell is administered by systemic administration. In one aspect the host cell is administered by intrathecal administration. In one aspect, the host cell is administered by intranasal administration. In one aspect, the host cell is administered by intraparenchymal administration. In one aspect, the host cell is administered by a sustained composition or device.

In another embodiment, the invention includes a pharmaceutical composition comprising any of the preceding host cells and a pharmaceutically acceptable carrier. In another embodiment, the invention includes a pharmaceutical delivery system comprising an intrathecal pump and any of the preceding polypeptides.

Figure 1:
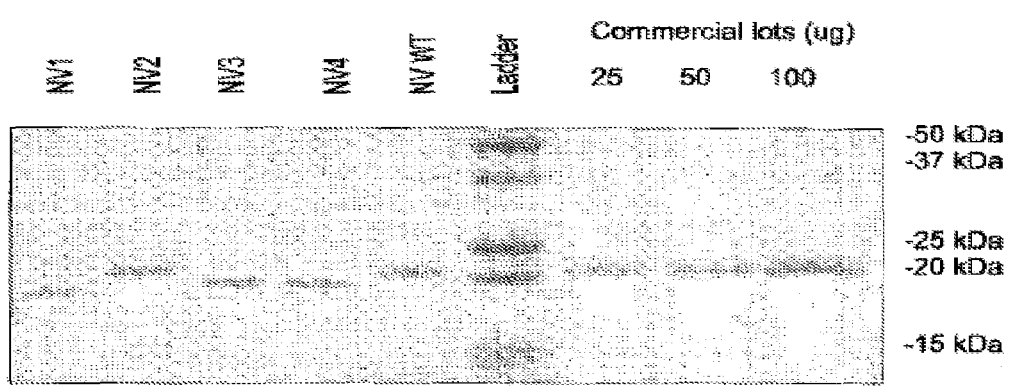
FIG. 1. Samples of purified enhanced neurturin variants, as well as a commercially available batch of neurturin were analyzed using 15% SDS-PAGE, under non reducing conditions, and visualized via Coomassie staining.
Figure 2A:
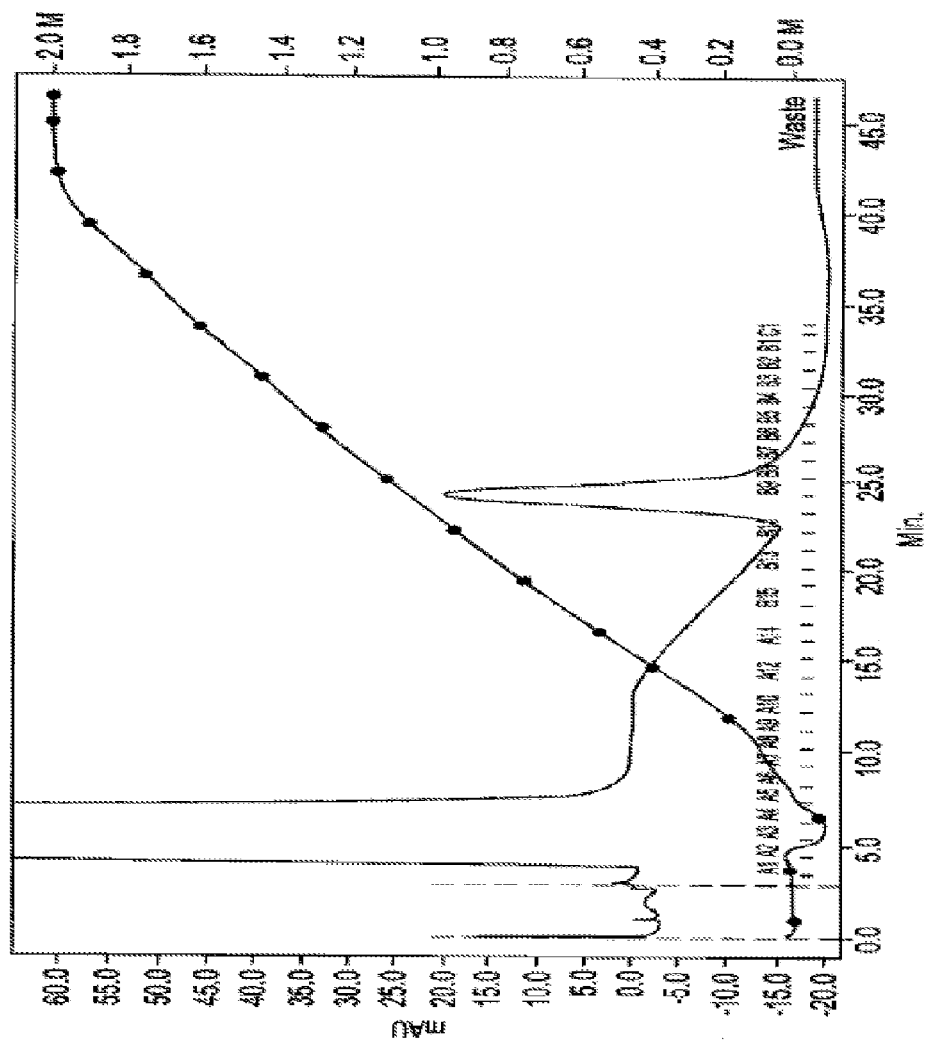
FIG. 2A shows the elution profile of a commercial preparation of neurturin.
Figure 2B:
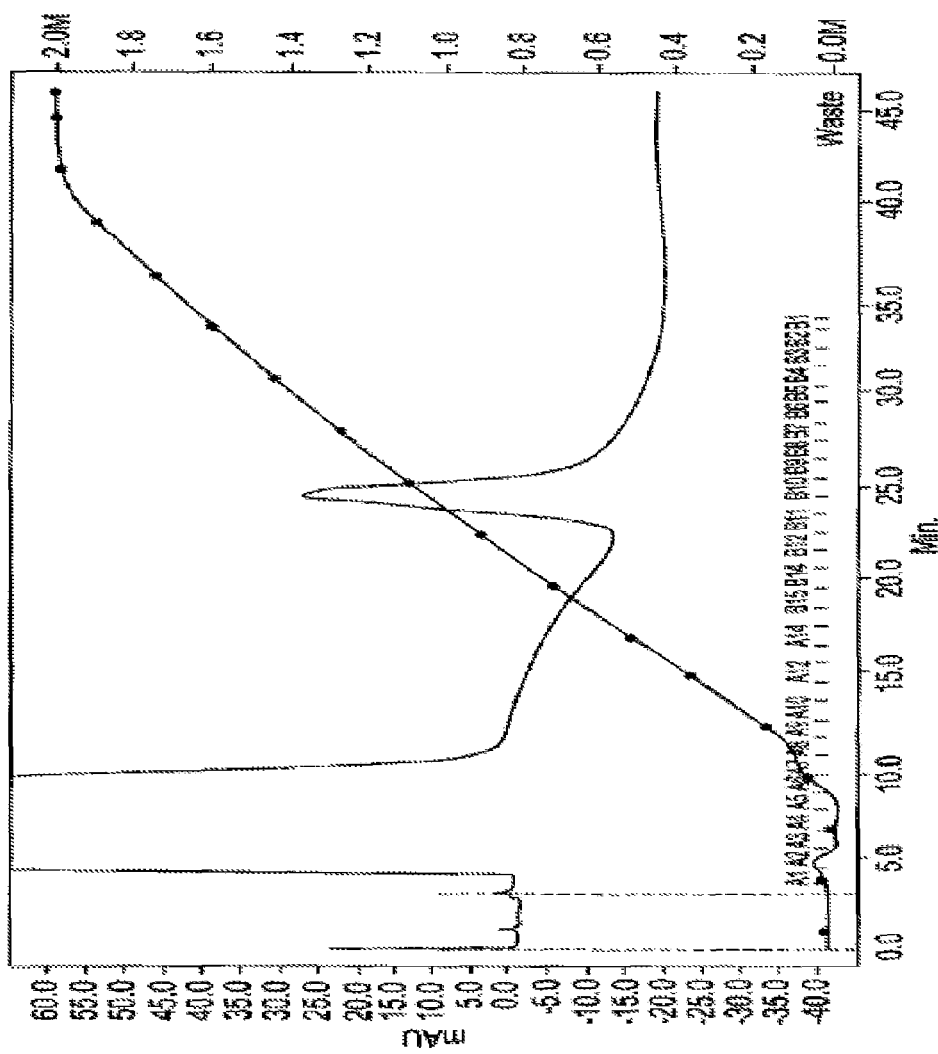
FIG. 2B shows the elution profile of a wild type preparation of neurturin made using the same method as for the neurturin variants.
Figure 2C:
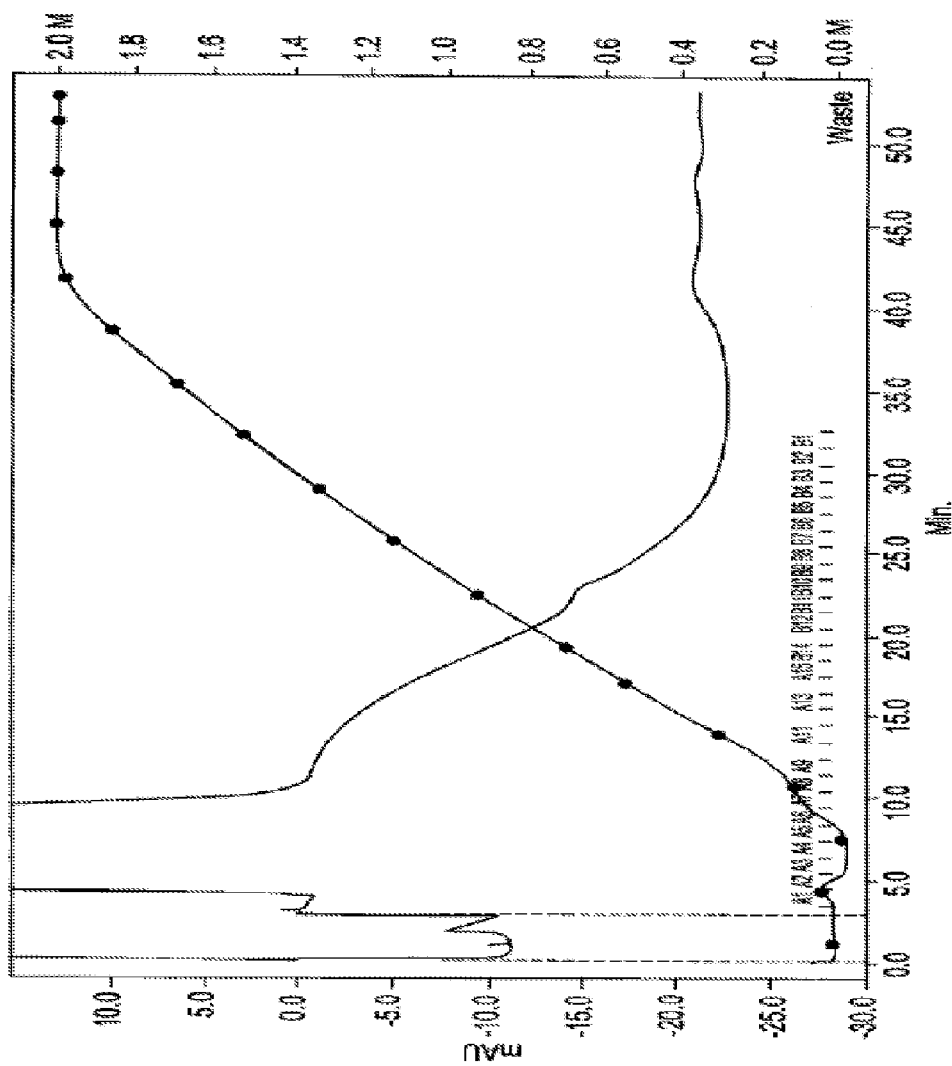
FIG. 2C shows the elution profile of N1.
Figure 2D:
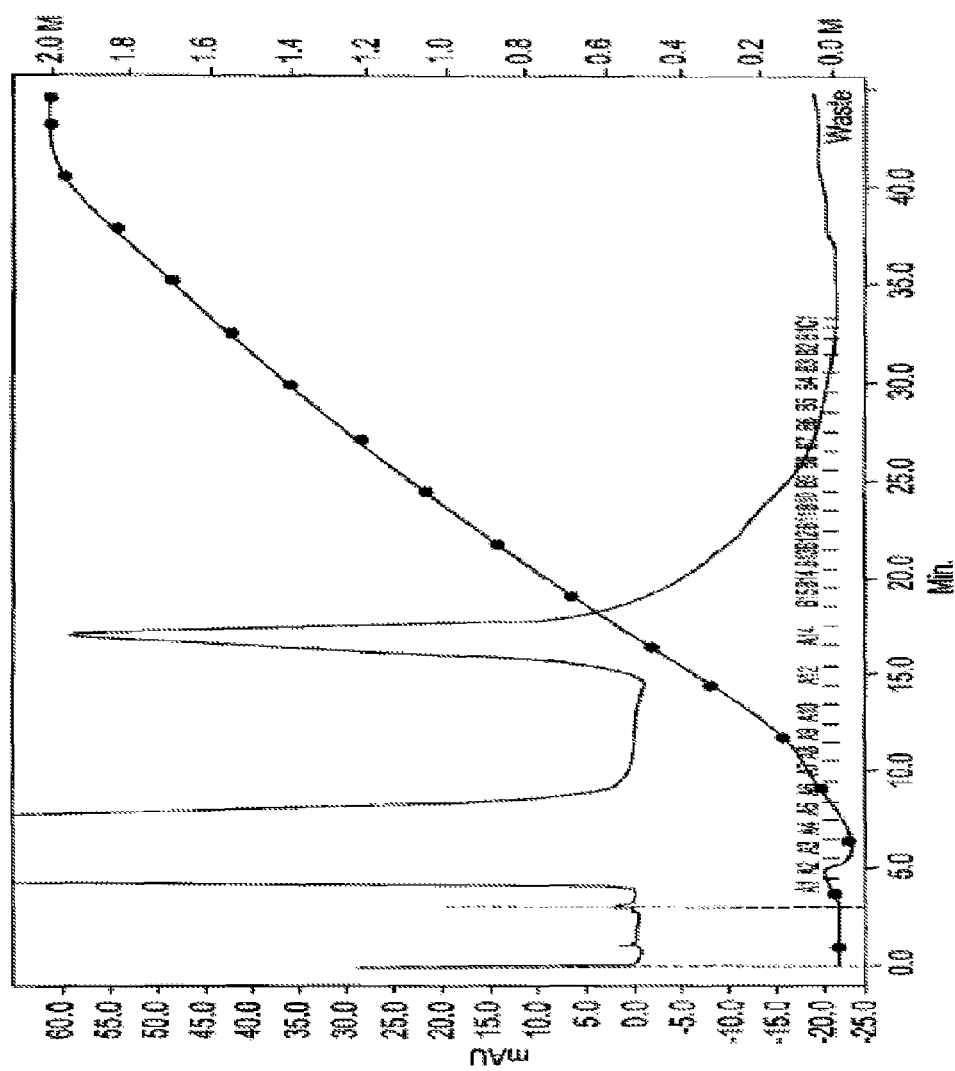
FIG. 2D shows the elution profile of N2.
Figure 2E:
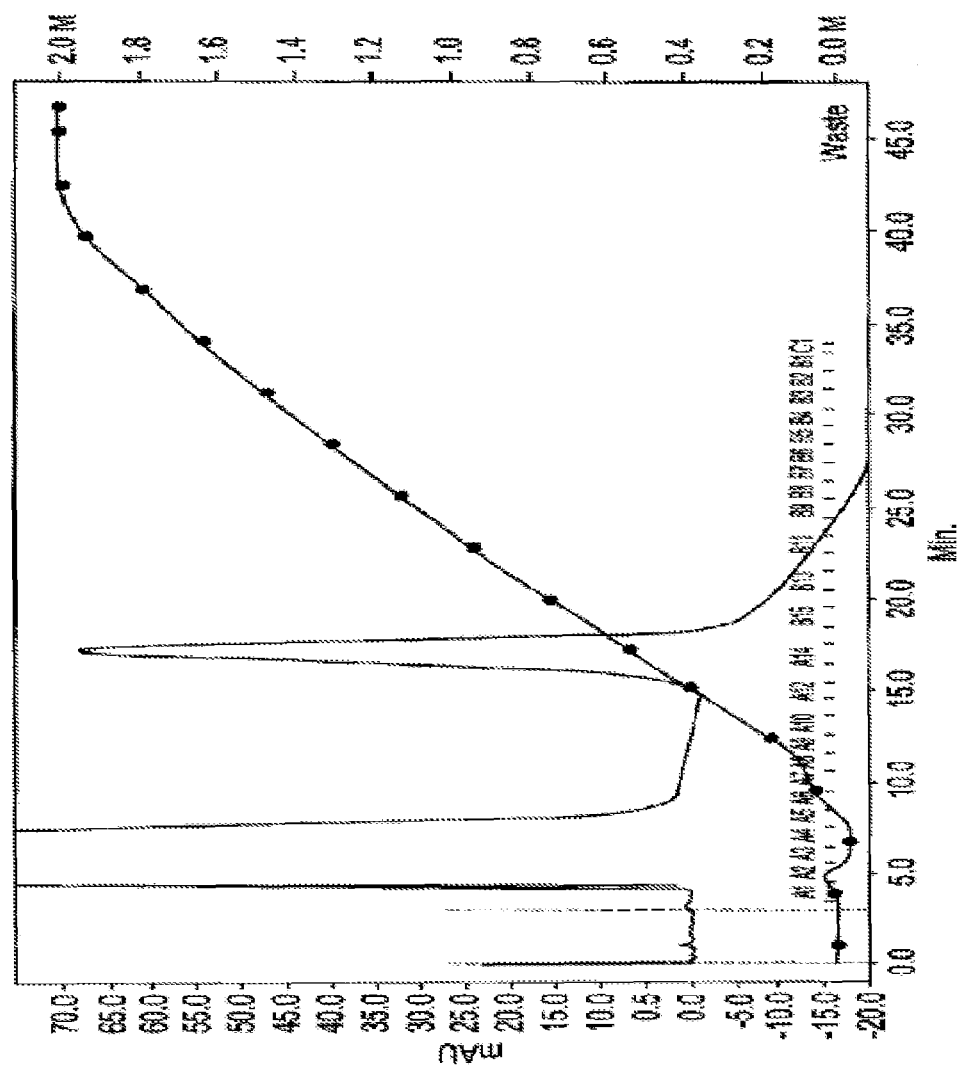
FIG. 2E shows the elution profile of N3.
Figure 2F:
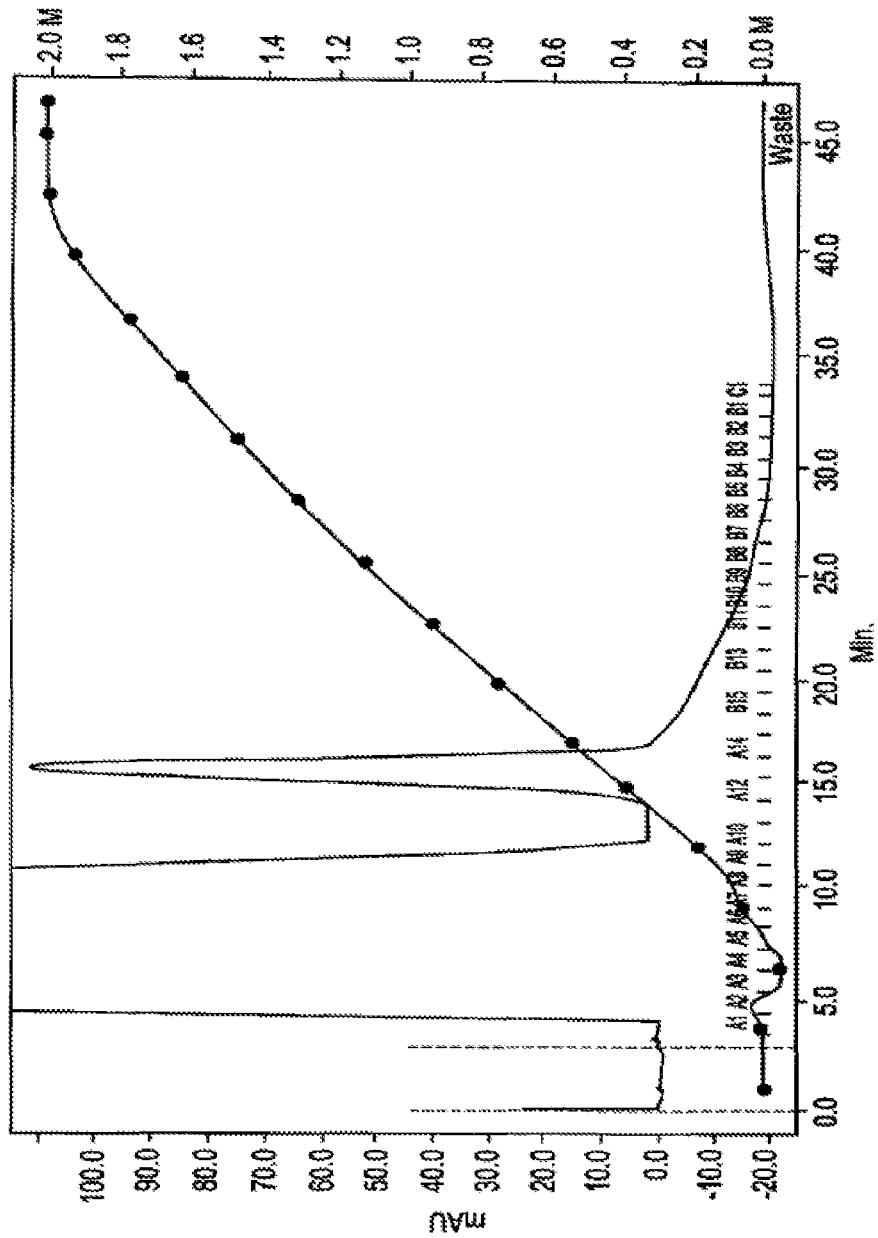
FIG. 2F shows the elution profile of N4.

FIG. 4A shows a western blot analysis of a RET-phosphorylation assay. Cells that stably express RET were transiently transfected with GFRα1, and after stimulation with the indicated neurturin variants, the cells were lysed and RET was isolated by immunoprecipitation. The samples were analysed by probing with anti-phosphotyrosine antibodies. FIG. 4B. To confirm an equal loading, the samples were subsequently re-probed with anti-RET antibodies.

DETAILED DESCRIPTION OF THE INVENTION

Definitions

In order that the present disclosure may be more readily understood, certain terms are first defined. Additional definitions are set forth throughout the detailed description. As used herein and in the appended claims, the singular forms "a," "an," and "the," include plural referents unless the context clearly indicates otherwise. Thus, for example, reference to "a molecule" includes one or more of such molecules, "a reagent" includes one or more of such different reagents, reference to "an antibody" includes one or more of such different antibodies, and reference to "the method" includes reference to equivalent steps and methods known to those of ordinary skill in the art that could be modified or substituted for the methods described herein.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges can independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

The term "about" or "approximately" means within an acceptable error range for the particular value as determined by one of ordinary skill in the art, which will depend in part on how the value is measured or determined, i.e., the limitations of the measurement system. For example, "about" can mean within 1 or 2 standard deviations, from the mean value. Alternatively, "about" can mean plus or minus a range of up to 20%, preferably up to 10%, more preferably up to 5%.

As used herein, the terms "cell," "cells," "cell line," "host cell," and "host cells," are used interchangeably and, encompass animal cells and include invertebrate, non-mammalian vertebrate and mammalian cells. All such designations include cell populations and progeny. Thus, the terms "transformants" and "transfectants" include the primary subject cell and cell lines derived therefrom without regard for the number of transfers. Exemplary non-mammalian vertebrate cells include, for example, avian cells, reptilian cells and amphibian cells. Exemplary invertebrate cells include, but are not limited to, insect cells such as, for example, caterpillar (*Spodoptera frugiperda*) cells, mosquito (*Aedes aegypti*) cells, fruitfly (*Drosophila melanogaster*) cells, Schneider cells, and Bombyx mori cells. See, e.g., Luckow et al., Bio/Technology 6:47-55 (1988). The cells may be differentiated, partially differentiated or undifferentiated, e.g. stem cells, including embryonic stem cells and pluripotent stem cells. Additionally tissue samples derived from organs or organ systems may be used according to the invention. Exemplary mammalian cells include, for example, cells derived from human, non-human primate, cat, dog, sheep, goat, cow, horse, pig, rabbit, rodents including mouse, hamster, rat and guinea pig and any derivatives and progenies thereof.

The terms "cell culture" or "tissue culture" refer to cells grown in suspension or grown adhered to a variety of surfaces or substrates in vessels such as roller bottles, tissue culture flasks, dishes, multi-well plates and the like.

The term "cell therapy" refers to a therapy comprising injecting, transplanting or otherwise placing cells into a mammalian body for therapy. In different aspects, the cells may be autologous, the cells may produce a protein, the cells may be regenerative, the cells may be modified, the cells may be genetically modified, the cells may be somatic cells, precursor cells or stem cells.

The phrase "conservative amino acid substitution" or "conservative mutation" refers to the replacement of one amino acid by another amino acid with a common property. A functional way to define common properties between individual amino acids is to analyze the normalized frequencies of amino acid changes between corresponding proteins of homologous organisms (Schulz, G. E. and R. H. Schirmer, Principles of Protein Structure, Springer-Verlag). According to such analyses, groups of amino acids can be defined where amino acids within a group exchange preferentially with each other, and therefore resemble each other most in their impact on the overall protein structure (Schulz, G. E. and R. H. Schirmer, Principles of Protein Structure, Springer-Verlag).

Examples of amino acid groups defined in this manner include: a "charged/polar group," consisting of Glu, Asp, Asn, Gln, Lys, Arg and His; an "aromatic, or cyclic group," consisting of Pro, Phe, Tyr and Trp; and an "aliphatic group" consisting of Gly, Ala, Val, Leu, Ile, Met, Ser, Thr and Cys.

Within each group, subgroups can also be identified, for example, the group of charged/polar amino acids can be sub-divided into the sub-groups consisting of the "positively-charged sub-group," consisting of Lys, Arg and His; the negatively-charged sub-group," consisting of Glu and Asp, and the "polar sub-group" consisting of Asn and Gln. The aromatic or cyclic group can be sub-divided into the sub-groups consisting of the "nitrogen ring sub-group," consisting of Pro, His and Trp; and the "phenyl sub-group" consisting of Phe and Tyr. The aliphatic group can be sub-divided into the sub-groups consisting of the "large aliphatic non-polar sub-group," consisting of Val, Leu and Ile; the "aliphatic slightly-polar sub-group," consisting of Met, Ser, Thr and Cys; and the "small-residue sub-group," consisting of Gly and Ala.

Examples of conservative mutations include substitutions of amino acids within the sub-groups above, for example, Lys for Arg and vice versa such that a positive charge can be maintained; Glu for Asp and vice versa such that a negative charge can be maintained; Ser for Thr such that a free —OH can be maintained; and Gln for Asn such that a free —$NH_2$ can be maintained.

As used herein, the term "decrease" or the related terms "decreased," "reduce" or "reduced" refers to a statistically significant decrease. For the avoidance of doubt, the terms generally refer to at least a 10% decrease in a given parameter, and can encompass at least a 20% decrease, 30% decrease, 40% decrease, 50% decrease, 60% decrease, 70% decrease, 80% decrease, 90% decrease, 95% decrease, 97% decrease, 99% or even a 100% decrease (i.e., the measured parameter is at zero).

The term "epitope tag" refers to any antigenic determinant, or any biological structure or sequence which is fused to the coding region of a protein of interest to enable the detection or purification of the protein of interest. Such fusion proteins can be identified and purified for example by using epitope tag specific antibodies. Representative examples of epitope tags include without limitation His tag (6-Histidine), HA tag (Hemagglutinin), V5-tag, c-Myc tag, GST tag, and a FLAG tag (DYKDDDDK).

The term "encapsulated" in the context of the expression "encapsulated cells" refers to cells in which the exterior of individual cells or groups of cells has been coated with an artificial membrane.

The term "expression" as used herein refers to transcription and/or translation of a nucleotide sequence within a host cell. The level of expression of a desired product in a host cell may be determined on the basis of either the amount of corresponding mRNA that is present in the cell, or the amount of the desired polypeptide encoded by the selected sequence. For example, mRNA transcribed from a selected sequence can be quantified by Northern blot hybridization, ribonuclease RNA protection, in situ hybridization to cellular RNA or by PCR. Proteins encoded by a selected sequence can be quantified by various methods including, but not limited to, e.g., ELISA, Western blotting, radioimmunoassays, immunoprecipitation, assaying for the biological activity of the protein, or by immunostaining of the protein followed by FACS analysis.

"Expression control sequences" are DNA regulatory sequences, such as promoters, enhancers, polyadenylation signals, terminators, internal ribosome entry sites (IRES) and the like, that provide for the expression of a coding sequence in a host cell. Exemplary expression control sequences are described in Goeddel; Gene Expression Technology: Methods in Enzymology 185, Academic Press, San Diego, Calif. (1990).

The term "heterologous DNA" refers to DNA which has been introduced into a cell, or nucleic acid sequence, that is derived from another source, or which is from the same source but is located in a different (i.e. non native) context.

The term "homology" describes a mathematically based comparison of sequence similarities which is used to identify genes or proteins with similar functions or motifs. The nucleic acid and protein sequences of the present invention can be used as a "query sequence" to perform a search against public databases to, for example, identify other family members, related sequences or homologs. Such searches can be performed using the NBLAST and XBLAST programs (version 2.0) of Altschul, et al. (1990) J. Mol. Biol. 215:403-10. BLAST nucleotide searches can be performed with the NBLAST program, score=100, wordlength=12 to obtain nucleotide sequences homologous to nucleic acid molecules of the invention. BLAST protein searches can be performed with the XBLAST program, score=50, wordlength=3 to obtain amino acid sequences homologous to protein molecules of the invention. To obtain gapped alignments for comparison purposes, Gapped BLAST can be utilized as described in Altschul et al., (1997) Nucleic Acids Res. 25(17):3389-3402. When utilizing BLAST and Gapped BLAST programs, the default parameters of the respective programs (e.g., XBLAST and BLAST) can be used.

The term "homologous" refers to the relationship between two proteins that possess a "common evolutionary origin", including proteins from superfamilies (e.g., the immunoglobulin superfamily) in the same species of animal, as well as homologous proteins from different species of animal (for example, myosin light chain polypeptide, etc.; see Reeck et al., Cell, 50:667, 1987). Such proteins (and their encoding nucleic acids) have sequence homology, as reflected by their sequence similarity, whether in terms of percent identity or by the presence of specific residues or motifs and conserved positions.

As used herein, the term "increase" or the related terms "increased", "enhance" or "enhanced" refers to a statistically significant increase. For the avoidance of doubt, the terms generally refer to at least a 10% increase in a given parameter, and can encompass at least a 20% increase, 30% increase, 40% increase, 50% increase, 60% increase, 70% increase, 80% increase, 90% increase, 95% increase, 97% increase, 99% or even a 100% increase over the control value.

The term "isolated," when used to describe a neurturin polypeptide, means protein that has been identified and separated and/or recovered from a component of its natural environment. Contaminant components of its natural environment are materials that would typically interfere with research, diagnostic or therapeutic uses for the protein, and may include enzymes, hormones, and other proteinaceous or non-proteinaceous solutes. In some embodiments, the protein will be purified to at least 95% homogeneity as assessed by SDS-PAGE under non-reducing or reducing conditions using Coomassie blue or, preferably, silver stain. Isolated protein includes protein in situ within recombinant cells, since at least one component of the protein of interest's natural environment will not be present. Ordinarily, however, isolated protein will be prepared by at least one purification step.

As used herein, "identity" means the percentage of identical nucleotide or amino acid residues at corresponding positions in two or more sequences when the sequences are aligned to maximize sequence matching, i.e., taking into account gaps and insertions. Identity can be readily calculated by known methods, including but not limited to those described in (Computational Molecular Biology, Lesk, A. M., ed., Oxford University Press, New York, 1988; Biocomputing: Informatics and Genome Projects, Smith, D. W., ed., Academic Press, New York, 1993; Computer Analysis of Sequence Data, Part I, Griffin, A. M., and Griffin, H. G., eds., Humana Press, New Jersey, 1994; Sequence Analysis in Molecular Biology, von Heinje, G., Academic Press, 1987; and Sequence Analysis Primer, Gribskov, M. and Devereux, J., eds., M Stockton Press, New York, 1991; and Carillo, H., and Lipman, D., SIAM J. Applied Math., 48: 1073 (1988). Methods to determine identity are designed to give the largest match between the sequences tested. Moreover, methods to determine identity are codified in publicly available computer programs. Computer program methods to determine identity between two sequences include, but are not limited to, the GCG program package (Devereux, J., et al., Nucleic Acids Research 12(1): 387 (1984)), BLASTP, BLASTN, and FASTA (Altschul, S. F. et al., J. Molec. Biol. 215: 403-410 (1990) and Altschul et al. Nuc. Acids Res. 25: 3389-3402 (1997)). The BLAST X program is publicly available from NCBI and other sources (BLAST Manual, Altschul, S., et al., NCBI NLM NIH Bethesda, Md. 20894; Altschul, S., et al., J. Mol. Biol. 215: 403-410 (1990). The well known Smith Waterman algorithm can also be used to determine identity.

The terms "operably linked" and "operatively linked," as used interchangeably herein, refer to the positioning of two or more nucleotide sequences or sequence elements in a manner which permits them to function in their intended manner. In some embodiments, a nucleic acid molecule according to the invention includes one or more DNA elements capable of opening chromatin and/or maintaining chromatin in an open state operably linked to a nucleotide sequence encoding a recombinant protein. In other embodiments, a nucleic acid molecule may additionally include one or more nucleotide sequences chosen from: (a) a nucleotide sequence capable of increasing translation; (b) a nucleotide sequence capable of increasing secretion of the recombinant protein outside a cell; and (c) a nucleotide sequence capable of increasing the mRNA stability, where such nucleotide sequences are operatively linked to a nucleotide sequence encoding a recombinant protein. Generally, but not necessarily, the nucleotide sequences that are operably linked are contiguous and, where necessary, in reading frame. However, although an operably linked DNA element capable of opening chromatin and/or maintaining chromatin in an open state is generally located upstream of a nucleotide sequence encoding a recombinant protein; it is not necessarily contiguous with it. Operable linking of various nucleotide sequences is accomplished by recombinant methods well known in the art, e.g. using PCR methodology, by ligation at suitable restrictions sites or by annealing. Synthetic oligonucleotide linkers or adaptors can be used in accord with conventional practice if suitable restriction sites are not present.

As used herein, the term "patient" in the context of the present invention is preferably a mammal. The mammal can be a human, non-human primate, mouse, rat, dog, cat, horse, or cow, but are not limited to these examples. Mammals other than humans can be advantageously used as patients that represent animal models of specific diseases and disorders. A patient can be male or female. A patient can be one who has been previously diagnosed or identified as having cellular degeneration or insufficiency, and optionally has already undergone, or is undergoing, a therapeutic intervention. Preferably the patient is human.

The terms "polynucleotide," "nucleotide sequence" and "nucleic acid" are used interchangeably herein, refer to a polymeric form of nucleotides of any length, either ribonucleotides or deoxyribonucleotides. These terms include a single-, double- or triple-stranded DNA, genomic DNA, cDNA, RNA, DNA-RNA hybrid, or a polymer comprising purine and pyrimidine bases, or other natural, chemically, biochemically modified, non-natural or derivatized nucleotide bases. The backbone of the polynucleotide can comprise sugars and phosphate groups (as may typically be found in RNA or DNA), or modified or substituted sugar or phosphate groups. In addition, a double-stranded polynucleotide can be obtained from the single stranded polynucleotide product of chemical synthesis either by synthesizing the complementary strand and annealing the strands under appropriate conditions, or by synthesizing the complementary strand de novo using a DNA polymerase with an appropriate primer. A nucleic acid molecule can take many different forms, e.g., a gene or gene fragment, one or more exons, one or more introns, mRNA, tRNA, rRNA, ribozymes, cDNA, recombinant polynucleotides, branched polynucleotides, plasmids, vectors, isolated DNA of any sequence, isolated RNA of any sequence, nucleic acid probes, and primers. A polynucleotide may comprise modified nucleotides, such as methylated nucleotides and nucleotide analogs, uracyl, other sugars and linking groups such as fluororibose and thioate, and nucleotide branches. As used herein, "DNA" or "nucleotide sequence" includes not only bases A, T, C, and G, but also includes any of their analogs or modified forms of these bases, such as methylated nucleotides, internucleotide modifications such as uncharged linkages and thioates, use of sugar analogs, and modified and/or alternative backbone structures, such as polyamides.

As used herein, the term "polypeptide" refers to any molecule comprising two or more amino acid residues joined to each other by peptide bonds or modified peptide bonds, i.e., peptide isosteres. "Polypeptide" refers to both short chains, commonly referred to as peptides, oligopeptides or oligomers, and to longer chains, generally referred to as proteins. Polypeptides may contain amino acids other than the 20 gene-encoded amino acids. "Polypeptides" include amino acid sequences modified either by natural processes, such as post-translational processing, or by chemical modification techniques that are well known in the art. Such modifications are well described in basic texts and in more detailed monographs, as well as in a voluminous research literature familiar to one of skill in the art. Modifications may occur anywhere in a polypeptide, including the peptide backbone, the amino acid side-chains and the amino or carboxyl termini. It will be appreciated that the same type of modification may be present to the same or varying degrees at several sites in a given polypeptide. Also, a given polypeptide may contain many types of modifications. Polypeptides may be branched as a result of ubiquitination, and they may be cyclic, with or without branching. Cyclic, branched and branched cyclic polypeptides may result from post-translation natural processes or may be made by synthetic methods. Modifications include for example, acetylation, acylation, ADP-ribosylation, amidation, biotinylation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent cross-links, formation of cystine, formation of pyroglutarnate, formylation, gamma-carboxylation, glycosylation, GP1 anchor formation, hydroxylation, iodination, methylation, myristoylation, palmitoylation, oxidation, proteolytic processing, phosphorylation, prenylation, racemization, selenoylation, sulfation, transfer-RNA mediated addition of amino acids to proteins such as arginylation, and ubiquitination (see, for instance, Proteins-Structure and Molecular Properties, 2nd Ed., T. E. Creighton, W.H. Freeman and Company, New York, 1993; Wold, F., Post-translational Protein Modifications: Perspectives and Prospects, 1-12, in Post-translational Covalent Modification of Proteins, B. C. Johnson, Ed., Academic Press, New York, 1983; Seifter et al, "Analysis for protein modifications and nonprotein cofactors", Meth Enzymol, 182, 626-646, 1990, and Rattan et al., "Protein Synthesis: Post-translational Modifications and Aging", Ann NY Acad Sci, 663, 48-62, 1992).

A "promoter" is a DNA regulatory region capable of binding RNA polymerase in a cell and initiating transcription of a downstream (3' direction) coding sequence. As used herein, the promoter sequence is bounded at its 3' terminus by the transcription initiation site and extends upstream (5' direction) to include the minimum number of bases or elements necessary to initiate transcription at levels detectable above background. A transcription initiation site (conveniently defined by mapping with nuclease S1) can be found within a promoter sequence, as well as protein binding domains (consensus sequences) responsible for the binding of RNA polymerase. Eukaryotic promoters can often, but not always, contain "TATA" boxes and "CAT" boxes. Prokaryotic promoters contain Shine-Dalgarno sequences in addition to the −10 and −35 consensus sequences. A large number of promoters, including constitutive, inducible and repressible promoters, from a variety of different sources are well known in the art. Representative sources include for example, viral, mammalian, insect, plant, yeast, and bacterial cell types, and suitable promoters from these sources are readily available, or can be made synthetically, based on sequences publicly available on line or, for example, from depositories such as the ATCC as well as other commercial or individual sources. Promoters can be unidirectional (i.e., initiate transcription in one direction) or bi-directional (i.e., initiate transcription in either a 3' or 5' direction). Non-limiting examples of promoters include, for example, the T7 bacterial expression system, pBAD (araA) bacterial expression system, the cytomegalovirus (CMV) promoter, the SV40 promoter, the RSV promoter, Inducible promoters include the Tet system, (U.S. Pat. Nos. 5,464,758 and 5,814,618), the Ecdysone inducible system (No et al., Proc. Natl. Acad. Sci. (1996) 93 (8): 3346-3351; the T-RE$_x$™ system (Invitrogen Carlsbad, Calif.), LacSwitch® (Stratagene, (San Diego, Calif.) and the Cre-ER$^T$ tamoxifen inducible recombinase system (Indra et al. Nuc. Acid. Res. (1999) 27 (22): 4324-4327; Nuc. Acid. Res. (2000) 28 (23): e99; U.S. Pat. No. 7,112,715; and Kramer & Fussenegger, Methods Mol. Biol. (2005) 308: 123-144) or any promoter known in the art suitable for expression in the desired cells.

The term "purified" as used herein refers to material that has been isolated under conditions that reduce or eliminate the presence of unrelated materials, i.e., contaminants, including native materials from which the material is obtained. For example, a purified protein is preferably substantially free of other proteins or nucleic acids with which it is associated in a cell. Methods for purification are well-known in the art. As used herein, the term "substantially free" is used operationally, in the context of analytical testing of the material. Preferably, purified material substantially free of contaminants is at least 50% pure; more preferably, at least 75% pure, and more preferably still at least 95% pure. Purity can be evaluated by chromatography, gel electrophoresis, immunoassay, composition analysis, biological assay, and other methods known in the art. The term "substantially pure" indicates the highest degree of purity, which can be achieved using conventional purification techniques known in the art.

The term "recombinant protein" or "recombinant polypeptide" refers to i) a protein encoded in all or part by heterologous DNA, or ii) a protein that is expressed from expression control sequences (such as a promoter, or enhancer) created in whole or part by the heterologous DNA which activates the expression of an endogenous gene.

The term "sequence similarity" refers to the degree of identity or correspondence between nucleic acid or amino acid sequences that may or may not share a common evolutionary origin (see Reeck et al., supra). However, in common usage and in the instant application, the term "homologous", when modified with an adverb such as "highly", may refer to sequence similarity and may or may not relate to a common evolutionary origin.

In specific embodiments, two nucleic acid sequences are "substantially homologous" or "substantially similar" when at least about 85%, and more preferably at least about 90% or at least about 95% of the nucleotides match over a defined length of the nucleic acid sequences, as determined by a sequence comparison algorithm known such as BLAST, FASTA, DNA Strider, CLUSTAL, etc. An example of such a sequence is an allelic or species variant of the specific genes of the present invention. Sequences that are substantially homologous may also be identified by hybridization, e.g., in a Southern hybridization experiment under, e.g., stringent conditions as defined for that particular system.

Similarly, in particular embodiments of the invention, two amino acid sequences are "substantially homologous" or "substantially similar" when greater than 90% of the amino acid residues are identical. Two sequences are functionally identical when greater than about 95% of the amino acid residues are similar. Preferably the similar or homologous polypeptide sequences are identified by alignment using, for example, the GCG (Genetics Computer Group, Version 7, Madison, Wis.) pileup program, or using any of the programs and algorithms described above. The program may use the local homology algorithm of Smith and Waterman with the default values: Gap creation penalty=-(1+1/k), k being the gap extension number, Average match=1, Average mismatch=-0.333.

As defined herein, the terms "sustained release", "extended release", or "depot formulation" refers to the release of a drug such as an enhanced neurturin polypeptide from the sustained release composition or sustained release device which occurs over a period which is longer than that period during which the neurturin polypeptide would be available following direct I.V. or S.C. administration of a single dose of enhanced neurturin polypeptide. In one aspect, sustained release will be a release that occurs over a period of at least about one to two weeks. In another aspect, sustained release will be a release that occurs over a period of at least about four months. The continuity of release and level of release can be affected by the type of sustained release device (e.g., programmable pump or osmotically-driven pump) or sustained release composition used (e.g., monomer ratios, molecular weight, block composition, and varying combinations of polymers), polypeptide loading, and/or selection of excipients to produce the desired effect, as more fully described herein.

The term "transformation" or "transfection" refers to the transfer of one or more nucleic acid molecules into a host cell or organism. Methods of introducing nucleic acid molecules into host cells include, for instance, calcium phosphate transfection, DEAE-dextran mediated transfection, microinjection, cationic lipid-mediated transfection, electroporation, scrape loading, ballistic introduction or infection with viruses or other infectious agents. "Transformed", "transduced", or "transgenic", in the context of a cell, refers to a host cell or organism into which a recombinant or heterologous nucleic acid molecule (e.g., one or more DNA constructs or RNA, or siRNA counterparts) has been introduced. The nucleic acid molecule can be stably expressed (i.e. maintained in a functional form in the cell for longer than about three months) or non-stably maintained in a functional form in the cell for less than three months i.e. is transiently expressed. For example, "transformed," "transformant," and "transgenic" cells have been through the transformation process and contain foreign nucleic acid. The term "untransformed" refers to cells that have not been through the transformation process.

The terms "treating" or "treatment" means to relieve, alleviate, delay, reduce, reverse, improve, manage, or prevent at least one symptom of a condition in a patient. The term "treating" may also mean to arrest, delay the onset (i.e., the period prior to clinical manifestation of a disease), and/or reduce the risk of developing or worsening a condition.

As used herein, the terms "therapeutically effective amount", "prophylactically effective amount", or "diagnostically effective amount" is the amount of the active agent, e.g. enhanced neurturin polypeptide, polynucleotide comprising a nucleotide sequence encoding such enhanced neurturin, or host cell expressing recombinant enhanced neurturin, needed to elicit the desired biological response following administration.

The term "variant" refers to a polynucleotide or polypeptide that differs from a reference polynucleotide or polypeptide, but retains the some essential properties thereof. A typical variant of a polypeptide differs in amino acid sequence from the reference polypeptide. Generally, alterations are limited so that the sequences of the reference polypeptide and the variant are similar overall and, in many regions, identical. A variant and reference polypeptide may differ in amino acid sequence by one or more substitutions, insertions or deletions in any combination. A substituted or inserted amino acid residue may or may not be one encoded by the genetic code.

The term, "wild type neurturin" or "pre-pro neurturin" refers to the gene encoding the amino acid sequence (SEQ. ID. NO. 26 in Table D3). The terms, "mature wild type neurturin," or "mature human neurturin" refers to the gene encoding the amino acid sequence (SEQ. ID NO. 5 in Table D2), which has been processed by removal of the secretion signal and pre-protein. The term "NRTN" refers to the gene encoding wild type neurturin.

The practice of the present invention will employ, unless otherwise indicated, conventional techniques of chemistry, molecular biology, microbiology, recombinant DNA and immunology, which are within the capabilities of a person of ordinary skill in the art. Such techniques are explained in the literature. See, for example, J. Sambrook, E. F. Fritsch, and T. Maniatis, 1989, Molecular Cloning: A Laboratory Manual, Second Edition, Books 1-3, Cold Spring Harbor Laboratory Press; Ausubel, F. M. et al. (1995 and periodic supplements; Current Protocols in Molecular Biology, ch. 9, 13, and 16, John Wiley & Sons, New York, N.Y.); B. Roe, J. Crabtree, and A. Kahn, 1996, DNA Isolation and Sequencing: Essential Techniques, John Wiley & Sons; J. M. Polak and James O'D. McGee, 1990, In Situ Hybridization: Principles and Practice; Oxford University Press; M. J. Gait (Editor), 1984, Oligonucleotide Synthesis: A Practical Approach, Irl Press; D. M. J. Lilley and J. E. Dahlberg, 1992, Methods of Enzymology: DNA Structure Part A: Synthesis and Physical Analysis of DNA Methods in Enzymology, Academic Press; Using Antibodies: A Laboratory Manual: Portable Protocol NO. I by Edward Harlow, David Lane, Ed Harlow (1999, Cold Spring Harbor Laboratory Press, ISBN 0-87969-544-7); Antibodies: A Laboratory Manual by Ed Harlow (Editor), David Lane (Editor) (1988, Cold Spring Harbor Laboratory Press, ISBN 0-87969-3,4-2), 1855. Handbook of Drug Screening, edited by Ramakrishna Seethala, Prabhavathi B. Fernandes (2001, New York, N.Y., Marcel Dekker, ISBN 0-8247-0562-9); and Lab Ref: A Handbook of Recipes, Reagents, and Other Reference Tools for Use at the Bench, Edited Jane Roskams and Linda Rodgers, 2002, Cold Spring Harbor Laboratory, ISBN 0-87969-630-3. Each of these general texts is herein incorporated by reference.

Unless defined otherwise, all technical and scientific terms used herein have the same meaning as commonly understood by one of ordinary skill in the art to which the invention belongs. Although any methods, compositions, reagents, cells, similar or equivalent to those described herein can be used in the practice or testing of the invention, the preferred methods and materials are described herein.

The publications discussed above are provided solely for their disclosure before the filing date of the present application. Nothing herein is to be construed as an admission that the invention is not entitled to antedate such disclosure by virtue of prior invention.

All publications and references, including but not limited to patents and patent applications, cited in this specification are herein incorporated by reference in their entirety as if each individual publication or reference were specifically and individually indicated to be incorporated by reference herein as being fully set forth. Any patent application to which this application claims priority is also incorporated by reference herein in its entirety in the manner described above for publications and references.

Overview

The invention is based, in part, on the discovery of enhanced neurturin molecules that have reduced heparin and heparan sulfate binding ability but surprisingly retain the ability to induce phosphorylation of the RET protein upon binding the receptor complex. In different embodiments, the invention comprises purified polypeptides, polynucleotides encoding the enhanced neurturin polypeptides, recombinant vectors containing the polynucleotides, and host expressing the enhanced neurturin polypeptides which possess the ability to induce phosphorylation of RET and possess decreased heparin binding affinity. Also included in the invention is the use of these various embodiments in the treatment of human diseases and disorders.

I. Neurturin Polypeptides

The terms "enhanced neurturin polypeptide", or "enhanced neurturin" or "enhanced NRTN" as used herein includes all naturally-occurring and synthetic forms of neurturin that differ from the corresponding mature wild type neurturin SEQ. ID. NO. 5 by at least one mutation of a positively charged amino acid in a region comprising amino acids 51 to 63 of the mature wild type neurturin, and exhibit a decreased affinity to heparin compared to the mature human neurturin.

In another aspect, the enhanced neurturin differs from the corresponding mature wild type neurturin SEQ. ID. NO. 5 by the mutation of at least two of the positively charged amino acids in a region comprising amino acids 51 to 63 of the mature wild type neurturin, and exhibit a decreased affinity to heparin compared to the mature human neurturin.

In another aspect, the enhanced neurturin differs from the corresponding mature wild type neurturin SEQ. ID. NO. 5 by the mutation of at least three of the positively charged amino acids in a region comprising amino acids 51 to 63 of the mature wild type neurturin, and exhibit a decreased affinity to heparin compared to the mature human neurturin.

In another aspect, the enhanced neurturin differs from the corresponding mature wild type neurturin SEQ. ID. NO. 5 by the mutation of at least five of the positively charged amino acids in a region comprising amino acids 51 to 63 of the mature wild type neurturin, and exhibit a decreased affinity to heparin compared to the mature human neurturin.

In one embodiment, the term "enhanced neurturin polypeptide" refers to a polypeptide which is at least 90% identical to mature wild type neurturin (SEQ. ID. NO. 5), over the amino acid sequence of the mature wild type neurturin, except for the 13 amino acids encompassed by residues 51 to 63 of mature human neurturin. In another aspect, an "enhanced human neurturin polypeptide" for use in any of the methods of the invention is at least 95% identical to (mature wild type neurturin) SEQ. ID. NO. 5, over the amino acid sequence of the mature wild type neurturin, except for the 13 amino acids encompassed by residues 51 to 63 of mature human neurturin.

In one embodiment, the enhanced neurturin polypeptides comprise one or more mutations at amino acids 51, 52, 54, 55, 56, 57, 58, 60, 61, 62 or 63 as compared to mature wild type neurturin, using the numbering for the 102 amino acid long mature wild type neurturin (SEQ. ID. NO. 5). In one aspect of the invention, the enhanced neurturin comprises 1 to 13 amino acid mutations within the region encompassed by residues 51 to 63 of mature human neurturin (SEQ. ID. NO. 5). In one aspect, the enhanced neurturin will comprise 1, 2, 3, 4, 5, 6, 7, 8, 9, 10, 11, 12, or 13 amino acid mutations within the region encompassed by residues 51 to 63 of mature human neurturin (SEQ. ID. NO. 5). In yet another aspect, the enhanced neurturin will comprise 3, 5, 7, 9 or 11 amino acid mutations within the region encompassed by residues 51 to 63 of mature human neurturin.

In one aspect of any of the enhanced neurturin polypeptides, the one or more mutations introduces in to the enhanced neurturin at least one neutral, zwitterionic or negatively charged aliphatic amino acid. In another aspect of any of the enhanced neurturin polypeptides, the one or more mutations introduces into the enhanced neurturin at least one amino acid independently selected from the group consisting of glycine, alanine, leucine, valine, serine, and glutamine.

In another aspect, the enhanced neurturin polypeptide comprises a replacement of amino acids 51 to 62 by the sequence ARLQGQGALVGS (SEQ. ID. NO. 25). In another aspect, the enhanced neurturin polypeptide comprises a sequence selected from SEQ. ID. NO. 22 to 25. (Table D1), wherein the enhanced neurturin polypeptide exhibits a decreased affinity to heparin compared to the mature wild type human neurturin.

TABLE D1

Amino acid sequences that provide for reduced affinity to heparin when inserted into mature wild type neurturin.

| SEQ. ID. NO. | Amino Acid Sequence |
|---|---|
| SEQ. ID. NO. 22 | RALRQARA |
| SEQ. ID. NO. 23 | RRLAQRRRLRAEA |
| SEQ. ID. NO. 24 | RALAQARALRA |
| SEQ. ID. NO. 25 | ARLQGQGALVGS |

In yet another aspect of the invention, the enhanced neurturin polypeptide will comprise SEQ. ID. NO. 1, 2, 3 or 4. (Table D2)

TABLE D2

Complete amino acid sequences of mature neurturin variants N-1 to N-4 (SEQ. ID. NOs. 1, 2, 3, 4, respectively) and wild type neurturin (SEQ. ID. NO. 5)

| SEQ. ID. NO. | Amino Acid Sequence |
|---|---|
| 1 | ARLGARPCGLRELEVRVSELGLGYASDETVLFRYCAGACE AAARVYDLGLRALRQARALRRERVRAQPCC RPTAYEDEVS FLDAHSRYHT VHELSARECACV |
| 2 | ARLGARPCGLRELEVRVSELGLGYASDETVLFRYCAGACE AAARVYDLGLRRLAQRRRLRAEAVRAQPCC RPTAYEDEVS FLDAHSRYHT VHELSARECACV |
| 3 | ARLGARPCGLRELEVRVSELGLGYASDETVLFRYCAGACE AAARVYDLGL RALAQARALRAERVRAQPCC RPTAYEDEVS FLDAHSRYHT VHELSARECACV |
| 4 | ARLGARPCGLRELEVRVSELGLGYASDETVLFRYCAGACE AAARVYDLGL ARLQGQGALVGSRVRAQPCC RPTAYEDEVS FLDAHSRYHT VHELSARECACV |
| 5 | ARLGARPCGLRELEVRVSELGLGYASDETVLFRYCAGACE AAARVYDLGLRRLRQRRRLRRERVRAQPCC RPTAYEDEVSFLDAHSRYHT VHELSARECACV |

Substituted amino acids in the variants are shown in bold font compared to the wild type sequence.

Enhanced neurturin polypeptides can possess addition amino acid substitutions outside of the region 51 to 63 that do not further substantially affect the binding to heparin or the phosphorylation induction of RET. Additionally, naturally occurring variants of mature human neurturin have been sequenced, and are known in the art to be at least partially functionally interchangeable. It would thus be a routine matter to select a naturally occurring variant of neurturin, for example as shown in Table D3 (see SEQ. ID. NOs. 26 to 30) to create an enhanced neurturin containing one or more conserved amino acid changes based on the sequence of any of the homologues, orthologs, and naturally-occurring isoforms of human as well as other species of neurturin.

TABLE D3

Naturally Occurring Neurturin Variants

| SEQ. ID. No. | Sequence | Reference |
|---|---|---|
| (SEQ. ID. No. 26) | MQRWKAAALA SVLCSSVLSI WMCREGLLLS HRLGPALVPL HRLPRTLDAR IARLAQYRAL LQGAPDAMEL RELTPWAGRP PGPRRRAGPR RRRARARLGA RPCGLRELEV RVSELGLGYA SDETVLFRYC AGACEAAARV YDLGLRRLRQ RRRLRRERVR AQPCCRPTAY EDEVSFLDAH SRYHTVHELS ARECACV | EAW69140.1 Wild type human Neurturin or pre-pro neurturin |
| (SEQ. ID. No. 27) | SRLGA RPCGLRELEV RVSELGLGYA SDETVLFRYC AGACEAAARV YDLGLRRLRQ RRRLRRERVR AQPCCRPTAY EDEVSFLDAH SRYHTVHELS ARECACV | VAR_009498 Human variant of neurturin |
| (SEQ. ID. No. 28) | MSAGSGGHGS AHGGGGEVGR AARARCDGAG APLRPWTSKC ASEAGWARGG RGGSRNPLCS LCEGEPQTPR CLAVRRGPWG ASGPQTPAGE LPSAQLRAEV NICQWRVPAA AASGDTVSSG CPQAYWAPAT AASGCMGPRW SVQARALAPA APRCCDASVL CLAEMPSSLF GSQLPWLFRE ALWDPRMGVL PLPPPARHPP SSRAAFFTTL CSGFLMNRVD VMTDHYAEVD GNQGPRRAPG AWPSALFAPR MQRWKAAALA SVLCSSVLSI WMCRDGLLLS HRLGPALAPL RRPPRTLDAR IARLAQYRAL LQGAPDAVEL RQLTPWAGGA AGPRRRAGPR RRRARTGSRP CGLRELEVRV | XP_854570 [Canis familiaris] |

TABLE D3-continued
Naturally Occurring Neurturin Variants

| SEQ. ID. No. | Sequence | Reference |
|---|---|---|
| | SELGLGYASD ETVLFRYCAG ACEAAARVYD<br>LGLRRLRQRR RVRRERVRAQ PCCRPTAYED<br>EVSFLDAHSR YHTVHELSAR ECACV | |
| (SEQ. ID. No. 29) | MQRWKAAALA SVLCSSVLSI WMCREGLLLG<br>HRLGPALAPL RRPPRTLDAR IARLAQYRAL<br>LQGAPDAVEL RELTPWAGRS PGPRRRPGPR<br>RRRARARSGT RPCGLRELEV RVSELGLGYA<br>SEETVLFRYC AGACEAAARV YDLGLRRLRQ<br>RRRVRRERVR AQPCCRPTAY EDEVSFLDTH<br>SRYHTVHELS ARECACV | XP_603915<br>[Bos taurus] |
| (SEQ. ID. No. 30) | MQRWKAAALA SVLCSSVLSI WMCREGLLLS<br>HRLGPALVPL RRLPRTLDTR IARLAQYRAL<br>LQGAPDAVEL RELTPWAGRP PGPRRRAGPR<br>RRRARARSGA RPCGLRELEV RVSELGYASD<br>ETVLFRYCAG ACEAAARVYD LGLRRLRQRR<br>RLRRERVRAQ PCCRPTAYED EVSFLDAHSR<br>YHTVHELSAR ECACV | XP_001085705<br>[Macaca mulatta] |

It is known in the art to synthetically modify the sequences of proteins or peptides, while retaining their useful activity, and this may be achieved using techniques which are standard in the art and widely described in the literature, e.g., random or site-directed mutagenesis, cleavage, and ligation of nucleic acids, or via the chemical synthesis or modification of amino acids or polypeptide chains. For instance, conservative amino acid mutations changes can be introduced into an enhanced neurturin and are considered within the scope of the invention.

The enhanced neurturin may thus include one or more amino acid deletions, additions, insertions, and/or substitutions based on any of the naturally-occurring isoforms of neurturin outside of the heparin binding region comprising amino acid 51 to 63. These may be contiguous or non-contiguous. Representative variants may include those having 1 to 8, or more preferably 1 to 4, 1 to 3, or 1 or 2 amino acid substitutions, insertions, and/or deletions as compared to any of sequences listed in Table D2.

Similarly it is within the skill in the art to address and/or mitigate immunogenicity concerns if they arise using enhanced human neurturin, e.g., by the use of automated computer recognition programs to identify potential T cell epitopes, and directed evolution approaches to identify less immunogenic forms. Any such modifications, or combinations thereof, may be made and used in any of the methods of the invention, as long as activity is retained.

Enhanced neurturin polypeptides which may be used in any of the methods of the invention may have amino acid sequences which are substantially homologous, or substantially similar to the mature human neurturin amino acid sequence (SEQ. ID. NO. 5), over the length of mature wild type neurturin, excluding the 13 amino acids encompassed by residues 51 to 63 of mature human neurturin; (i.e. is substantially homologous or substantially similar to amino acids 1 to 50, and 64 to 102 of SEQ. ID. NO. 5).

Additionally in some embodiments, the enhanced neurturin polypeptides can include synthetic, or naturally occurring secretion signal sequences, derived from other well characterized secreted proteins such as immunoglobulins, including for example the IgG secretion signal sequence. Specifically wild type neurturin is initially synthesized as a pre-pro-protein, comprising a secretion signal, (amino acids 1-19), and a pre-peptide comprising amino acids 20 to 95 which are processed during biosynthesis and secretion from the cell. Accordingly in one aspect, the enhanced neurturin polypeptides of the invention can include pre and pro sequences identical to, or substantially similar to those in wild type neurturin (SEQ. ID. NO. 26).

In some embodiments such proteins, may be processed by proteolytic cleavage to form the enhanced mature neurturin in situ. Such fusions proteins include for example fusions of the enhanced neurturin to ubiquitin to provide a new N-terminal amino acid, or the use of a secretion signal to mediate high level secretion of the enhanced neurturin into the extracellular medium, or N, or C-terminal epitope tags to improve purification or detection.

In other embodiments, fusion proteins of the enhanced human neurturin to other proteins are also included, and these fusion proteins may increase the enhanced neurturin polypeptides biological activity, targeting, biological life, ability to penetrate the blood brain barrier, or pharmacokinetic properties. Examples of fusion proteins that improve pharmacokinetic properties include without limitation, fusions to human albumin (Osborn et al.: Eur. J. Pharmacol. 456(1-3): 149-158, (2002)), antibody Fc domains, poly Glu or poly Asp sequences, and transferrin. Additionally, fusion with conformationally disordered polypeptide sequences composed of the amino acids Pro, Ala, and Ser ('PASylation') or hydroxyethyl starch (sold under the trademark HESYLATION®) provides a simple way to increase the hydrodynamic volume of the enhanced neurturin. This additional extension adopts a bulky random structure, which significantly increases the size of the resulting fusion protein. By this means the typically rapid clearance of the enhanced neurturin via kidney filtration is retarded by several orders of magnitude. Additionally use of Ig G fusion proteins has also been shown to enable fusion protein proteins with proteins such as GDNF to penetrate the blood brain barrier (Fu et al., (2010) Brain Res. 1352:208-13). An additional fusion protein approach contemplated for use within the present invention includes the fusion of the enhanced neurturin to a multimerization domain. Representative multimerization domains include without limitation coiled-coil dimerization domains such as leucine zipper domains which are found in certain DNA-binding polypeptides, the dimerization domain of an immunoglobulin Fab constant domain, such as an immunoglobulin heavy chain CH1 constant region or an immunoglobulin light chain constant region. In a preferred embodiment, the multimerization domain is derived from tetranectin, and more specifically comprises the tetranectin trimerising structural element, which is described in detail in WO 98/56906.

It will be appreciated that a flexible molecular linker (or spacer) optionally may be interposed between, and covalently join, the enhanced neurturin and any of the fusion proteins disclosed herein. Any such fusion protein may be used in any of the methods, proteins, polynucleotides and host cells of the present invention.

The enhanced neurturin may be in its native form, i.e., as different variants as they appear in nature which may be viewed as functionally equivalent variants of human neurturin, or they may be functionally equivalent natural derivatives thereof, which may differ in their amino acid sequence, e.g., by proteolytic truncation (e.g., from the N- or C-terminus or both) or other post-translational modifications. Naturally-occurring chemical derivatives, including post-translational modifications and degradation products of enhanced human neurturin, are also specifically included in any of the methods of the invention including, e.g., pyroglutamyl, iso-aspartyl, proteolytic, phosphorylated, glycosylated, oxidatized, isomerized, and deaminated variants of enhanced human neurturin.

Chemical modifications of the enhanced neurturin, which retain or stabilize the enhanced neurturin activity or biological half-life, may also be used with any of the methods described herein. Such chemical modification strategies include, without limitation, pegylation, glycosylation, and acylation (Clark et al.: J. Biol. Chem. 271(36): 21969-21977, (1996); Roberts et al.: Adv. Drug. Deliv. Rev. 54(4): 459-476, (2002); Felix et al.: Int. J. Pept. Protein. Res. 46(3-4): 253-264, (1995); Garber A J: Diabetes Obes. Metab. 7(6): 666-74 (2005)). C- and N-terminal protecting groups, stabilizing amino acids, and peptomimetic units may also be included.

A wide variety of PEG derivatives are both available and suitable for use in the preparation of PEG-conjugates. For example, NOF Corp.'s PEG reagents sold under the trademark SUNBRIGHT® Series provides numerous PEG derivatives, including methoxypolyethylene glycols and activated PEG derivatives such as methoxy-PEG amines, maleimides, and carboxylic acids, for coupling by various methods to drugs, enzymes, phospholipids, and other biomaterials and Nektar Therapeutics' Advanced PEGylation technology also offers diverse PEG-coupling technologies to improve the safety and efficacy of therapeutics.

A search of patents, published patent applications, and related publications will also provide those skilled in the art reading this disclosure with significant possible PEG-coupling technologies and PEG-derivatives. For example, U.S. Pat. Nos. 6,436,386; 5,932,462; 5,900,461; 5,824,784; and 4,904,584; the contents of which are incorporated by reference in their entirety, describe such technologies and derivatives, and methods for their manufacture. Thus, one skilled in the art, considering both the disclosure of this invention and the disclosures of these other patents could couple PEG, a PEG-derivative, or some other polymer to the enhanced neurturin for its extended release.

PEG is a well-known polymer having the properties of solubility in water and in many organic solvents, lack of toxicity, lack of immunogenicity, and also clear, colorless, odorless, and stable. One use of PEG is to covalently attach the polymer to insoluble molecules to make the resulting PEG-molecule conjugate soluble. For these reasons and others, PEG has been selected as the preferred polymer for attachment, but it has been employed solely for purposes of illustration and not limitation. Similar products may be obtained with other water-soluble polymers, including without limitation; polyvinyl alcohol, other poly(alkylene oxides) such as poly(propylene glycol) and the like, poly (oxyethylated polyols) such as poly(oxyethylated glycerol) and the like, carboxymethylcellulose, dextran, polyvinyl alcohol, polyvinyl purrolidone, poly-1,3-dioxolane, poly-1, 3,6-trioxane, ethylene/maleic anhydride, and polyaminoacids. One skilled in the art will be able to select the desired polymer based on the desired dosage, circulation time, resistance to proteolysis, and other considerations.

Isomers of the native L-amino acids, e.g., D-amino acids may be incorporated in any of the above forms of the enhanced neurturin, and used in any of the methods of the invention. Additional variants may include amino and/or carboxyl terminal fusions as well as intrasequence insertions of single or multiple amino acids. Longer peptides may comprise multiple copies of one or more of the enhanced neurturin sequences. Insertional amino acid sequence variants are those in which one or more amino acid residues are introduced at a site in the protein. Deletional variants are characterized by the removal of one or more amino acids from the sequence. Variants may include, e.g., different allelic variants as they appear in nature, e.g., in other species or due to geographical variation.

The variants, derivatives, and fusion proteins of enhanced neurturin are functionally equivalent in that they have detectable neurturin activity. More particularly, they exhibit at least 5%, at least 10%, at least 20%, at least 30%, at least 40%, preferably at least 60%, more preferably at least 80% of the activity of human neurturin. Thus they are capable of substituting for neurturin itself. Such activity means any activity exhibited by a native human neurturin, whether a physiological response exhibited in an in vivo or in vitro test system, or any biological activity or reaction mediated by a native human neurturin, e.g., in an enzyme, or cell based assay or in binding to test tissues, membranes, or metal ions. All such variants, derivatives, fusion proteins, or fragments of the enhanced neurturin are included, and may be used in any of the polynucleotides, vectors, host cell and methods disclosed and/or claimed herein, and are subsumed under the term "enhanced neurturin".

Suitable assays for determining functional neurturin activity include RET phosphorylation assays Virtanen et al., (2005) "The first cysteine-rich domain of the receptor GFRalpha1 stabilizes the binding of GDNF" Biochem J. 387:817-824, and neurite outgrowth assays Virtanen et al., (2005) "The first cysteine-rich domain of the receptor GFRalpha1 stabilizes the binding of GDNF" Biochem J. 387:817-824; binding assays to soluble GFRα proteins Virtanen et al., (2005) "The first cysteine-rich domain of the receptor GFRalpha1 stabilizes the binding of GDNF" Biochem J. 387:817-824 or to N-syndecan Maxim M. Bespalov PhD thesis, 18.12. 2009, University of Helsinki, or to NCAM in the presence of GFRα proteins Paratcha et al., (2003) "The neural cell adhesion molecule NCAM is an alternative signaling receptor for GDNF family ligands". 113:867-879, or GPI-anchored GFRα proteins on the cell surface Virtanen et al., (2005) "The first cysteine-rich domain of the receptor GFRalpha1 stabilizes the binding of GDNF" Biochem J. 387:817-824; in vitro survival assays on embryonic dopaminergic neurons Lindholm et al., (2007) "Novel neurotrophic factor CDNF protects and rescues midbrain dopamine neurons in vivo" Nature 448:73-77, embryonic superior servical ganglion sympathetic neurons Yu et al., (2003) "GDNF-deprived sympathetic neurons die via a novel nonmitochondrial pathway." J Cell Biol 163: 987-997, dorsal root ganglion or motoneurons Paveliev et al (2004) "GDNF family ligands activate multiple events during axonal growth in mature sensory neurons" Mol Cell Neurosci 25:453-459; and the ability to protect adult rodent dopaminergic neurons in neurotoxic 6-OHDA Lindholm et al., (2007) "Novel neurotrophic factor CDNF protects and rescues midbrain dopamine neurons in vivo" Nature 448: 73-77, or MPTP lesion assays Schober et al., (2007) "GDNF applied to the MPTP-lesioned nigrostriatal system requires TGF-beta for its neuroprotective action" Neurobiol Dis. 25:378-391 in vivo.

For example, RET phosphorylation assays may be readily conducted using fibroblasts which have been stably transfected with the human RET long isoform (Eketjäll et al., 1999, EMBO J., 18:5901) and which have been transiently transfected with rat GFRα1 or human GFRα2. One day after transfection, the cells are starved in serum free DMEM (Sigma) for four hours, and then the test neurturin applied for 10 min. Thereafter the fibroblasts are lysed and the lysates used for immunoprecipitation of RET (using antibodies to RET for example that are commercially available from Santa Cruz Biotechnology Inc). The immunocomplexes can be collected using Protein G-Sepharose (GE Healthcare) and analysed on 8% SDS-PAGE and Western blotting. The phosphorylation of RET can be detected by antibodies to phosphotyrosine (commercially available from Upstate Biotechnology). Successful phosphorylation of RET shows that the neurturin is functionally active as a neurotrophic factor.

In another aspect, the enhanced neurturin polypeptides of the invention have decreased affinity to bind to heparin or heparan sulfate compared to wild type mature human neurturin. In different embodiments, the affinity of the enhanced neurturin polypeptides may have about a 5 fold, about 10 fold, about 20 fold, about 50 fold, about 100 fold, about 200 fold, about 500 fold, or about 1000 fold lower affinity to heparin or heparan sulfate compared to wild type mature human neurturin.

Accordingly in different aspects, the enhanced neurturin polypeptides of the invention can have an apparent affinity to heparin (i.e. have a $K_d$), of higher than about $5\times10^{-6}$ M, higher than about $1\times10^{-6}$ M, higher than about $5\times10^{-7}$ M, higher than about $1\times10^{-7}$ M, higher than about $5\times10^{-8}$ M, or higher than $1\times10^{-8}$ M. Measured under conditions where wild type mature neurturin has an apparent affinity ($K_d$) for heparin of about 2 to $4\times10^{-9}$ M.

The affinity of the enhanced neurturin polypeptides to heparin may be readily determined using a variety of art recognized methods including, surface plasmon resonance based approaches, for example using instrumentation sold under the trademark BIACORE® by GE Healthcare, or solution based affinity determinations, for example using KinExA technology which is commercially available from Sapidyne. These systems include a large variety of commercially available reagents and coupling reagents to enable the affinity of heparin and the enhanced neurturin to be readily and accurately determined.

Additionally the relative affinity of the enhanced neurturin polypeptides to heparin may be determined by characterizing the ionic strength required to elute the protein from a heparin affinity column, such as those sold under the trademark HITRAP™ heparin HP by GE Healthcare Life Sciences.

Accordingly in one aspect of the invention, the enhanced neurturin polypeptides, can be eluted from a HITRAP™ heparin HP at a concentration of NaCl of less than about 1 molar NaCl. In other aspects of the invention, the enhanced neurturin polypeptides of the invention can be eluted from a HITRAP™ heparin HP at a concentration of NaCl of less than 1.0 M; less than 0.9 M NaCl; less than 0.8 M NaCl; less than 0.7 M NaCl; less than 0.6 M NaCl; less than 0.5 M NaCl; less than 0.4 M NaCl; or less than 0.3 molar NaCl when eluted using a continuous NaCl gradient consisting of 10 mM Hepes pH 7.2 increasing NaCl to 2M. While it is appreciated that a protein will elute from a column over multiple fractions, the majority (i.e. greater than about 75%) of the mass of the polypeptides of the intention will elute at less than the given concentration of NaCl as measured by conventional means such as, but not limit to, Western blotting or ELISA. In a reciprocal type of experiment, a polypeptide of the invention comprising an enhanced neurturin polypeptide will bind poorly to heparin or heparan sulfate either on an immobilized support or in solution at greater than 1 M NaCl. For instance, at a concentration of greater than 1 M NaCl, less than 95%, 90%, 80%, 70%, 60%, 50%, 40%, 30%, 20% or 10% of the polypeptide of the invention will bind.

In another aspect, enhanced neurturin polypeptides of the invention can be coupled to a drug for delivery to a treatment site or coupled to a detectable label to facilitate imaging of a site comprising cells of interest. Methods for coupling proteins to such detectable labels are well known in the art, as are methods for imaging using detectable labels. Labeled proteins may be employed in a wide variety of assays, employing a wide variety of labels. Suitable detection means include the use of detectable labels such as radionuclides, enzymes, coenzymes, fluorescers, chemiluminescers, chromogens, enzyme substrates or co-factors, enzyme inhibitors, prosthetic group complexes, free radicals, particles, dyes, and the like.

Accordingly in one aspect the present invention includes an enhanced neurturin that is labeled at either its N or C terminus with a detectable label, or a drug.

Examples of fluorescent detectable labels include rare earth chelates (europium chelates), fluorescein and its derivatives, rhodamine and its derivatives, dansyl, Lissamine, phycoerythrin, Texas Red, as well as infra-red dyes such as Cy3, Cy5, Cy5.5, Cy7, IR800CW, ICG, and dyes sold under the trademark ALEXA® FLUORS such as ALEXA® FLUORS 680 and 750 all of which are commercially available from Molecular probes and other vendors.

Examples of suitable enzymes include horseradish peroxidase, alkaline phosphatase, β-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material is luminol; examples of bioluminescent materials include luciferase, luciferin, and aequorin; and examples of suitable radioactive material include $^{125}$I, $^{131}$I, $^{35}$S, or $^{3}$H. Such labelled reagents may be used in a variety of well-known assays, such as radioimmunoassays, enzyme immunoassays, e.g., ELISA, fluorescent immunoassays, and the like.

An enhanced neurturin polypeptide according to the invention may be conjugated to a therapeutic moiety such as a cytotoxin, a therapeutic agent, or a radioactive metal ion or radioisotope. Examples of radioisotopes include, but are not limited to, I-131, I-123, I-125, Y-90, Re-188, Re-186, At-211, Cu-67, Bi-212, Bi-213, Pd-109, Tc-99, In-111, and the like. Such conjugates can be used for modifying a given biological response; the drug moiety is not to be construed as limited to classical chemical therapeutic agents. For example, the drug moiety may be a protein or polypeptide possessing a desired biological activity. Such proteins may include, for example, a toxin such as abrin, ricin A, pseudomonas exotoxin, or diphtheria toxin.

II. Polynucleotides Encoding Enhanced Neurturin

In another embodiment, the invention provides an isolated polynucleotide comprising a nucleotide sequence encoding the enhanced neurturin polypeptides of the invention.

In one aspect, the isolated polynucleotide of the invention comprises a nucleotide sequence encoding an enhanced neurturin polypeptide, wherein the enhanced neurturin polypeptide differs from mature wild type neurturin (SEQ. ID. NO. 5) by at least one mutation of a positively charged amino acid in a region comprising amino acids 51 to 63 of the mature wild type neurturin, and wherein the enhanced neurturin has a decreased affinity to heparin compared to the mature wild type neurturin.

In another aspect, the isolated polynucleotide of the invention comprises a nucleotide sequence encoding an enhanced neurturin differs from the corresponding mature wild type neurturin SEQ. ID. NO. 5 by the mutation of at least two of the positively charged amino acids in a region comprising amino acids 51 to 63 of the mature wild type neurturin, and exhibit a decreased affinity to heparin compared to the mature human neurturin.

In another aspect, the isolated polynucleotide of the invention comprises a nucleotide sequence encoding an enhanced neurturin differs from the corresponding mature wild type neurturin SEQ. ID. NO. 5 by the mutation of at least three of the positively charged amino acids in a region comprising amino acids 51 to 63 of the mature wild type neurturin, and exhibit a decreased affinity to heparin compared to the mature human neurturin.

In another aspect, the isolated polynucleotide of the invention comprises a nucleotide sequence encoding an enhanced neurturin differs from the corresponding mature wild type neurturin SEQ. ID. NO. 5 by the mutation of at least five of the positively charged amino acids in a region comprising amino acids 51 to 63 of the mature wild type neurturin, and exhibit a decreased affinity to heparin compared to the mature human neurturin.

In one embodiment, the isolated polynucleotide of the invention comprises a nucleotide sequence encoding an enhanced neurturin which is at least 90% identical to SEQ. ID. NO. 5, over the amino acid sequence of the mature wild type neurturin, except for the 13 amino acids encompassed by residues 51 to 63 of mature human neurturin. In another aspect, the isolated polynucleotide of the invention comprises a nucleotide sequence encoding an enhanced neurturin which is at least 95% identical to SEQ. ID. NO. 5, over the amino acid sequence of the mature wild type neurturin, except for the 13 amino acids encompassed by residues 51 to 63 of mature human neurturin.

In one embodiment, the isolated polynucleotide of the invention comprises a nucleotide sequence encoding an enhanced neurturin which comprises one or more mutations at amino acids 51, 52, 54, 55, 56, 57, 58, 60, 61, 62 or 63 as compared to mature wild type neurturin (SEQ. ID. NO. 5), using the numbering for the 102 amino acid mature wild type neurturin. In one aspect, the isolated polynucleotide of the invention comprises a nucleotide sequence encoding an enhanced neurturin which comprises 1 to 13 amino acid mutations within the region encompassed by residues 51 to 63 of mature human neurturin (SEQ. ID. NO. 5). In one aspect, the isolated polynucleotide of the invention comprises a nucleotide sequence encoding an enhanced neurturin comprising 1, 2, 3, 4, 5, 6, 7, 8, 9, 10, 11, 12 or 13 amino acid mutations within the region encompassed by residues 51 to 63 of mature human neurturin (SEQ. ID. NO. 5) compared to the mature wild type neurturin amino acid sequence. In yet another aspect, the isolated polynucleotide of the invention comprises a nucleotide sequence encoding an enhanced neurturin comprising 3, 5, 7 or 9 amino acid mutations within the region encompassed by residues 51 to 63 of mature human neurturin (SEQ. ID. NO. 5).

In one aspect, the isolated polynucleotide of the invention comprises a nucleotide sequence encoding an enhanced neurturin polypeptide comprising at least one neutral, zwitterionic or negatively charged aliphatic amino acid in the region encompassed by residues 51 to 63 of mature human neurturin (SEQ. ID. NO. 5). In another aspect of any of the isolated polynucleotide of the invention, the polynucleotide comprises a nucleotide sequence encoding an enhanced neurturin polypeptides, comprising at least one amino acid independently selected from the group consisting of glycine, alanine, leucine, valine, serine, and glutamine in the region encompassed by residues 51 to 63 of mature human neurturin (SEQ. ID. NO. 5).

In another aspect of any of the isolated polynucleotide of the invention, the polynucleotide comprises a nucleotide sequence encoding an enhanced neurturin polypeptide comprising a replacement of amino acids 51 to 62 by the sequence ARLQGQGALVGS. In another aspect of any of the isolated polynucleotide of the invention, the polynucleotide comprises a nucleotide sequence encoding a sequence selected from SEQ. ID. No. 6 to 9. (Table D4)

In one aspect, the polynucleotide of the invention comprises a nucleotide sequence that comprises SEQ. ID. NO. 6, 7, 8 or 9.

TABLE D4

Nucleotide sequences of neurturin variants N1 to N4 (SEQ. ID. NO.: 6 to 9, respectively) and mature wild type neurturin (SEQ. ID. NO.: 10).

| SEQ. ID. NO. | Nucleotide Sequence |
|---|---|
| 6 | gcgcggttgggggcgcggccttgcgggctgcgcgagctggaggtgcgcgtgagcgagctggg<br>cctgggctacgcgtccgacgagacggtgctgttccgctactgcgcaggcgcctgcgaggctg<br>ccgcgcgcgtctacgacctcgggctgcgagcactgcgccaggcgcgggccctgcggcgggag<br>cgggtgcgcgcgcagccctgctgccgcccgacggcctacgaggacgaggtgtccttcctgga<br>cgcgcacagccgctaccacacggtgcacgagctgtcggcgcgcgagtgcgcctgcgtgtga |
| 7 | gcgcggttgggggcgcggccttgcgggctgcgcgagctggaggtgcgcgtgagcgagctggg |

TABLE D4-continued

Nucleotide sequences of neurturin variants N1 to N4 (SEQ. ID. NO.: 6 to 9, respectively) and mature wild type neurturin (SEQ. ID. NO.: 10).

| SEQ. ID. NO. | Nucleotide Sequence |
|---|---|
| | cctgggctacgcgtccgacgagacggtgctgttccgctactgcgcaggcgcctgcgag-<br>gctg<br>ccgcgcgcgtctacgacctcgggctgcgacgactggcccagcggcggcgcctgcgggcg-<br>gag<br>gcggtgcgcgcgcagccctgctgccgcccgacggcctacgaggacgaggtgtccttc-<br>ctgga<br>cgcgcacagccgctaccacacggtgcacgagctgtcggcgcgcgagtgcgcctgcgtgtga |
| 8 | gcgcggttgggggcgcggccttgcgggctgcgcgagctggaggtgcgcgtgagc-<br>gagctggg<br>cctgggctacgcgtccgacgagacggtgctgttccgctactgcgcaggcgcctgcgag-<br>gctg<br>ccgcgcgcgtctacgacctcgggctgcgagcactggcccaggcgcgggccctgcgggcg-<br>gag<br>cgggtgcgcgcgcagccctgctgccgcccgacggcctacgaggacgaggtgtccttc-<br>ctgga<br>cgcgcacagccgctaccacacggtgcacgagctgtcggcgcgcgagtgcgcctgcgtgtga |
| 9 | gcgcggttgggggcgcggccttgcgggctgcgcgagctggaggtgcgcgtgagc-<br>gagctggg<br>cctgggctacgcgtccgacgagacggtgctgttccgctactgcgcaggcgcctgcgag-<br>gctg<br>ccgcgcgcgtctacgacctcgggctggcacgactgcagggtcagggcgccctg-<br>gtggggtcc<br>cgggtgcgcgcgcagccctgctgccgcccgacggcctacgaggacgaggtgtccttc-<br>ctgga<br>cgcgcacagccgctaccacacggtgcacgagctgtcggcgcgcgagtgcgcctgcgtgtga |
| 10 | gcgcggttgggggcgcggccttgcgggctgcgcgagctggaggtgcgcgtgagc-<br>gagctggg<br>cctgggctacgcgtccgacgagacggtgctgttccgctactgcgcaggcgcctgcgag-<br>gctg<br>ccgcgcgcgtctacgacctcgggctgcgacgactgcgccagcggcggcgcctgcg-<br>gcgggag<br>cgggtgcgcgcgcagccctgctgccgcccgacggcctacgaggacgaggtgtccttc-<br>ctgga<br>cgcgcacagccgctaccacacggtgcacgagctgtcggcgcgcgagtgcgcctgcgtgtga |

It is understood by one skilled in the art that the genetic code is degenerate and that some amino acids have multiple codons. Therefore, multiple polynucleotides can encode the polypeptides of the invention. Moreover, the polynucleotide sequence can be manipulated for various reasons. Examples include but are not limited to the incorporation of preferred codons to enhance the expression of the polynucleotide in various organisms (see generally Nakamura et al., Nuc. Acid. Res. (2000) 28 (1): 292). In addition, silent mutations can be incorporated in order to introduce, or eliminate restriction sites, decrease the density of CpG dinucleotide motifs (see for example, Kameda et al., Biochem. Biophys. Res. Commun. (2006) 349(4): 1269-1277) or reduce the ability of single stranded sequences to form stem-loop structures: (see, e.g., Zuker M., Nucl. Acid Res. (2003); 31(13): 3406-3415). In addition, expression can be further optimized by including a Kozak consensus sequence [i.e., (a/g)cc(a/g)ccATGg] at the start codon. Kozak consensus sequences useful for this purpose are known in the art (Mantyh et al. PNAS 92: 2662-2666 (1995); Mantyh et al. Prot. Exp. & Purif. 6,124 (1995)).

III. Recombinant Vectors

Another embodiment of the invention provides for recombinant vectors and recombinant viral vectors comprising a polynucleotide whose sequence comprises a nucleotide sequence which encodes for any of the enhanced neurturin polypeptides disclosed herein.

The selection of recombinant vectors suitable for expressing the enhanced neurturin polypeptides of the invention, methods for inserting nucleic acid sequences for expressing the enhanced neurturin into the vector, and methods of delivering the recombinant vector to the cells of interest are within the skill in the art. See, for example Tuschl, T. (2002), Nat. Biotechnol, 20: 446-448; Brummelkamp T R et al. (2002), Science 296: 550-553; Miyagishi M et al. (2002), Nat. Biotechnol. 20: 497-500; Paddison P J et al. (2002), Genes Dev. 16: 948-958; Lee N S et al. (2002), Nat. Biotechnol. 20: 500-505; Paul C P et al. (2002), Nat. Biotechnol. 20: 505-508, Conese et al., Gene Therapy 11: 1735-1742 (2004), and Fjord-Larsen et al., (2005) Exp Neurol 195:49-60 the entire disclosures of which are herein incorporated by reference.

Representative commercially available recombinant expression vectors include, for example, pREP4, pCEP4, pREP7 and pcDNA3.1 and pcDNA™5/FRT from Invitrogen, and pBK-CMV and pExchange-6 Core Vectors from Stratagene.

Recombinant vectors can be administered to a patient directly or in conjunction with a suitable delivery reagent, including the Minis Transit LT1 lipophilic reagent; lipofectin; lipofectamine; cellfectin; polycations (e.g., polylysine) or liposomes.

Selection of recombinant viral vectors suitable for use in the invention, methods for inserting nucleic acid sequences for expressing the enhanced neurturin polypeptide into the vector, and methods of delivering the viral vector to the cells of interest are within the skill in the art. See, for example, Dornburg R (1995), Gene Therap. 2: 301-310; Eglitis M A (1988), Biotechniques 6: 608-614; Miller A D (1990), Hum Gene Therap. 1: 5-14; and Anderson W F (1998), Nature 392: 25-30, the entire disclosures of which are herein incorporated by reference.

Representative commercially available viral expression vectors include, but are not limited to, the adenovirus-based systems, such as the Per.C6 system available from Crucell, Inc., lentiviral-based systems such as pLP1 from Invitrogen, and retroviral vectors such as Retroviral Vectors pFB-ERV and pCFB-EGSH from Stratagene (US).

In general, any viral vector capable of accepting the coding sequences for the enhanced neurturin polypeptides to be expressed can be used, for example vectors derived from adenovirus (AV); adeno-associated virus (AAV); retroviruses (e.g., lentiviruses (LV), Rhabdoviruses, murine leukemia virus); herpes virus, papillomavirus (U.S. Pat. Nos. 6,399,383, & 7,205,126) and the like. The tropism of the viral vectors can also be modified by pseudotyping the vectors with envelope proteins or other surface antigens from other viruses. For example, an AAV vector of the invention can be pseudotyped with surface proteins from vesicular stomatitis virus (VSV), rabies, Ebola, Mokola, and the like. Non infectious pseudovirions, for example of Papillomavirus, may also be used to enable the efficient delivery of genes to mucosal membranes (U.S. Pat. No. 7,205,126, Peng et al., Gene Ther. 2010 Jul. 29 epub).

In one aspect, viral vectors derived from AV and AAV may be used in the present invention. Suitable AAV vectors for expressing the enhanced neurturin of the invention, methods for constructing the recombinant AAV vector, and methods for delivering the vectors into target cells are described in Samulski R et al. (1987), J. Virol. 61: 3096-3101; Fisher K J et al. (1996), J. Virol., 70: 520-532; Samulski R et al. (1989), J. Virol. 63: 3822-3826; U.S. Pat. No. 5,252,479; U.S. Pat. No. 5,139,941; International Patent Application No. WO 94/13788; and International Patent Application No. WO 93/24641, the entire disclosures of which are herein incorporated by reference.

Typically the recombinant vectors and recombinant viral vectors include expression control sequences that direct the expression of the polynucleotide of the invention in various systems, both in vitro and in vivo. For instance, one set of regulatory elements will direct expression in certain mammalian cells or tissues and another set of regulatory elements will direct expression to bacterial cells and yet a third set of regulatory elements will direct expression in baculovirus systems. Some vectors are hybrid vectors that contain regulatory elements necessary for expression in more than one system. Vectors containing these various regulatory systems are commercially available and one skilled in the art will readily be able to clone the polynucleotides of the invention into such vectors.

In some instances, the vectors will possess promoters for expression in a wide variety of cells. In other instances, the vectors will possess promoters that are tissue specific. For example, the promoters direct expression only in neurons. In one aspect, the vector of the invention comprises a polynucleotide whose nucleotide sequence encodes for SEQ. ID. NO. 1, 2, 3, or 4.

IV. Host Cells

In another embodiment, the invention provides a host cell transformed with a vector of the invention. In one aspect, the enhanced neurturin polypeptides of the invention are expressed by the host cell in order to produce or manufacture an enhanced neurturin polypeptide. Such host cells include bacteria, insect cells, yeast cells or mammalian cells. Useful microbial hosts include, but are not limited to, bacteria from the genera *Bacillus, Escherichia* (such as *E. coli*), *Pseudomonas, Streptomyces, Salmonella, Erwinia, Bacillus subtilis, Bacillus brevis*, the various strains of *Escherichia coli* (e.g., HB101, (ATCC NO. 33694) DH5α, DH10 and MC1061 (ATCC NO. 53338)). Many strains of yeast cells known to those skilled in the art are also available as host cells for the expression of polypeptides including those from the genera *Hansenula, Kluyveromyces, Pichia, Rhino-sporidium, Saccharomyces,* and *Schizosaccharomyces,* and other fungi. Preferred yeast cells include, for example, *Saccharomyces cerivisae* and *Pichia pastoris*. Additionally, where desired, insect cell systems can be utilized in to produce enhanced neurturin of the present invention. Such systems are described, for example, by Kitts et al., Biotechniques, 14:810-817 (1993); Lucklow, Curr. Opin. Biotechnol., 4:564-572 (1993); and Lucklow et al. (J. Virol., 67:4566-4579 (1993). Preferred insect cells include Sf-9 and HIS (Invitrogen, Carlsbad, Calif.).

A number of suitable mammalian host cells are also known in the art and many are available from the American Type Culture Collection (ATCC), 10801 University Boulevard, Manassas, Va. 20110-2209). Examples include, but are not limited to, mammalian cells, such as Chinese hamster ovary cells (CHO) (ATCC No. CCL61) CHO DHFR-cells (Urlaub et al., Proc. Natl. Acad. Sci. USA, 97:4216-4220 (1980)), human embryonic kidney (HEK) 293 or 293T cells (ATCC No. CRL1573), PER.C6 cells, NSO, ARPE-19, or 3T3 cells (ATCC No. CCL92). The selection of suitable mammalian host cells and methods for transformation, culture, amplification, screening and product production and purification are known in the art. Other suitable mammalian cell lines are the monkey COS-1 (ATCC No. CRL1650) and COS-7 cell lines (ATCC No. CRL1651), and the CV-1 cell line (ATCC No. CCL70). Further exemplary mammalian host cells include primate cell lines and rodent cell lines, including transformed cell lines. Normal diploid cells, cell strains derived from in vitro culture of primary tissue, as well as primary explants, are also suitable. Candidate cells can be genotypically deficient in the selection gene, or can contain a dominantly acting selection gene. Other suitable mammalian cell lines include, but are not limited to, mouse neuroblastoma N2A cells, HeLa, mouse L-929 cells, 3T3 lines derived from Swiss, Balb-c or NIH mice, BHK or HaK hamster cell lines, which are available from the ATCC. Each of these cell lines is known and available for protein expression.

In another aspect, the host cells may be used to express and delivery an enhanced neurturin via cell therapy. Accordingly in another aspect, the current invention includes a cell therapy for treating a disease or disorder, comprising administering a host cell expressing, or capable of expressing, an enhanced neurturin. In one aspect the disease or disorder is selected from the group consisting of amyotrophic lateral sclerosis, Alzheimer's disease, Parkinson's disease, Huntington's disease, ischemic stroke, acute brain injury, acute spinal cord injury, neuropathic pain, diabetes, erectile dysfunction, hair loss, Hirschsprung's disease, nervous systems tumors, multiple sclerosis, hearing loss, and retinopathy.

Cell therapy involves the administration of cells which have been selected, multiplied and pharmacologically treated or altered (i.e. genetically modified) outside of the body (Bordignon, C. et al, Cell Therapy: Achievements and Perspectives (1999), Haematologica, 84, pp. 1110-1149). Such host cells include for example, primary cells, including macrophages, and stem cells which have been genetically modified to express an enhance neurturin polypeptide. The aim of cell therapy is to replace, repair or enhance the biological function of damaged tissues or organs (Bordignon, C. et al, (1999), Haematologica, 84, pp. 1110-1149).

The use of transplanted cells has been investigated for the treatment of numerous endocrine disorders such as anemia and dwarfism, hematological disorders, kidney and liver failure, pituitary and CNS deficiencies and diabetes mellitus (Uludag et al., Technology of Mammalian Cell Encapsulation (2000), Advanced Drug Delivery Reviews, 42, pp. 29-64). Transplanted cells may function by releasing bioactive compounds such as an enhanced neurturin polypeptide of the invention, to replace endogenous neurturin which is absent or produced in insufficient quantities in an effected system. Examples of such approaches, using other hormones and neurotransmitters, include the transplantation of encapsulated, GDNF-secreting cells to treat Parkinson's disease (Lindvall O, & Wahlberg L U (2008) Exp Neurol. 209(1): 82-88), the use of macrophage mediated GDNF delivery (Biju K, et al., (2010) Mol Ther. 18(8):1536-44), the implantation of pancreatic islet cells for the treatment of insulin-dependent diabetes mellitus (Miyamoto, M, Current Progress and Perspectives in Cell Therapy for Diabetes Mellitus (2001), Human Cell, 14, pp. 293-300.) and the implantation of dopamine producing neurons for the treatment of Parkinson's disease (Lindvall, O. and Hagell, P., Cell Therapy and Transplantation in Parkinson's Disease (2001), Clinical Chemistry and Laboratory Medicine, 39, pp. 356-361).

In comparison to whole organ transplants, cell therapies are more easily available. However, rejection of the transplanted cells by the recipient's immune system is still an issue especially where long term use is desired such as in the case of islet implants for diabetic patients (Morris, P. J., Immunoprotection of Therapeutic Cell Transplants by Encapsulation (1996), Trends in Biotechnology, 14, pp. 163-167). As an alternative to immunosuppression, encapsulation methods have been developed whereby the transplanted cells are physically protected from the recipient's immune system by a membrane barrier (Morris, P. J., Immunoprotection of Therapeutic Cell Transplants by Encapsulation (1996), Trends in Biotechnology, 14, pp. 163-167). The use of encapsulated cells is preferable since the systemic administration of immunosuppressant drugs is associated with deleterious side effects and complications due to non-specific suppression of the immune system.

Accordingly in another aspect, the current invention includes a cell therapy for treating a disease or disorder, comprising administering a host cell expressing, or capable of expressing, an enhanced neurturin, wherein the host cell has been encapsulated.

Encapsulation methods are generally classified into two categories: (1) microencapsulation, typically involving small spherical vesicles ranging in size from 0.3 to 1.5 mm in diameter containing individual cells or small cell masses and (2) macroencapsulation, which involve the larger cell masses in tubular or disc shaped hollow devices (Uludag et al., (2000), Advanced Drug Delivery Reviews, 42, pp. 29-64).

It is believed that, ideally, the membrane will protect the encapsulated cells from immune responses while at the same time be sufficiently permeable to allow for the influx of molecules necessary for cell survival and the secretion of the desired bioactive compounds and waste products. Numerous materials have been employed for cell encapsulation with the polysaccharide alginate being the most common (Rowely, J. A. et al, Alginate Hydrogels as Synthetic Extracellular Matrix Materials (1999), Biomaterials, 20, pp. 45-53). Membranes are typically composed of oppositely charged natural or synthetic polymers which form gelled complexes; with the combination of polyanionic alginate and polycationic poly(L-lysine) being widely used (Uludag et al., (2000), Advanced Drug Delivery Reviews, 42, pp. 29-64). By varying the concentration of the respective polymers and their contact time, porosity of the resultant hydrogel membrane can be modulated. Other commonly used materials include (methyl)acrylmates which tend to be more toxic and agarose, a neutral polymer (Uludag et al., (2000), Advanced Drug Delivery Reviews, 42, pp. 29-64).

Cells or cell masses may be encapsulated by conformal coating techniques whereby the membrane is in direct contact with the cells (Uludag et al., (2000), Advanced Drug Delivery Reviews, 42, pp. 29-64). Alternatively, the membrane may be formed around a core containing the cell mass. The core may be engineered to include components which promote cell survival or cell function such as the inclusion of nutrients and trophic factors.

Membranes or cores may also be engineered to function as a synthetic extracellular matrix (ECM). The addition of ECM components may assist cells in the expression of differentiated functions and the organization of the cell mass within the capsule (Uludag et al., (2000), Advanced Drug Delivery Reviews, 42, pp. 29-64). The use of synthetic ECM has been investigated in relation to adherent cells since the hydrophilic nature of most alginate membranes generally excludes the cell attachment and spreading (Rowely, J. A. et al, Alginate Hydrogels as Synthetic Extracellular Matrix Materials (1999), Biomaterials, 20, pp. 45-53). Alginate hydrogel sheets covalently modified with RGD-containing ligand have been shown to support the growth of myoblasts (Rowely, J. A. et al, Alginate Hydrogels as Synthetic Extracellular Matrix Materials (1999), Biomaterials, 20, pp. 45-53). Cell interaction with modified alginate hydrogels have only been achieved where the cells are grown on flat sheets, as opposed to enclosed capsules (Rowley et al, 1999).

Lim, U.S. Pat. Nos. 4,409,331 and 4,352,883, discloses the use of microencapsulation methods to produce biological materials generated by cells in vitro, wherein the capsules have varying permeabilities depending upon the biological materials of interest being produced. Wu et al, Int. J. Pancreatology, 3:91-100 (1988), disclose the transplantation of insulin-producing, microencapsulated pancreatic islets into diabetic rats. Aebischer et al., Biomaterials, 12:50-55 (1991), disclose the macroencapsulation of dopamine-secreting cells.

Moreover a wide variety of encapsulation mediums can be used in the methods and treatments of the present invention. Examples include: agarose with fibrin, agrarose with Fibronectin, or a combination of Fibronectin and Fibrinogen. Suitable naturally-derived mediums include plant-derived gums, such as the alkali metal alginates and agarose, and other plant-derived substances, such as cellulose and its derivatives (e.g., methylcellulose). Animal tissue-derived mediums such as gelatin and chitosan are also useful. Alternatively, the core matrix can be made of extracellular matrix (ECM) components, as described by Kleinman et al., U.S. Pat. No. 4,829,000. Suitable synthetic hydrogels include polyvinyl alcohol, block copolymer of ethylene-vinylalcohol, sodium polystyrene sulfonate, vinyl-methyl-tribenzyl ammonium chloride and polyphosphazene (Cohen, S. et al. J. Anal. Chem. Soc., 112, pp. 7832-7833 (1990)).

Cells can be encapsulated in hollow fibers or in microcapsules that are several hundred microns in size. The former has the advantage of higher mechanical stability and retrievability. Microcapsules on the other hand have a higher surface to volume ratio for growth of anchorage-dependent cells and lower mass transfer resistance for nutrients supply and product secretion. To combine the strength of the two approaches, microencapsulated cells can further be macroencapsulated, for instance, in hollow fibers; choice of highly permeable hollow fibers would add little to the overall mass transfer resistance.

Microcapsule formulation is a known technology used by the pharmaceutical industry to manufacture sustained release products. In the area of cell encapsulation, gelation of alginates is the most extensively studied system. Alginate is a glycuranan extracted from brown seaweed algae. Calcium or other multivalent counterions chelates contiguous blocks of alpha-1,4-L-guluronan residues present in the polysaccharide. Cell encapsulation is achieved when alginate solution containing suspended living cells is dropped or extruded into a solution containing calcium ions. The microcapsules formed can further be coated by adsorption of polyions such as polylysine, which can be coated by alginate again. Many cell types, including islets, hepatocytes, PCI 12 cells, chondrocytes, and fibroblasts, have been encapsulated by this method.

V. Methods of Use

In another embodiment, the invention comprises a method of preventing or treating cellular degeneration or insufficiency comprising administering to a patient in need of such treatment a therapeutically effective amount of any of the enhanced neurturin polypeptides, recombinant vectors comprising a nucleotide sequence that encodes any of the enhanced neurturin polypeptides, recombinant viral vectors comprising a nucleotide sequence that encodes any of the enhanced neurturin polypeptides, or a host cell expressing any of the recombinant enhanced neurturin polypeptides.

In another embodiment, the invention comprises the use of any of the enhanced neurturin polypeptides, recombinant vectors comprising a nucleotide sequence that encodes any of the enhanced neurturin polypeptides, recombinant viral vectors comprising a nucleotide sequence that encodes any of the enhanced neurturin polypeptides, or a host cell expressing any of the recombinant enhanced neurturin polypeptides for use in treating cellular degeneration or insufficiency.

In one aspect, the cellular degeneration or insufficiency is comprised of neuronal degeneration resulting from a condition selected from the group consisting of peripheral neuropathy, amyotrophic lateral sclerosis, Alzheimer's disease, Parkinson's disease, Huntington's disease, ischemic stroke, acute brain injury, acute spinal cord injury, nervous systems tumors, multiple sclerosis, and infection.

In another aspect, the cellular degeneration or insufficiency is comprised of hematopoietic cell degeneration or insufficiency selected from the group consisting of eosinopenia, basopenia, lymphopenia, monocytopenia, neutropenia, anemias, thrombocytopenia, and stem-cell insufficiencies.

Accordingly in one aspect the present invention includes a method of treating a neurodegenerative brain disease by administering to a patient in need of such treatment a therapeutically effective amount of any of the enhanced neurturin polypeptides, recombinant vectors comprising a nucleotide sequence that encodes any of the enhanced neurturin polypeptides, recombinant viral vectors comprising a nucleotide sequence that encodes any of the enhanced neurturin polypeptides, or a host cell expressing any of the recombinant enhanced neurturin polypeptides.

In another aspect the present invention includes the use of any of enhanced neurturin polypeptides, recombinant vectors comprising a nucleotide sequence that encodes any of the enhanced neurturin polypeptides, recombinant viral vectors comprising a nucleotide sequence that encodes any of the enhanced neurturin polypeptides, or a host cell expressing any of the recombinant enhanced neurturin polypeptides for the treatment of a neurodegenerative brain disease.

In one aspect, of any of these methods, the neurodegenerative disease is selected from the group consisting of amyotrophic lateral sclerosis, Alzheimer's disease, Parkinson's disease, Huntington's disease, and dementia.

In one aspect, the present invention includes a method of arresting, delaying the onset, i.e. the period prior to clinical manifestation of a neurodegenerative brain disease, or to reduce the risk of developing the neurodegenerative brain disease. In another aspect, the present invention includes a method of relieving, alleviating, reducing, reversing, improving or preventing at least one symptom or sign of a neurodegenerative brain disease.

In one aspect, the neurodegenerative disease is amyotrophic lateral sclerosis and such signs and symptoms of the disease include: Difficulty lifting the front part of the foot and toes (footdrop), weakness in the leg, hand weakness or clumsiness, slurring of speech or trouble swallowing, muscle cramps and twitching in your arms, shoulders and tongue, difficulty chewing, swallowing, speaking and breathing.

In one aspect, the neurodegenerative disease is Parkinson's disease, and such signs and symptoms of the disease include: tremor, slowed motion (bradykinesia), rigid muscles, impaired posture and balance, loss of automatic movements, difficulty speaking and dementia.

In one aspect, the neurodegenerative disease is Alzheimer's disease, and such signs and symptoms of the disease include: memory loss, problems with abstract thinking, difficulty finding the right word, disorientation, loss of judgment, difficulty performing familiar tasks and personality changes.

In one aspect, the neurodegenerative disease is Huntington's disease, and such signs and symptoms of the disease include: personality changes, decreased cognitive abilities, mild balance problems, clumsiness, involuntary facial movements, rapid eye movements, swallowing problems, and dementia.

In one aspect, the neurodegenerative disease is dementia, and such signs and symptoms of the disease include: forgetfulness, language difficulties, confusion with time and place, decreased judgment and personality changes.

In another aspect the present invention includes a method of treating neuronal injury by administering to a patient in need of such treatment a therapeutically effective amount of any of the enhanced neurturin polypeptides, recombinant vectors comprising a nucleotide sequence that encodes any of the enhanced neurturin polypeptides, recombinant viral vectors comprising a nucleotide sequence that encodes any of the enhanced neurturin polypeptides, or a host cell expressing any of the recombinant enhanced neurturin polypeptides.

In another aspect the present invention includes the use of any of the enhanced neurturin polypeptides, recombinant vectors comprising a nucleotide sequence that encodes any of the enhanced neurturin polypeptides, recombinant viral vectors comprising a nucleotide sequence that encodes any of the enhanced neurturin polypeptides, or a host cell expressing any of the recombinant enhanced neurturin polypeptides for the treatment of neuronal injury.

In one aspect, such neuronal injury is selected from the group consisting of ischemic stroke, acute brain injury, acute spinal cord injury, and neuropathic pain.

In another aspect the present invention includes a method of treating a disease or disorder associated with aging by administering to a patient in need of such treatment a therapeutically effective amount of any of the enhanced neurturin polypeptides, recombinant vectors comprising a nucleotide sequence that encodes any of the enhanced neurturin polypeptides, recombinant viral vectors comprising a nucleotide sequence that encodes any of the enhanced neurturin polypeptides, or a host cell expressing any of the recombinant enhanced neurturin polypeptides.

In another aspect the present invention includes the use of any of the enhanced neurturin polypeptides, recombinant vectors comprising a nucleotide sequence that encodes any of the enhanced neurturin polypeptides, recombinant viral vectors comprising a nucleotide sequence that encodes any of the enhanced neurturin polypeptides, or a host cell expressing any of the recombinant enhanced neurturin polypeptides for the treatment of a disease or disorder associated with aging.

In one aspect, such disease or disorder is selected from the group consisting of hearing loss, erectile dysfunction, peripheral or autonomic neuropathies, retinopathy and senile dementia.

In another aspect the present invention includes a method of treating a disease or disorder associated with diabetes by administering to a patient in need of such treatment a therapeutically effective amount of any of the enhanced neurturin polypeptides, recombinant vectors comprising a nucleotide sequence that encodes any of the enhanced neurturin polypeptides, recombinant viral vectors comprising a nucleotide sequence that encodes any of the enhanced neurturin polypeptides, or a host cell expressing any of the recombinant enhanced neurturin polypeptides.

In another aspect the present invention includes the use of any of the enhanced neurturin polypeptides, recombinant vectors comprising a nucleotide sequence that encodes any of the enhanced neurturin polypeptides, recombinant viral vectors comprising a nucleotide sequence that encodes any of the enhanced neurturin polypeptides, or a host cell expressing any of the recombinant enhanced neurturin polypeptides for the treatment of a disease or disorder associated with diabetes.

In one aspect, such disease or disorder is selected from hyperglycemia, type I diabetes, type II diabetes and type 1.5 diabetes.

In another embodiment, the invention provides a method for promoting the growth and/or differentiation of a cell, such as a stem cell in culture medium comprising administering to the cell a polypeptide, a vector, a viral vector or a host cell of the invention. The polypeptides, vectors, viral vectors or host cells of the invention can be administered to cells in culture in order to alter a phenotypic and/or genotypic property of the target cell. For instance, certain target cells may be exposed to polypeptides of the invention such that the polypeptides bind to cellular receptors and induce signal transduction in the cell. This signal transduction may induce certain properties in the target cell which are desirable for any number of means. By way of example only and not limiting, the administration of the polypeptides of the invention may induce differentiation in the target cells. These differentiated cells may have a variety of uses including, but not limited to, implantation into a subject in a prophylactic or therapeutic regimen.

In a similar manner, vectors or viral vectors of the invention may be applied to target cells in culture. The transduction of nucleic acids of the invention by either means can result in transient or stable genotypic changes of desirable quality. Lastly, host cells of the invention can by co-cultured with target cells in culture such that the polypeptides or viral vectors of the invention are produced by the host cells. The produced polypeptides or vectors can then bind to the cells in culture to bring about a transient or stable genotypic or phenotypic change as desired. Host cells used in this manner are often considered a "feeder cell" in that properties of the host cell have an impact on the target cells with which they are co-cultured. Host cells of the invention may or may not be irradiated prior to co-culturing with the target cells.

VI. Pharmaceutical Compositions

In one embodiment, the invention provides a pharmaceutical composition comprising a therapeutically effective amount of any of the enhanced neurturin polypeptides, recombinant vectors comprising a nucleotide sequence that encodes any of the enhanced neurturin polypeptides, recombinant viral vectors comprising a nucleotide sequence that encodes any of the enhanced neurturin polypeptides, or a host cell expressing any of the recombinant enhanced neurturin polypeptides.

Pharmaceutical compositions for use in the present invention may be formulated according to techniques and procedures well-known in the art and widely discussed in the literature and may comprise any of the known carriers, diluents, or excipients for proteins, polynucleotides, and host cells respectively. See for example, Gennaro (2000) *Remington: The Science and Practice of Pharmacy*, 20th edition, ISBN: 0683306472.

In one aspect, the compositions may be in the form of sterile aqueous solutions and/or suspensions of the pharmaceutically active ingredients, aerosols, ointments, and the like. Formulations which are aqueous solutions are most preferred. Such formulations typically contain the enhanced itself, water, and one or more buffers which act as stabilizers (e.g., phosphate-containing buffers) and optionally one or more preservatives.

Such formulations containing, e.g., about 5.0 to 250 micrograms, about 5.0 to 200 micrograms, about 5.0 to 150 micrograms, about 5.0 to 120 micrograms, about 5.0 to 100 micrograms, about 5.0 to 80 micrograms, or any of the ranges mentioned above, e.g., about 200 micrograms, about 180 micrograms, about 160 micrograms, about 140 micrograms, about 120 micrograms, about 100 micrograms, about 80 micrograms, about 60 micrograms, or about 40 micrograms of any of the enhanced neurturin polypeptides of the invention, or polynucleotides of the invention, or recombinant vectors of the invention constitute a further aspect of the invention. In one aspect such formulations may be administered once per day, or one per week, by direct infusion, or via intraputamenal injection into the brain (Gill et al., (2003) Nat Med. 9(5):589-95; Lang et al., (2006) Ann Neurol. 59(3):459-66).

Pharmaceutical compositions for the enhanced neurturin polypeptides may include pharmaceutically acceptable salts of the enhanced neurturin polypeptides. For a review on suitable salts, see *Handbook of Pharmaceutical Salts: Properties, Selection, and Use* by Stahl and Wermuth (Wiley-VCH, 2002). Suitable base salts are formed from bases which form non-toxic salts. Representative examples include the aluminium, arginine, benzathine, calcium, choline, diethylamine, diolamine, glycine, lysine, magnesium, meglumine, olamine, potassium, sodium, tromethamine, and zinc salts. Hemisalts of acids and bases may also be formed, e.g., hemisulphate and hemicalcium salts.

Pharmaceutical compositions for the enhanced neurturin polypeptides to be used in the invention suitable for parenteral administration may comprise sterile aqueous solutions and/or suspensions of the pharmaceutically active ingredients preferably made isotonic with the blood of the recipient, generally using sodium chloride, glycerin, glucose, mannitol, sorbitol, and the like.

Pharmaceutical compositions for the enhanced neurturin polypeptides of the invention suitable for oral administration may, e.g., comprise peptides in sterile purified stock powder form preferably covered by an envelope or envelopes (enterocapsules) protecting from degradation of the peptides in the stomach and thereby enabling absorption of these substances from the gingiva or in the small intestines. The total amount of active ingredient in the composition may vary from 99.99 to 0.01 percent of weight.

In the present methods, the polynucleotides of the invention can be administered to the subject either alone, in conjunction with a delivery reagent, or as a recombinant vector or viral vector which expresses the polynucleotide. Suitable delivery reagents for administration in conjunction with the present recombinant vectors include the Mirus Transit TKO lipophilic reagent; lipofectin; lipofectamine; cellfectin; or polycations (e.g., polylysine), or liposomes.

A preferred delivery reagent is a liposome. Liposomes can aid in the delivery of the recombinant vector to a particular tissue, and can also increase the blood half-life of the vector. Liposomes suitable for use in the invention are formed from standard vesicle-forming lipids, which generally include neutral or negatively charged phospholipids and a sterol, such as cholesterol. The selection of lipids is generally guided by consideration of factors such as the desired liposome size and half-life of the liposomes in the blood stream. A search of patents, published patent applications, and related publications will also provide those skilled in the art reading this disclosure with significant possible liposomal technologies. U.S. Pat. Nos. 6,759,057; 6,406,713; 6,352,716; 6,316,024; 6,294,191; 6,126,966; 6,056,973; 6,043,094; 5,965,156; 5,916,588; 5,874,104; 5,215,680; and 4,684,479; the contents of which are incorporated herein by reference, describe liposomes and lipid-coated microbubbles, and methods for their manufacture.

Liposomes may be comprised of any lipid or lipid combination known in the art. For example, the vesicle-forming lipids may be naturally-occurring or synthetic lipids, including phospholipids, such as phosphatidylcholine, phosphatidylethanolamine, phosphatidic acid, phosphatidylserine, phosphatidylglycerol, phosphatidylinositol, and sphingomyelin as disclosed in U.S. Pat. Nos. 6,056,973 and 5,874,104. The vesicle-forming lipids may also be glycolipids, cerebrosides, or cationic lipids, such as 1,2-dioleyloxy-3-(trimethylamino) propane (DOTAP); N—; 1-(2,3,-ditetradecyloxy)propyl; —N,N-dimethyl-N-hydroxyethylammonium bromide (DMRIE); N 2,3,-dioleyloxy)propyl; N,N-dimethyl-N-hydroxy ethylammonium bromide (DORIE); N; 1-(2,3-dioleyloxyl)propyl N,N,N-trimethylammonium chloride (DOTMA); 3; N—(N',N'-dimethylaminoethane)carbamoly; cholesterol (DC-Choi); or dimethyldioctadecylamnionium (DDAB) also as disclosed in U.S. Pat. No. 6,056,973. Cholesterol may also be present in the proper range to impart stability to the vesicle as disclosed in U.S. Pat. Nos. 5,916,588 and 5,874,104.

The liposomes for use in any of the methods of the invention can be manufactured by standard techniques known to those of skill in the art. For example, in one embodiment, as disclosed in U.S. Pat. No. 5,916,588, a buffered solution of the active agent is prepared. Then a suitable lipid, such as hydrogenated soy phosphatidylcholine, and cholesterol, both in powdered form, are dissolved in chloroform or the like and dried by roto-evaporation. The lipid film thus formed is resuspended in diethyl ether or the like and placed in a flask, and sonicated in a water bath during addition of the buffered solution of the active agent. Once the ether has evaporated, sonication is discontinued and a stream of nitrogen is applied until residual ether is removed. Other standard manufacturing procedures are described in U.S. Pat. Nos. 6,352,716; 6,294,191; 6,126,966; 6,056,973; 5,965,156; and 5,874,104. The liposomes of this invention can be produced by any method generally accepted in the art for making liposomes, including, without limitation, the methods of the above-cited documents (the contents of which are incorporated herein by reference).

In one aspect, the liposomes encapsulating the present recombinant vectors comprise a ligand molecule that can target the liposome to a particular cell or tissue. In one aspect, the liposomes encapsulating the present vectors or polynucleotides are modified so as to avoid clearance by the mononuclear macrophage and reticuloendothelial systems, for example by having opsonization-inhibition moieties bound to the surface of the structure. In one embodiment, a liposome of the invention can comprise both opsonization-inhibition moieties and a ligand.

Opsonization-inhibiting moieties for use in preparing the liposomes of the invention are typically large hydrophilic polymers that are bound to the liposome membrane. As used herein, an opsonization inhibiting moiety is "bound" to a liposome membrane when it is chemically or physically attached to the membrane, e.g., by the intercalation of a lipid-soluble anchor into the membrane itself, or by binding directly to active groups of membrane lipids. These opsonization-inhibiting hydrophilic polymers form a protective surface layer which significantly decreases the uptake of the liposomes by the macrophage-monocyte system ("MMS") and reticuloendothelial system ("RES"); e.g., as described in U.S. Pat. No. 4,920,016, the entire disclosure of which is herein incorporated by reference. Liposomes modified with opsonization-inhibition moieties thus remain in the circulation much longer than unmodified liposomes.

Suitable hydrophilic polymers for surrounding the liposomes include, without limitation, polyethylene glycol (PEG), polyvinylpyrrolidone, polyvinylmethylether, polymethyloxazoline, polyethyloxazoline, polyhydroxypropyloxazoline, polyhydroxypropylmethacrylamide, polymethacrylamide, polydimethylacrylamide, polyhydroxypropylmethacrylate, polyhydroxethylacrylate, hydroxymethylcellulose hydroxyethylcellulose, polyethyleneglycol, polyaspartamide and hydrophilic peptide sequences as described in U.S. Pat. Nos. 6,316,024; 6,126,966; 6,056,973; 6,043,094; the contents of which are incorporated by reference in their entirety.

VII. Combination Therapies

The present invention also includes combination therapies comprising administering to a patient a therapeutic dose of the enhanced neurturin polypeptides, in combination with a second active agent.

In one aspect, the second active agent is selected from the group consisting of L-DOPA, BDNF, GFRalpha2, and CDNF.

In this context "administered in combination" means: (1) part of the same unitary dosage form; (2) administration separately, but as part of the same therapeutic treatment program or regimen, typically but not necessarily, on the same day. When the enhanced neurturin is administered as adjuvant therapy with a second active agent such as L-DOPA, preferably, the enhanced neurturin may be administered at a fixed daily, or weekly dosage, and the L-DOPA taken on an as needed basis.

The routes of administration of the second active agent can be any of those known to the art. The second active agent can be formulated as known in the art, usually together with a pharmaceutically acceptable carrier or diluent, for example as a tablet, capsule, lozenge, troche, elixir, solution, or suspension for oral administration, in a suitable injectable vehicle for parenteral administration, or as a lotion, ointment or cream for topical application.

The exact dose of each component administered will, of course, differ depending on the specific components prescribed, on the subject being treated, on the severity of the disease or disorder, on the manner of administration and on the judgment of the prescribing physician.

VIII. Methods of Administration

Pharmaceutical compositions comprising a therapeutically effective amount of any of the enhanced neurturin polypeptides, recombinant vectors comprising a nucleotide sequence that encodes any of the enhanced neurturin polypeptides, recombinant viral vectors comprising a nucleotide sequence that encodes any of the enhanced neurturin polypeptides, or a host cell expressing any of the recombinant enhanced neurturin polypeptides may be administered directly into the blood stream, into muscle, or into an internal organ.

Suitable means for parenteral administration include intravenous, intra-arterial, intraperitoneal, intrathecal, intraparenchymal, intraventricular, intraurethral, intrasternal, intracranial, intramuscular, intrasynovial, and subcutaneous. Suitable devices for parenteral administration include needle (including microneedle) injectors, needle-free injectors, and infusion techniques.

Parenteral formulations for the enhanced neurturin polypeptides are typically aqueous solutions which may contain excipients such as salts, carbohydrates, and buffering agents, (typically with a pH of from 3 to 9, and in one aspect at a pH of about 5, and with a NaCl concentration of about 150 mM.

For some applications, parenteral formulations may be more suitably formulated as a sterile non-aqueous solution or as a dried form to be used in conjunction with a suitable vehicle such as sterile, pyrogen-free water. The preparation of parenteral formulations under sterile conditions, e.g., by lyophilization, may readily be accomplished using standard pharmaceutical techniques well-known to those skilled in the art.

Formulations for parenteral administration may be formulated to be immediate and/or sustained release. Sustained release compositions include delayed, modified, pulsed, controlled, targeted and programmed release. Thus the enhanced neurturin polypeptides may be formulated as a suspension or as a solid, semi-solid, or thixotropic liquid for administration as an implanted depot providing sustained release of the enhanced neurturin polypeptides. Examples of such formulations include without limitation, drug-coated stents and semi-solids and suspensions comprising drug-loaded poly(DL-lactic-co-glycolic) acid (PGLA), poly(DL-lactide-co-glycolide) (PLG) or poly(lactide) (PLA) lamellar vesicles or microparticles, hydrogels (Hoffman A S: *Ann. N.Y. Acad. Sci.* 944: 62-73 (2001)), poly-amino acid nanoparticles systems, sold under the trademark MEDUSA® developed by Flamel Technologies Inc., non aqueous gel systems sold under the trademark ATRIGEL® developed by Atrix, Inc., and Sucrose Acetate Isobutyrate Extended Release formulations sold under the trademark SABER® developed by Durect Corporation, and lipid-based systems developed by SkyePharma and sold under the trademark DEPOFOAM®.

Sustained release devices capable of delivering desired doses of the enhanced neurturin polypeptides over extended periods of time are known in the art. For example, U.S. Pat. Nos. 5,034,229; 5,557,318; 5,110,596; 5,728,396; 5,985,305; 6,113,938; 6,156,331; 6,375,978; and 6,395,292; teach osmotically-driven devices capable of delivering an active agent formulation, such as a solution or a suspension, at a desired rate over an extended period of time (i.e., a period ranging from more than one week up to one year or more). Other exemplary sustained release devices include regulator-type pumps that provide constant flow, adjustable flow, or programmable flow of beneficial agent formulations, which are available from Medtronic including the Intrathecal pumps sold under the trademark SYNCHROMED INFUSION SYSTEM®, the Johnson and Johnson systems sold under the trademark CODMAN® division pumps, and INSET® technologies pumps. Further examples of devices are described in U.S. Pat. Nos. 6,283,949; 5,976,109; 5,836,935; and 5,511,355.

Pharmaceutical compositions comprising a therapeutically effective amount of any of the enhanced neurturin polypeptides, recombinant vectors comprising a nucleotide sequence that encodes any of the enhanced neurturin polypeptides, recombinant viral vectors comprising a nucleotide sequence that encodes any of the enhanced neurturin polypeptides, or a host cell expressing any of the recombinant enhanced neurturin polypeptides may be administered, directly to the central nervous system or brain. This approach typically allows for much smaller doses than must be delivered orally or via other routes of injection. Side effects of the drugs are often reduced or eliminated. Further, the compositions are delivered across the blood brain barrier.

Accordingly in one aspect of the invention, the pharmaceutical compositions comprising a therapeutically effective amount of any of the enhanced neurturin polypeptides, recombinant vectors comprising a nucleotide sequence that encodes any of the enhanced neurturin polypeptides, recombinant viral vectors comprising a nucleotide sequence that encodes any of the enhanced neurturin polypeptides, or a host cell expressing any of the recombinant enhanced neurturin polypeptides are administered by an intrathecal injection into the spinal canal (intrathecal space surrounding the spinal cord).

In another aspect, the pharmaceutical compositions comprising a therapeutically effective amount of any of the enhanced neurturin polypeptides, recombinant vectors comprising a nucleotide sequence that encodes any of the enhanced neurturin polypeptides, recombinant viral vectors comprising a nucleotide sequence that encodes any of the enhanced neurturin polypeptides, or a host cell expressing any of the recombinant enhanced neurturin polypeptides are administered directly to the brain using intraparenchymal, injection, intranasal delivery through the olfactory epithelium (Illum et al., (2003) J. Contol. Release 87 187-98, Sakane et al., (1991) Chem. Pharm. Bull. 39 1458-2456, Hanson et al., (2008) BMC Neurosci. 10 (9 Suppl 3) S5), or convection enhanced delivery (Pasha & Gupta (2010) Expert Opin. Drug. Deliv. 7(1) 113-135, Allaed et al., (2009) Biomaterials 30(12) 2302-18)

In some methods of use, specific types of administration of any of the disclosed pharmaceutical formulations are preferred. For example, in one aspect of the claimed methods for the treatment of ALS, Alzheimer's disease, Parkinson's disease, Huntington's disease, and acute brain injury, intraparenchymal delivery is preferred. Moreover such intraparenchymal delivery may be targeted to specific regions of the brain. For example, direct stereotactic injection into specific regions of the brain, is preferred for the treatment of Parkinson's disease. Here intraputamenal infusion of any of the pharmaceutical compositions comprising a therapeutically effective amount of any of the enhanced neurturin polypeptides, recombinant vectors comprising a nucleotide sequence that encodes any of the enhanced neurturin polypeptides, recombinant viral vectors comprising a nucleotide sequence that encodes any of the enhanced neurturin polypeptides, or a host cell expressing any of the recombinant enhanced neurturin polypeptides is preferred.

The main function of the putamen is to regulate movements and influence various types of learning. It employs dopamine to perform its functions. In Parkinson's disease the putamen plays a key role because its inputs and outputs are interconnected to the substantia nigra and the globus pallidus. In Parkinson's disease the activity in direct pathways to interior globus pallidus decreases and activity in indirect pathways to external globus pallidus increases. Together these actions cause excessive inhibition of the thalamus.

Moreover it has been shown that intraputamenal infusion of glial cell-derived neurotrophic factors (Hutchinson, M. et al., Journal of Neuroscience Methods 163 (2007) 190-192; Love, S. et al, Nature Medicine 11(7) (2005) 703-704; Gill, S. et al., Nature Medicine 9(5) (2003) 589-595) can be used to treat Parkinson's disease. Infusion of GDNF into the posterior putamen causes a marked local increase in tyrosine hydroxylase-immunopositive nerve fibers, and there may also be sprouting of fibers in the substantia nigra. Although it remains unclear how much of the increase in tyrosine hydroxylase-immunopositive nerve fibers results from axonal sprouting and how much results from upregulation of tyrosine hydroxylase in spared but dysfunctional fibers, In either case, however, the findings provide support for the sustained clinical improvement in humans receiving intraputaminal infusion of the closely related GDNF.

Enhanced neurturin polypeptides for use in the present invention may also be administered topically, (intra)dermally, or transdermally to the skin or mucosa. In this case topical administration may be preferred to treat hearing loss, or erectile dysfunction. Typical formulations for this purpose include gels, hydrogels, lotions, solutions, creams, ointments, dusting powders, dressings, foams, films, skin patches, wafers, implants, sponges, fibers, bandages, and microemulsions. Liposomes may also be used. Typical carriers include alcohol, water, mineral oil, liquid petrolatum, white petrolatum, glycerin, polyethylene glycol, and propylene glycol. Penetration enhancers may be incorporated— see, e.g., Finnin and Morgan: *J. Pharm. Sci.* 88(10): 955-958, (1999). Other means of topical administration include delivery by electroporation, iontophoresis, phonophoresis, sonophoresis, and microneedle or needle-free injection for example using the systems sold under the trademarks POWDERJECT™, and BIOJECT™.

Formulations for topical administration may be formulated to be immediate and/or modified release. Modified release formulations include delayed, sustained, pulsed, controlled, targeted and programmed release.

In another embodiment of the present invention, the sustained release of enhanced neurturin polypeptides into the blood comprises a sustained release composition comprising enhanced neurturin polypeptides that is packaged in a microsphere. Microspheres have demonstrated utility in delivering beneficial active agents to a target area in a controlled manner over prolonged periods of time. Microspheres are generally biodegradable and can be used for subcutaneous, intramuscular, and intravenous administration.

Generally, each microsphere is composed of an active agent and polymer molecules as disclosed in U.S. Pat. No. 6,268,053, the active agent may be centrally located within a membrane formed by the polymer molecules, or, alternatively, dispersed throughout the microsphere because the internal structure comprises a matrix of the active agent and a polymer excipient. Typically, the outer surface of the microsphere is permeable to water, which allows aqueous fluids to enter the microsphere, as well as solubilized active agent and polymer to exit the microsphere.

In one embodiment, the polymer membrane comprises cross-linked polymers as disclosed in U.S. Pat. No. 6,395,302. When the pore sizes of the cross-linked polymer are equal or smaller than the hydrodynamic diameter of the active agent, the active agent is essentially released when the polymer is degraded. On the other hand, if the pore sizes of the cross-linked polymers are larger than the size of the active agent, the active agent is at least partially released by diffusion.

Additional methods for making microsphere membranes are known and used in the art and can be used in the practice of the invention disclosed herein. Typical materials for the outer membrane include the following categories of polymers: (1) carbohydrate-based polymers, such as methylcellulose, carboxymethyl cellulose-based polymers, dextran, polydextrose, chitins, chitosan, and starch (including hetastarch), and derivatives thereof; (2) polyaliphatic alcohols such as polyethylene oxide and derivatives thereof including PEG, PEG-acrylates, polyethyleneimine, polyvinyl acetate, and derivatives thereof; (3) polyvinyl polymers such as polyvinyl alcohol, polyvinylpyrrolidone, poly(vinyl)phosphate, poly(vinyl)phosphonic acid, and derivatives thereof; (4) polyacrylic acids and derivatives thereof; (5) polyorganic acids, such as polymaleic acid, and derivatives thereof; (6) polyamino acids, such as polylysine, and poly-imino acids, such as polyimino tyrosine, and derivatives thereof; (7) co-polymers and block co-polymers, such as poloxamer 407 or Pluronic L-101; polymer, and derivatives thereof; (8) tert-polymers and derivatives thereof; (9) polyethers, such as poly(tetramethylene ether glycol), and derivatives thereof; (10) naturally-occurring polymers, such as zein, chitosan and pullulan, and derivatives thereof; (11) polyimids, such as poly n-tris(hydroxymethyl)methylmethacrylate, and derivatives thereof; (12) surfactants, such as polyoxyethylene sorbitan, and derivatives thereof; (13) polyesters such polyethylene glycol) (n) monomethyl ether mono(succinimidyl succinate)ester, and derivatives thereof; (14) branched and cyclo-polymers, such as branched PEG and cyclodextrins, and derivatives thereof; and (15) polyaldehydes, such as poly(perfluoropropylene oxide-b-perfluoroformaldehyde), and derivatives thereof as disclosed in U.S. Pat. No. 6,268,053, the contents of which are incorporated herein by reference. Other typical polymers known to those of ordinary skill in the art include poly(lactide-co-glycolide), polylactide homopolymer; polyglycolide homopolymer; polycaprolactone; polyhydroxybutyrate-polyhydroxyvalerate copolymer; poly(lactide-co-caprolactone); polyesteramides; polyorthoesters; poly 13-hydroxybutyric acid; and polyanhydrides as disclosed in U.S. Pat. No. 6,517,859, the contents of which are incorporated herein by reference.

In one embodiment, the microsphere of the present invention are attached to or coated with additional molecules. Such molecules can facilitate targeting, enhance receptor mediation, and provide escape from endocytosis or destruction. Typical molecules include phospholipids, receptors, antibodies, hormones, and polysaccharides. Additionally, one or more cleavable molecules may be attached to the outer surface of microspheres to target it to a predetermined site. Then, under appropriate biological conditions, the molecule is cleaved causing release of the microsphere from the target.

The microspheres for use in the sustained release compositions are manufactured by standard techniques. For example, in one embodiment, volume exclusion is performed by mixing the active agent in solution with a polymer or mixture of polymers in solution in the presence of an energy source for a sufficient amount of time to form particles as disclosed in U.S. Pat. No. 6,268,053. The pH of the solution is adjusted to a pH near the isoelectric point (pI) of the macromolecule. Next, the solution is exposed to an energy source, such as heat, radiation, or ionization, alone or in combination with sonication, vortexing, mixing or stirring, to form microparticles. The resulting microparticles are then separated from any unincorporated components present in the solution by physical separation methods well-known to those skilled in the art and may then be washed. Other standard manufacturing procedures are described in U.S. Pat. Nos. 6,669,961; 6,517,859; 6,458,387; 6,395,302; 6,303,148; 6,268,053; 6,090,925; 6,024,983; 5,942,252; 5,981,719; 5,578,709; 5,554,730; 5,407,609; 4,897,268; and 4,542,025; the contents of which are incorporated by reference in their entirety. Microspheres are well-known and readily available to one of ordinary skill in the art from companies experienced in providing such technologies for extended release drug delivery. For example, Epic Therapeutics, a subsidiary of Baxter Healthcare Corp., developed a protein-matrix drug delivery system that produces bio-erodible protein microspheres in a totally water-based process, which is sold under the trademark PROMAXX®; OctoPlus developed a cross-linked dextran microsphere system sold under the trademark OCTODEX® that releases active ingredients based on bulk degradation of matrix rather than based on surface erosion.

A search of patents, published patent applications, and related publications will also provide those skilled in the art reading this disclosure with significant possible microsphere technologies for use in formulating sustained release compositions. For example, U.S. Pat. Nos. 6,669,961; 6,517,859; 6,458,387; 6,395,302; 6,303,148; 6,268,053; 6,090,925; 6,024,983; 5,942,252; 5,981,719; 5,578,709; 5,554,730; 5,407,609; 4,897,268; and 4,542,025; the contents of which are incorporated by reference in their entirety, describe microspheres and methods for their manufacture. One skilled in the art, considering both the disclosure of this invention and the disclosures of these other patents could make and use microspheres for the sustained release of enhanced neurturin polypeptides for use in any of the methods or kits claimed herein.

The enhanced neurturin polypeptides can be administered intranasally or by inhalation, typically in the form of a dry powder (either alone, as a mixture, e.g., in a dry blend with lactose, or as a mixed component particle, e.g., mixed with phospholipids, such as phosphatidylcholine) from a dry powder inhaler, as an aerosol spray from a pressurized container, pump, spray, atomizer (preferably an atomizer using electro hydrodynamics to produce a fine mist), or nebulizer, with or without the use of a suitable propellant, such as 1,1,1,2-tetrafluoroethane or 1,1,1,2,3,3,3-heptafluoropropane, or as nasal drops. For intranasal use, the powder may comprise a bioadhesive agent, e.g., chitosan or cyclodextrin.

The pressurized container, pump, spray, atomizer, or nebulizer contains a solution or suspension of the compound(s) of the invention comprising, e.g., ethanol, aqueous ethanol, or a suitable alternative agent for dispersing, solubilizing, or extending release of the active, a propellant(s) as solvent and an optional surfactant, such as sorbitan trioleate, oleic acid, or an oligolactic acid.

Prior to use in a dry powder or suspension formulation, the drug product is micronized to a size suitable for delivery by inhalation (typically less than 5 μm). This may be achieved by any appropriate method, such as spiral jet milling, fluid bed jet milling, supercritical fluid processing to form nanoparticles, high pressure homogenization, or spray drying.

Capsules (made, e.g., from gelatin or hydroxypropylmethylcellulose), blisters and cartridges for use in an inhaler or insufflator may be formulated to contain a powder mix of the compound of the invention, a suitable powder base such as lactose or starch and a performance modifier such as 1-leucine, mannitol, or magnesium stearate. The lactose may be anhydrous or in the form of the monohydrate, preferably the latter. Other suitable excipients include dextran, glucose, maltose, sorbitol, xylitol, fructose, sucrose, and trehalose.

A suitable solution formulation for use in an atomizer using electro hydrodynamics to produce a fine mist may contain from 1 μg to 20 mg of the enhanced neurturin per actuation and the actuation volume may vary from 1 μL to 100 μL. A typical formulation may comprise enhanced neurturin polypeptides, propylene glycol, sterile water, ethanol, and sodium chloride. Alternative solvents that may be used instead of propylene glycol include glycerol and polyethylene glycol. Suitable flavors, such as menthol and levomenthol, or sweeteners, such as saccharin or saccharin sodium, may be added to those formulations of the invention intended for inhaled/intranasal administration. Formulations for inhaled/intranasal administration may be formulated to be immediate and/or modified release using, e.g., PGLA. Modified release formulations include delayed, sustained, pulsed, controlled, targeted, and programmed release.

In the case of dry powder inhalers and aerosols, the dosage unit is determined by means of a valve that delivers a metered amount. Units in accordance with the invention are typically arranged to administer a metered dose or "puff" containing from 0.1 mg to 10 mg of an enhanced neurturin polypeptide. The overall daily dose will typically be in the range 0.1 mg to 20 mg that may be administered in a single dose or, more usually, as divided doses throughout the day.

Intranasal delivery is a needle-free, patient-friendly administration route, which enables the blood barrier to be bypassed. Moreover CSF fluid, which appears to move out of the arachoid space, re-circulates back into the subarachonoid CSF and may carry drug applied to the olfactory mucosa back into the subarachnoid space of the CNS (Begley et al., (2004) Pharmacol. Ther. 104 29-45). Additionally, the simplicity of nasal delivery allows for self-administration in a home setting. This route is clearly of great advantage over parenteral administration which has generally to be given under medical supervision. Other advantages of intranasal delivery include the high permeability of the nasal epithelium and, as a result of the rather large surface area of the nasal cavity and the relatively high blood flow, rapid absorption. Compared to other non-injection administrations, such as oral formulation, nasal delivery is an attractive route for its characteristics of avoiding liver first-pass effect, rapid onset action and a higher bioavailability (Hussain, Adv. Drug Deliv. Rev. (1998) 29(1-2): 39-49; Ilium, J. Control Release (2003) 87(1-3): 187-98).

Historically, the bioavailability of therapeutic peptides and proteins after nasal administration tends to be relatively low due primarily to their large molecular size to enable easy passage and due to rapid enzyme degradation. As the number of amino acids increases beyond about 20, bioavailability typically becomes very low (Wearly, Crit. Rev. Ther. Drug Carrier Syst. 1991; 8: 331-394).

Despite these limitations, some peptide products have successfully reached the market as intranasal formulations (Ilium, The nasal route for delivery of polypeptides. In: Peptide and Protein Drug Delivery. Eds. Frokjaer, S., Christrup, L., Krogsgaard-Larsen, P., Munksgaard, Copenhagen 1990, p 157-170). FDA approved examples include DDAVP®, MIACALCIN™ (calcitonin) and SYNAREL™ (nafarelin). Clinical trials have demonstrated that influenza (trivalent) and diphtheria toxin (CRM-197) can be delivered nasally with good effect (Davis, Adv. Drug Del. Rev. (2001) 51: 21-42). Larsen et al. (Eur. J. Clin. Pharmacol. 1987; 33: 155-159) concluded that intranasal application of the low molecular weight polypeptide buserelin represented a reliable mode of administration. Other examples of intranasal formulations of peptides such as insulin, human growth hormone, glucagon, hirudin, human interferon-β and human parathyroid hormone are discussed in Costantino et al. (www.ondrugdelivery.com, 2005; Sakr, Int. J. Pharmaceutics 1996, 132: 189-194; O'Hagan et al., Pharm. Res. 1990, 7: 772-776; Cefalu, Diabetes Care 2004, 27: 239-245; Zhang et al., Biol. Pharm. Bull 2005, 28: 2263-2267).

Moreover several drugs have been delivered successfully to the brain after intranasal administration (Yu et al., (2005) Neurosci. Lett. 387(1) 5-10, Reger et al., (2008) J. Alzheimer's Dis. 13(3) 323-31, Thorne et al., (2004) Neuroscience 127 481-96). Methods and pharmaceutical compositions for intranasal delivery are additionally taught in US20100129354, US20030077300, U.S. Pat. No. 7,244,709 and U.S. Pat. No. 7,812,120.

Accordingly in one aspect of the invention, the pharmaceutical compositions comprising a therapeutically effective amount of any of the enhanced neurturin polypeptides, recombinant vectors comprising a nucleotide sequence that encodes any of the enhanced neurturin polypeptides, recombinant viral vectors comprising a nucleotide sequence that encodes any of the enhanced neurturin polypeptides, or a host cell expressing any of the recombinant enhanced neurturin polypeptides are administered by intranasal administration. In another aspect, invention, the pharmaceutical compositions are formulated for intranasal administration, and optionally comprise one or more agents to increase intranasal delivery.

The following examples are intended to illustrate, but not to limit, the invention in any manner, shape, or form, either explicitly or implicitly. While they are typical of those that might be used, other procedures, methodologies, or techniques known to those skilled in the art may alternatively be used.

EXAMPLES

Example 1

Molecular Modeling

An initial analysis of the primary sequence of neurturin revealed a stretch of residues in the heel region of neurturin (RRLRQRRRLRRER) (SEQ. ID. NO 31) which was consistent with the consensus sequences for heparin-binding; specifically the sequences "BBXB" or "BBBXXB" (Hileman et al., (1998) Bioessays. 20(2):156-67), where B is a basic amino acid and X is any residue. Although the identification of this sequence is consistent with heparin binding, it should be noted that the finding of this consensus sequence in the primary structure of a protein does not mean that the sequence is necessarily involved in heparin-binding. Specifically it has been established both that i) proteins which lack these consensus sequences may still bind to heparin (Delacoux et al. (2000) J. Biol. Chem. 275(38):29377-82), and ii), that proteins containing this motif may not bind heparin.

In fact for all proteins, the ability of consecutively arranged stretches of positively charged amino acids to bind to heparin or heparan sulfate is dependent on the 3-dimensional orientation of the basic residues within the context of the entire three dimensional structure of the mature fully folded protein. Moreover, as heparin and heparan sulfates are linear polymers, the positively charged residues in neurturin must not only be present in the primary sequence, but must also be correctly aligned in space. In other words, at least three positively charged side chains must be surface exposed, should be orientated in the correct directions, and be arranged in the correct relative spatial relationship to efficiently dock with the negatively charged residues in heparin and heparan sulfate.

Accordingly for the present studies we used a combination of primary sequence analysis and homology modeling to plan our mutants. Specifically to check if the selected positively charged residues in neurturin also comply with these spatial rules, the 3D structure of neurturin was modeled based on the known crystal structure of GDNF (Eigenbrot and Gerber, (1997) Nat. Struct. Biol. 1997 4(6):435-8). The structure was visualized and the in silico mutagenesis was performed with PyMol software (DeLano Scientific).

The results of this analysis suggest that the interaction domain of neurturin and heparin spans approximately the region bounded by amino acids 51 to 63 of mature neurturin. More specifically the analysis suggests that each of the positively charged amino acids in this region may contribute to the interaction of heparin and heparan sulfate to neurturin. More specifically we conclude based on this analysis that the positively charged amino acids R51, R52, R54, R56, R57, R58, R60, R61, and R63 make, at least to some extent, a contribution to the affinity of neurturin to heparin.

To directly test this hypothesis, a series of mutants were constructed in which varying numbers of the positively charged arginine residues were replaced with alanine residues. The constructs N1, N2 each contained three amino acid changes which were scattered over the surface of the putative interaction domain of neurturin and heparin spanning residues 51 to 63 of the mature human neurturin In the construct N3, the mutations made in the construction of the N1 and N2 mutants were combined, so as to introduce 5 point mutations. In this construct, R63 was not mutated to test the hypothesis that the conservation of a basic amino acid residue in the related genes, ARTN, PSPN and GDNF is functionally significant. Additionally, in a final construct, (N4) the putative heparin binding region of neurturin spanning residues 51 to 62 was replaced with 7 residues from the corresponding region and associated sequence of PSPN as well as 5 unrelated residues (ARLQGQGALVGS) (SEQ. ID. NO. 25). This change resulted in 9 amino acid changes compared to the corresponding sequence of the wild type human neurturin.

As described more fully below, all of these constructs were successfully expressed, exhibited correct folding, and were both active in a functional assay and displayed a reduced affinity to heparin. It is concluded that this region of neurturin spanning amino acids 51 to 63 provide an area of the protein that is readily amenable to protein optimization to produce functionally active mutants of neurturin which exhibit reduced affinity to heparin.

Example 2

Generation of Neurturin Variants

DNA encoding human neurturin, corresponding to accession number BC137399, was purchased from OpenBiosystems. The mature sequence of neurturin (excluding its endogenous signal sequence and pro-sequence) was subcloned into the vector pSJP-2, the vector backbone of which is based on pAAV-MCS (Stratagene) yielding a plasmid (E778) which encodes the IgG signal sequence, (Fjord-Larsen et al., (2005) "Efficient in vivo protection of nigral dopaminergic neurons by lentiviral gene transfer of a modified Neurturin construct." Exp Neurol 195:49-60), followed by the sequence of mature neurturin without pro-sequence. E778 was used as a template for inverse PCR mutagenesis. The primers for the untagged neurturin variant N1 were: F/5'-ag gcg cgg gcc ctg cgg cgg gag cgg gtg cgc-3' (SEQ. ID. NO. 11) and R/5'-g gcg cag tgc tcg cag ccc gag gtc gta gac g-3', (SEQ. ID. NO. 12) for N2: F/5'-ctg cgg gcg gag gcg gtg cgc gcg cag ccc tgc tgc-3' (SEQ. ID. NO. 13) and R/5'-gcg ccg ccg ctg ggc cag tcg tcg cag ccc gag gtc g-3, (SEQ. ID. NO. 14) for N3: F/5'-cgg gcc ctg cgg gcg gag cgg gtg cgc gcg cag ccc-3'(SEQ. ID. NO. 15) and R/5'-cgc ctg ggc cag tgc tcg cag ccc gag gtc gta gac g-3' (SEQ. ID. NO. 16), for N4: F/5'-ggc gcc ctg gtg ggg tcc cgg gtg cgc gcg cag ccc tgc-3' (SEQ. ID. NO. 17), R/5'-ctg acc ctg cag tcg tgc cag ccc gag gtc gta gac gcg c-3' (SEQ. ID. NO. 18). The PCR reactions were preformed with Phusion™ high-fidelity DNA polymerase (Finnzymes). The PCR mixes were digested with DpnI (Fermentas), and the mutated plasmids were purified from agarose gel with QIAquick Gel Extraction Kit (Qiagen), phosphorylated with T4 polynucleotide kinase (Fermentas), ligated with T4 DNA ligase (Fermentas) and transformed into competent DH5α E. coli cells. Plasmid DNA was isolated from single colonies and the mutagenesis result was verified by sequencing of the insert.

A V5-tag (GKPIPNPLLGLDST, SEQ. ID. NO. 19) was added to the N-terminus of all constructs. In order to enhance the cleavage after the signal sequence, two extra amino acid residues (Alanine and Arginine) were introduced between the signal sequence and the V5 tag. In order to enhance the exposure of the tag-epitope, two extra amino acid residues (Serine and Glycine) were introduced between the V5-tag and the mature neurturin sequence. E778, N1, N2, N3 and N4 were used as templates for mutagenesis, and the primers were: F/5'-ctc ctc ggt ctc gat tct acg tcg ggg gcg cgg ttg ggg gcg cgg cct tg-3' (SEQ. ID. NO. 20), R/5'-agg gtt agg gat agg ctt acc ccg cgc cga att cac ccc tgt aga aag aaa ggc-3' (SEQ. ID. NO. 21). The inverse PCR mutagenesis and subsequent cloning steps were done as above. The V5-tagged clones were called E779 (from E778), NV1 (from N1), NV2 (from N2), NV3 (from N3), and NV4 (from N4).

Example 3

Production and Purification of Neurturin Variants

CHO cells were transiently transfected with E436 (GFP), wild-type V5-tagged neurturin or the V5-tagged neurturin variants NV1-NV4. The transfection was done using Turbofect (Fermentas) according to the manufacturer's instructions. After four hours the media containing the transfection reagent was replaced with normal media consisting of DMEM (Sigma), 10% FBS (HyClone), 100 U/ml Penicillin (Gibco) and 100 µg/ml Streptomycin (Gibco). Two days later the media was collected from each plate. In order to pellet floating cells, the media were centrifuged (5 minutes, 16,200×g) before use. The harvested sample was loaded onto a 15% SDS-PAGE and analysed by Western blotting with V5-antibodies (Invitrogen). All of the variants were successfully expressed, and secreted into the media, and ran on SDS-PAGE at the corrected predicted molecular mass (Data not shown).

Example 4

Heparin-Binding Properties of Neurturin Variants

Media (5 ml) from the transiently transfected CHO cells were diluted with 20 ml of 10 mM Hepes, pH 7.2. The HiTrap Heparin HP column (GE Healthcare) was equilibrated with 10 ml of 10 mM Hepes, pH 7.2 and the diluted samples were applied with a syringe according to the manufacturer's instructions. The columns were washed with 5 ml of 0.1 M NaCl in 10 mM Hepes, pH 7.2 before elution with a stepwise (each step 0.5 ml) NaCl-gradient of 0.2 M, 0.3 M, 0.4 M, 0.5 M, 0.6 M, 0.7 M, 0.8 M, 0.9 M, 1.0 M, 1.1 M, 1.2 M and 1.5 M NaCl in 10 mM Hepes, pH 7.2. The column was subsequently regenerated with 5 ml of 2.0 M NaCl according to the manufacturer's instruction, re-equilibrated with 10 ml of 10 mM Hepes buffer pH 7.2 and used for the following sample. The order of analysed samples was $1^{st}$ NV1, $2^{nd}$ NV2, $3^{rd}$ NV3, $4^{th}$ NV4 and $5^{th}$ wild-type neurturin. The wild type was applied as the last sample in order to control the functionality of the column throughout the assay.

Samples (20 µl) from each elution fraction was boiled with Laemmli buffer, loaded onto a 15% SDS-PAGE and analysed by Western blotting with V5-antibodies (Invitrogen). As a control, 20 µl of the original media was loaded onto the first lane of the gel. The assay was performed twice with identical results. The results are shown in Table E1. It should be noted that in the table, the molarity of NaCl indicates the concentration of the solution applied to the column and that the NaCl concentration of the eluted fractions was not determined in this assay. (++) indicates a stronger and (+) indicates a weaker band of neurturin with a molecular weight of around 15 kDa, detected by WB with antibodies to V5. The results show that all four V5-tagged neurturin variants have significantly decreased heparin-binding, compared to wild type neurturin.

TABLE E1

| | 0.2 M | 0.3 M | 0.4 M | 0.5 M | 0.6 M | 0.7 M | 0.8 M | 0.9 M | 1.0 M | 1.1 M | 1.2 M | 1.5 M |
|---|---|---|---|---|---|---|---|---|---|---|---|---|
| NRTN WT | | | | | | | | | | + | ++ | + |
| NRTN NV1 | | | | | | | | + | ++ | | | |
| NRTN NV2 | | | | | ++ | ++ | + | | | | | |
| NRTN NV3 | | | | | ++ | + | | | | | | |
| NRTN NV4 | | + | ++ | ++ | + | | | | | | | |

Specifically the neurturin wild type protein was eluted from the column over a NaCl concentration range of about 1.0 to 1.2 M NaCl. By comparison the neurturin mutant NV1 was eluted from the column over a NaCl concentration range of about 0.9 to 1.0 M NaCl; the neurturin mutant NV2 was eluted from the column over a NaCl concentration range of about 0.6 to 0.8 M NaCl; the neurturin mutant NV3 was eluted from the column over a NaCl concentration range of about 0.6 to 0.7 M NaCl; and the neurturin mutant NV4 was eluted from the column over a NaCl concentration range of about 0.4 to 0.7 M NaCl.

Thus it is concluded that all of the neurturin mutants had a decreased affinity compared to wild type neurturin. Additionally it is concluded that the neurturin mutants NV4 and NV3 exhibited the lowest apparent affinity to heparin.

Example 5

Receptor Phosphorylation Properties of Neurturin Variants

Fibroblasts (MG87-RET) which are stably transfected with the human RET long isoform (Eketjäll et al., 1999, EMBO J., 18:5901) were transiently transfected with rat GFRα1 or human GFRα2. The transfection was done with Turbofect (Fermentas) according to the manufacturer's instructions. After four hours the media containing the transfection reagent was replaced with normal media consisting of DMEM (Sigma), 10% FBS (HyClone), 2 µg/ml Puromycin (Sigma), 100 U/ml Penicillin (Gibco) and 100 µg/ml Streptomycin (Gibco). One day later the cells were starved in DMEM (Sigma) for four hours. After starvation, media from the transiently transfected CHO cells (expressing GFP, wild-type V5-tagged neurturin or V5-tagged variants of neurturin, NV1-NV4) were diluted 1:2 with DMEM (Sigma), and applied for 10 min on the GFRα1 or GFRα2 transfected MG87-RET fibroblasts. Thereafter the fibroblasts were lysed and the lysates were used for immunoprecipitation of RET (antibodies to RET from Santa Cruz Biotechnology Inc). The immunocomplexes were collected with Protein G-Sepharose (GE Healthcare) and analysed on 8% SDS-PAGE and Western blotting. The phosphorylation of RET was detected by antibodies to phosphotyrosine (Upstate Biotechnology. Equal loading was verified by stripping the filter and re-probing it with antibodies to RET (Santa Cruz Biotechnology Inc). The assay was performed twice with identical results.

TABLE E2

| | GFR receptor used for transfection | | | |
|---|---|---|---|---|
| | GFRalpha2 | | GFRalpha1 | |
| | Antibody Used | | | |
| | P-Tyr | RET | P-Tyr | RET |
| GFP | | + | | + |
| NRTN WT | + | + | + | + |
| NRTN NV1 | + | + | + | + |
| NRTN NV2 | + | + | + | + |
| NRTN NV3 | + | + | + | + |
| NRTN NV4 | + | + | + | + |

The results which are summarized in Table E2 show that all of the constructs were able to promote the phosphorylation of RET mediated by the co-receptor GFR alpha1 and GFR alpha2. Accordingly it is concluded that all of these variants produce proteins that are soluble, correctly expressed and secreted from a mammalian expression system, and adopt a functionally active three dimensional structure.

Example 6

Precipitation of Neurturin with GFRalpha2-Fc Fusion Protein

To determine if the neurturin variants could be purified from crude media preparations based on their affinity to GFRα2, media from CHO cells transiently transfected with the V5-tagged NRTN variants were collected, stored at +4° C. and used for pilot precipitation assays. An aliquot of each media (400 µl) was incubated with recombinant human GFRα2-Fc chimera (0.4 µg, R&D Systems), antibodies to the V5-epitope (0.4 µg, Invitrogen) or antibodies to NRTN (0.4 µg, R&D Systems) for 1 h at +4° C. with mixing. Protein G has a strong affinity for antibodies from mouse and goat as well as for the Fc portion of human IgG$_1$ in the recombinant GFRα2-Fc chimera. Therefore Protein G-Sepharose was added to the samples and the incubation was continued for 1 h at +4° C. with mixing. After pelleting, the samples were eluted from the protein G-Sepharose with reducing Laemmli buffer and loaded on SDS-PAGE. For Western blot analysis of the V5-tagged variants of NRTN, an anti-V5 antibody (Invitrogen) was used with samples loaded on SDS-PAGE under reducing conditions. For Western blot analysis of the untagged variants of NRTN, an anti-NRTN antibody (R&D Systems) was used with samples loaded on SDS-page under non-reducing conditions. The sensitivity of the anti-NRTN antibody is significantly lower with samples loaded under reducing conditions.

The results (not shown) demonstrated that all of the neurturin variants can be precipitated with the aid of a commercially available GFRα2 which fused to an antibody constant (Fc) domain, and can be subsequently purified via a protein G-sepharose column. Moreover this purification approach appears to be at least as efficient as immunoprecipitation using the V-5 epitope tag.

Example 7

Neurite Outgrowth Assay

In order to corroborate the results with the RET-phosphorylation assays, media from CHO cells transiently transfected with either GFP or the V5-tagged NRTN variants for two days were collected, stored at +4° C. and used for pilot neurite outgrowth assays. Samples from the media (DMEM, 10% fetal bovine serum, penicillin and streptomycin) were diluted 1:2 with DMEM and horse serum was added to a final concentration of 5%. PC6-3 cells, which are originally subcloned from the parental PC12 cell line, were transiently transfected with GFRα2. One day after transfection the media was replaced with the diluted media from the CHO cells. Media from GFP transfected CHO cells was diluted as above and used on PC6-3 cells as a negative control. NRTN (50 ng/ml, PeproTech) was added to conditioned CHO media (diluted as above) and used on PC6-3 cells as a positive control. The neurites were not counted, but representative fields of the cells were photographed five days after induction. The results (not shown) demonstrated that all of the neurturin variants were also biologically active in this assay.

Example 8

Stability Assays

CHO cells were transiently transfected with the V5-tagged NRTN variants. After two days the media were collected and used (A) undiluted in the presence or absence of 10 mM EDTA or, (B) diluted 1:10 with a 50 mM buffer (Sodium Citrate buffer pH 6.0, Tris buffer pH 6.8, or Tris buffer pH 8.0 Tris buffer pH 8.8, Tris buffer pH 9.5). The undiluted or diluted media (400 µl) were transferred to empty plates, in the absence of cells and incubated for 5 h at 37° C. In the end of the incubation samples of 20 µl were taken and loaded on SDS-PAGE under reducing conditions. Western blot analysis was conducted as described previously and proteins were detected using anti-V5 antibodies. The results shown in Table E3, demonstrate that the wild type and NV1 variant of neurturin disappeared from the media in the absence of cells, both in the presence and absence of EDTA. By comparison mutants NV2, NV3 and NV4 appeared to have enhanced stability under these conditions.

TABLE E3

| Variant | Incubation Conditions | | |
|---|---|---|---|
| | Starting Media | +EDTA 5 hr | No EDTA 5 hr |
| NRTN WT | + | − | − |
| NRTN NV1 | + | − | − |
| NRTN NV2 | ++ | + | + |
| NRTN NV3 | ++ | ++ | ++ |
| NRTN NV4 | ++ | ++ | ++ |

Accordingly this data demonstrates that the enhanced neurturin polypeptides, and in particular the variants NV2, NV3 and NV4 additionally have the unexpected property of enhanced stability compared to wild type neurturin.

Example 9

Immunocytochemical Staining to Normal and Heparan Sulfate Deficient CHO Cells CHO cells were transiently transfected with untagged wild-type NRTN, V5-tagged wild-type NRTN or V5-tagged NV4 NRTN variant. After 2 days samples of media were collected and stored at +4° C. A second set of CHO cells were plated on cover slips. After two days, a portion of these cells were transfected with GFRα2. One day after transfection the media was replaced with the stored media collected from the first set of CHO cells expressing the NRTN variants. The cells were incubated with the media for 10 min and were subsequently rinsed three times for 5 min with PBS before fixing with 3% PFA for 15 min, permeabilzation in 0.2% Triton X-100 for 5 min and blocking in 1% BSA for 30 min. The antibodies to V5 (Invitrogen) were diluted 1:500, and the CY3-conjugated donkey anti-mouse antibodies (Jackson) were diluted 1:400. The assay was repeated as above but using CHO cells deficient in heparan sulfate (psgA 745). In this case, the cells were not permeabilsed and the nuclei were stained with Hoechst (Invitrogen) before the mounting.
The results (not shown) demonstrated that wild type neurturin attaches to the surface of wild type, but not to heparan sulfate deficient CHO cells. By comparison the neurturin variant NV4 fails to bind to either wild type or heparan sulfate deficient CHO cells. Thus it is concluded that, at least with respect to the variant NV4, the loss of the high affinity interaction domain encompassed by amino acids 51 to 62 is sufficient to prevent binding of the enhanced neurturin to the cell surface.

Example 10

Scaled Up Production and Characterization of Enhanced Neurturin Polypeptides Mature fully folded neurturin is characterized by a cysteine knot structure with seven disulfide bridges. Each monomer of the dimeric protein harbors three intramolecular disulfide bridges, and the monomers are linked together by an additional intermolecular disulfide bridge. Previous studies have established that NRTN expression in mammalian Chinese hamster ovary cells (CHO-cells) typically allows the production of proteins with a higher biological activity (in vitro) than *E. coli*-produced NRTN (Hoane et al., (2000) Exp Neurol. 162(1):189-93). This is because mammalian cells have a stringent intracellular quality control for the folding of secreted proteins with disulfide bridges, whereas *E. coli* expression typically requires di-sulfided bonded proteins to be refolded from inclusion bodies.

Accordingly, scaled up production of the enhanced neurturin proteins was completed using CHO cells, using the proprietary QMCF Technology developed at Icosagen Ltd. (See European Patent No. EP1851319). In brief, the QMCF expression vectors for the enhanced neurturin coding sequence carry the hybrid replication origin comprised of enhancerless polyomavirus minimal origin of replication and maintenance element provided by Epstein-Barr Virus Family of Repeats. QMCF Technology has been developed for expression of therapeutic proteins using cells capable of supporting replication and stable maintenance of QMCF multicopy nuclear extrachromosomal expression vectors. The cell lines used for production were modified suspension CHO cells (CHOEBNALT85), which express two additional proteins for providing replication initiation at polyomavirus enhancerless origin and provide for the effective maintenance of the expression vectors. The neurturin variants were expressed without any N-terminal tag, or extra N-terminal amino acid residues. The sequences are shown in Table D2.
Purification Method Media from NRTN-expressing CHO cells (QMCF Technology at Icosagen Ltd) was thawed at room temperature. HITRAP™ Heparin HP columns (1 ml, GE Healthcare) were equilibrated with 10 ml of 10 mM Hepes, pH 7.2 and 1-10 ml of undiluted media was applied with a syringe according to the manufacturer's instructions. The media was collected and run through the column a second time. The columns were washed with 10 ml of 0.2 M NaCl in 10 mM Hepes, pH 7.2. The NRTN enriched samples were eluted with 5×600 µl of 10 mM Hepes pH 7.2, 1.2 M NaCl. Fractions number two and three were collected and concentrated to a final volume of 50-65 µl, according to the manufacturer's instruction in AmiconUltra 0.5 ml 10K concentrators (Millipore). The samples were then diluted 1:10 with 10 mM Hepes pH 7.2 to a final concentration of NaCl around 120 mM. Soluble recombinant GFRα2-Fc chimera (10-200 µg, R&D Systems) was attached to Protein G HP SpinTrap columns (GE Healthcare) in PBS according to the manufacturer's instructions. The 1:10 diluted samples were added to the GFRα2 columns and incubated for at least one hour at +4° C. with mixing. The columns were first washed with 4×400 µl of cold 10 mM Hepes pH 7.2, 1.0 M NaCl and thereafter with 4×400 µl of cold 10 mM Hepes pH 7.2, 0.1

M NaCl. The NRTN samples were eluted with 5×200 µl of pre-warmed (25° C.) 10 mM Hepes pH 7.2, 2.0 M $MgCl_2$. The eluted fractions were immediately diluted (1:2) with 10 mM Hepes pH 7.2, 0.150 M NaCl and concentrated with AMICONULTRA™ 0.5 ml 10K concentrators. The samples were further diluted in the same buffer (1:2) and subsequently concentrated three times to yield a final concentration of around 125 mM $MgCl_2$, and 150 mM NaCl in 10 mM Hepes pH 7.2. Samples of the purified proteins as well as a commercially available batch of neurturin were analyzed using 15% SDS-PAGE, under non reducing conditions, and visualized via Coomassie staining. The results shown in FIG. 1 demonstrate that the purification procedure resulted in the efficient isolation of each of the enhanced neurturins.

N-Terminal Sequencing and Mass Spectrometry Analysis

The N-terminal sequence of the purified NRTN variants was determined by Edman degradation with an applied Biosystems Procise 494A HT Sequencer (Perkin Elmer, Waltham, Mass.), (where cysteine cannot be detected without prior modification). The molecular mass of the dimeric proteins was determined with a MALDI-TOF instrument (Ultraflex TOF/TOF, Bruker), which was exactly calibrated between 5700 and 16900 Da. The results Table E4 showed that the proteins were of the correct mass, and exhibited little or no n-terminal clipping.

TABLE E4

| Variant | Predicted Mass | Experimentally Determined Mass [M + H]+ |
| --- | --- | --- |
| NRTN WT | 23354.6 | 23345.065 |
| NRTN N1 | 22844.0 | 22807.642 |
| NRTN N2 | 22844.0 | 22822.791 |
| NRTN N3 | 22469.654 | 22469.654 |
| NRTN N4 | 22165.2 | 22143.254 |

Example 11

Biacore Analysis of Affinity of Neurturin Variants to Heparin

The affinity of the NRTN variants to heparin was assayed by surface plasmon resonance, using a Biacore T100 instrument and a streptavidin coated Sensor Chip SA (Series S,GE Healthcare). Biotinylated heparin (Sigma) was attached to the chip. To eliminate free biotin in the biotin-heparin preparation, 50 µl of biotin-heparin (20 µg/µl) was diluted 1:10 in 10 mM Hepes pH 7.2, and subsequently concentrated with an Amicon Ultra concentration tube (10K, Millipore) back to 50 µl. By repeated cycles of dilution/concentration a 1,000,000-fold desalting effect was achieved. We assumed that the recovery of the desalted biotin-heparin was 100%, and diluted it to a final concentration of 200 µg/ml in HBS-EP+Buffer (GE Healthcare: 100 mM Hepes pH 7.4, 150 mM NaCl, 3 mM EDTA, 0.05% (v/v) surfactant P20), before loading it on the streptavidin coated chip with a flow rate of 5 µl/min for 10 min. The attachment of biotin-heparin to the chip resulted in an increase of 361 RU on the chip. No ligand was added to the reference chip.

The actual concentration of the NRTN variants was determined by Coomassie staining. The NRTN variants were passed over the heparin-coated chip at five different concentrations (25, 50, 100, 200 and 500 nM). The initiation of the association was significantly delayed when the NRTN variants were diluted in the standard buffer (HBS-EP+). Therefore we increased the NaCl concentration of the buffer to 235 mM. Using the modified buffer we analyzed the interaction between the NRTN variants and heparin with a flow rate of 30 µl/min, an injection time of 240 s, and a dissociation time of 600 s. The chip was regenerated with 1 M NaCl for 30 s between the cycles. The stabilization period was 20 s.

The results showed that wild type neurturin exhibited an apparent affinity to heparin under these conditions of between $2.5 \times 10^{-9}$ M and $3.8 \times 10^{-9}$ M. By comparison, all of the neurturin variants exhibited apparent affinities to heparin which were considerably lower. (Data not shown).

Example 12

Heparin Affinity Chromatography

To characterize the affinity of the NRTN variants to heparin we used a small heparin affinity chromatography column. After loading about 2 µg of each of the purified NRTN variants to the heparin affinity chromatography column in 10 mM Hepes pH 7.2, the samples were eluted with a continuous NaCl gradient (10 mM Hepes with increasing NaCl, to 2 M). The elution of the proteins was monitored by their absorption at 214 nm. The exact salt concentration of the fractions containing the eluted proteins was determined based on the conductivity. The A214 nm detector was located before the conductivity detector (about 20-25 µl). As the flow rate was 50 µl/min, the conductivity corresponding to the A214 absorbance was recorded with a delay of about half a minute.

The results shown in FIG. 2 correspond well with our earlier analysis (shown in Table E1) of the elution characteristics of these proteins from the heparin affinity column. Here the exact salt concentration of the fractions containing the eluted proteins was determined based on the conductivity. The A214 nm detector was located before the conductivity detector (about 20-25 µl). As the flow rate was 50 µl/min, the conductivity corresponding to the A214 absorbance was recorded with a delay of about half a minute. Specifically the neurturin wild type protein was eluted from the column with a peak at a conductivity corresponding to a NaCl concentration of about 1.08 M. By comparison the neurturin mutant N1, although recovered in a lower yield, was eluted from the column with a peak at a conductivity corresponding to a NaCl concentration of about 0.97 M; the neurturin mutant N2 was eluted from the column with a peak at a conductivity corresponding to a NaCl concentration of about 0.56 M; the neurturin mutant N3 was eluted from the column with a peak at a conductivity corresponding to a NaCl concentration of about 0.56 M; and the neurturin mutant N4 was eluted from the column with a peak at a conductivity corresponding to a NaCl concentration of about 0.48 M.

Example 13

Receptor Phosphorylation Properties of the Purified Neurturin Variants

Fibroblasts (MG87-RET) stably expressing the human RET long isoform (Eketjäll et al., 1999, EMBO J., 18:5901) were transiently transfected with rat GFRα1 or human GFRα2 as described previously. Samples containing 100 ng/ml of commercial neurturin, or the purified NRTN variants were added to the cells at 37 C for 10 min Thereafter the fibroblasts were lysed and the lysates were used for immunoprecipitation of RET (antibodies to RET from Santa Cruz Biotechnology Inc). The immunocomplexes were collected with Protein G-Sepharose (GE Healthcare) and analysed on 8% SDS-PAGE and Western blotting. The phosphorylation of RET was detected by antibodies to phosphotyrosine (Upstate Biotechnology) Equal loading was verified by stripping the filter and re-probing it with antibodies to RET (Santa Cruz Biotechnology Inc) The assay was performed twice with identical results.

Figure 3A:
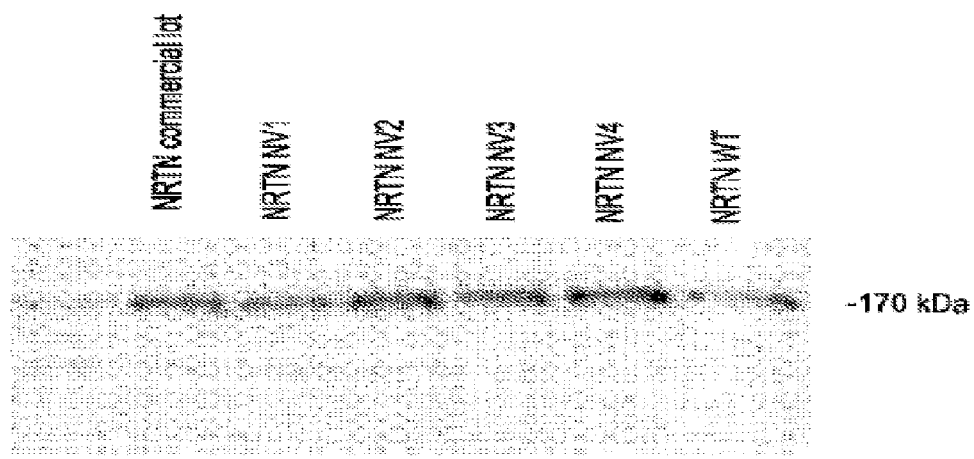
FIG. 3A shows a western blot analysis of a RET-phosphorylation assay. Cells that stably express RET were transiently transfected with GFRα2, and after stimulation with the indicated neurturin variants, the cells were lysed and RET was isolated by immunoprecipitation. The samples were analysed by probing with anti-phosphotyrosine antibodies.
Figure 3B:
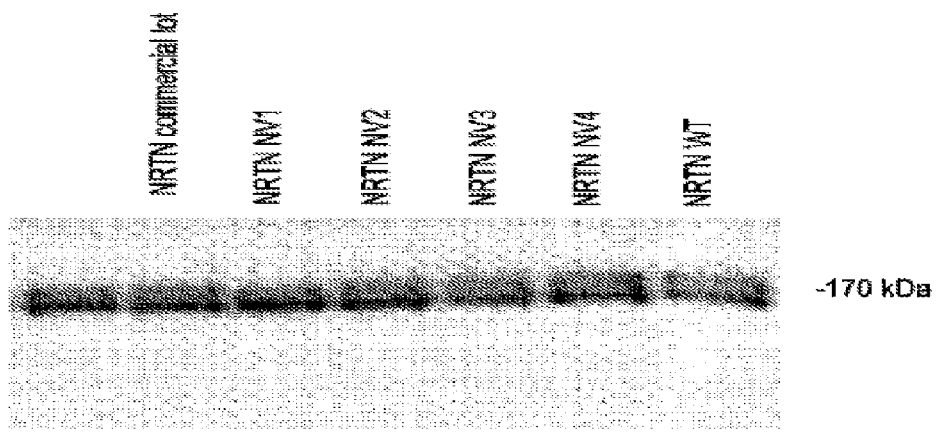
FIG. 3B. To confirm an equal loading, the samples were subsequently re-probed with anti-RET antibodies.

FIG. 3 shows a western blot analysis of a RET-phosphorylation assay. Cells that stably express RET were transiently transfected with GFRα2, and after stimulation with the indicated neurturin variants, the cells were lysed and RET was isolated by immunoprecipitation. The samples were analysed by probing with anti-phosphotyrosine antibodies (A). To confirm an equal loading, the samples were subsequently re-probed with anti-RET antibodies (B). FIG. 4 shows a western blot analysis of a RET-phosphorylation assay. Cells that stably express RET were transiently transfected with GFRα1, and after stimulation with the indicated neurturin variants, the cells were lysed and RET was isolated by immunoprecipitation. The samples were analysed by probing with anti-phosphotyrosine antibodies (A). To confirm an equal loading, the samples were subsequently re-probed with anti-RET antibodies (B). As previously determined with crude preparations of the neurturin variants, the results confirm that all of the enhanced neurturin polypeptides exhibit functional activity.

SEQ ID Number List

| SEQ. ID. NO. | Source | Type | Amino Acid Sequence |
|---|---|---|---|
| 1 | Synthetic | Amino Acid | ARLGARPCGLRELEVRVSELGLGYASDETVLFRYCAGACE AAARVYDLGLRALRQARALRRERVRAQPCCRPTAYEDEVSFLDAHSRYHT VHELSARECACV |
| 2 | Synthetic | Amino Acid | ARLGARPCGLRELEVRVSELGLGYASDETVLFRYCAGACE AAARVYDLGLRRLAQRRRLRAEAVRAQPCCRPTAYEDEVSFLDAHSRYHT VHELSARECACV |
| 3 | Synthetic | Amino Acid | ARLGARPCGLRELEVRVSELGLGYASDETVLFRYCAGACE AAARVYDLGLRALAQARALRAERVRAQPCCRPTAYEDEVSFLDAHSRYHT VHELSARECACV |
| 4 | Synthetic | Amino Acid | ARLGARPCGLRELEVRVSELGLGYASDETVLFRYCAGACE AAARVYDLGLARLQGQGALVGSRVRAQPCCRPTAYEDEVSFLDAHSRYHT VHELSARECACV |
| 5 | Human | Amino Acid | ARLGARPCGLRELEVRVSELGLGYASDETVLFRYCAGACE AAARVYDLGLRRLRQRRRLRRERVRAQPCCRPTAYEDEVSFLDAHSRYHT VHELSARECACV |
| 6 | Synthetic | Nucleic Acid | gcgcggttgggggcgcggccttgcgggctgcgcgagctggaggtgcgcgtgagc gagctgggcctgggctacgcgtccgacgagacggtgctgttccgctactgcgca ggcgcctgcgaggctgccgcgcgcgtctacgacctcgggctgcgagcactgcgc caggcgcgggccctgcggcgggagcgggtgcgcgcgcagccctgctgccgcccg acggcctacgaggacgaggtgtccttcctggacgcgcacagccgctaccacacg gtgcacgagctgtcggcgcgcgagtgcgcctgcgtgtga |
| 7 | Synthetic | Nucleic Acid | gcgcggttgggggcgcggccttgcgggctgcgcgagctggaggtgcgcgtgagc gagctgggcctgggctacgcgtccgacgagacggtgctgttccgctactgcgca ggcgcctgcgaggctgccgcgcgcgtctacgacctcgggctgcgacgactggcc caggcggcgcctgcgggcggaggcggtgcgcgcgcagccctgctgccgcccg acggcctacgaggacgaggtgtccttcctggacgcgcacagccgctaccacacg gtgcacgagctgtcggcgcgcgagtgcgcctgcgtgtga |
| 8 | Synthetic | Nucleic Acid | gcgcggttgggggcgcggccttgcgggctgcgcgagctggaggtgcgcgtgagc gagctgggcctgggctacgcgtccgacgagacggtgctgttccgctactgcgca ggcgcctgcgaggctgccgcgcgcgtctacgacctcgggctgcgagcactggcc caggcgcgggccctgcggcgggagcgggtgcgcgcgcagccctgctgccgcccg acggcctacgaggacgaggtgtccttcctggacgcgcacagccgctaccacacg gtgcacgagctgtcggcgcgcgagtgcgcctgcgtgtga |
| 9 | Synthetic | Nucleic Acid | gcgcggttgggggcgcggccttgcgggctgcgcgagctggaggtgcgcgtgagc gagctgggcctgggctacgcgtccgacgagacggtgctgttccgctactgcgca ggcgcctgcgaggctgccgcgcgcgtctacgacctcgggctggcacgactgcag ggtcagggcgccctggtggggtcccgggtgcgcgcgcagccctgctgccgcccg acggcctacgaggacgaggtgtccttcctggacgcgcacagccgctaccacacg gtgcacgagctgtcggcgcgcgagtgcgcctgcgtgtga |
| 10 | Human | Nucleic Acid | gcgcggttgggggcgcggccttgcgggctgcgcgagctggaggtgcgcgtgagc gagctgggcctgggctacgcgtccgacgagacggtgctgttccgctactgcgca ggcgcctgcgaggctgccgcgcgcgtctacgacctcgggctgcgacgactgcgc caggcggcgcctgcggcgggagcgggtgcgcgcgcagccctgctgccgcccg acggcctacgaggacgaggtgtccttcctggacgcgcacagccgctaccacacg gtgcacgagctgtcggcgcgcgagtgcgcctgcgtgtga |

SEQ ID Number List

| SEQ. ID. NO. | Source | Type | Amino Acid Sequence |
|---|---|---|---|
| 11 | Synthetic | Nucleic Acid | ag gcg cgg gcc ctg cgg cgg gag cgg gtg cgc |
| 12 | Synthetic | Nucleic Acid | g gcg cag tgc tcg cag ccc gag gtc gta gac g |
| 13 | Synthetic | Nucleic Acid | ctg cgg gcg gag gcg gtg cgc gcg cag ccc tgc tgc |
| 14 | Synthetic | Nucleic Acid | gcg ccg ccg ctg ggc cag tcg tcg cag ccc gag gtc g |
| 15 | Synthetic | Nucleic Acid | cgg gcc ctg cgg gcg gag cgg gtg cgc gcg cag ccc |
| 16 | Synthetic | Nucleic Acid | cgc ctg ggc cag tgc tcg cag ccc gag gtc gta gac g |
| 17 | Synthetic | Nucleic Acid | ggc gcc ctg gtg ggg tcc cgg gtg cgc gcg cag ccc tgc |
| 18 | Synthetic | Nucleic Acid | ctg acc ctg cag tcg tgc cag ccc gag gtc gta gac gcg c |
| 19 | Synthetic | Amino Acid | GKPIPNPLLGLDST |
| 20 | Human | Nucleic Acid | ctc ctc ggt ctc gat tct acg tcg ggg gcg cgg ttg ggg gcg cgg cct tg |
| 21 | Human | Nucleic Acid | agg gtt agg gat agg ctt acc ccg cgc cga att cac ccc tgt aga aag aaa ggc |
| 22 | Synthetic | Amino Acid | RALRQARA |
| 23 | Synthetic | Amino Acid | RRLAQRRRLRAEA |
| 24 | Synthetic | Amino Acid | RALAQARALRA |
| 25 | Synthetic | Amino Acid | ARLQGQGALVGS |
| 26 | Human | Amino Acid | MQRWKAAALA SVLCSSVLSI WMCREGLLLS HRLGPALVPL HRLPRTLDAR IARLAQYRAL LQGAPDAMEL RELTPWAGRP PGPRRRAGPR RRRARARLGA RPCGLRELEV RVSELGLGYA SDETVLFRYC AGACEAAARV YDLGLRRLRQ RRRLRRERVR AQPCCRPTAY EDEVSFLDAH SRYHTVHELS ARECACV |
| 27 | Human | Amino Acid | SRLGA RPCGLRELEV RVSELGLGYA SDETVLFRYC AGACEAAARV YDLGLRRLRQ RRRLRRERVR AQPCCRPTAY EDEVSFLDAH SRYHTVHELS ARECACV |
| 28 | Canis familiaris | Amino Acid | MSAGSGGHGS AHGGGGEVGR AARARCDGAG APLRPWTSKC ASEAGWARGG RGGSRNPLCS LCEGEPQTPR CLAVRRGPWG ASGPQTPAGE LPSAQLRAEV NICQWRVPAA AASGDTVSSG CPQAYWAPAT AASGCMGPRW SVQARALAPA APRCCDASVL CLAEMPSSLF GSQLPWLFRE ALWDPRMGVL PLPPPARHPP SSRAAFFTTL CSGFLMNRVD VMTDHYAEVD GNQGPRRAPG AWPSALFAPR MQRWKAAALA SVLCSSVLSI WMCRDGLLLS HRLGPALAPL RRPPRTLDAR IARLAQYRAL LQGAPDAVEL RQLTPWAGGA AGPRRRAGPR RRRARTGSRP CGLRELEVRV SELGLGYASD ETVLFRYCAG ACEAAARVYD LGLRRLRQRR RVRRERVRAQ PCCRPTAYED EVSFLDAHSR YHTVHELSAR ECACV |
| 29 | Bos taurus | Amino Acid | MQRWKAAALA SVLCSSVLSI WMCREGLLLG HRLGPALAPL RRPPRTLDAR IARLAQYRAL LQGAPDAVEL RELTPWAGRS PGPRRRPGPR RRRARARSGT RPCGLRELEV RVSELGLGYA SEETVLFRYC AGACEAAARV YDLGLRRLRQ RRRVRRERVR AQPCCRPTAY EDEVSFLDTH SRYHTVHELS ARECACV |

| SEQ ID Number List | | | |
|---|---|---|---|
| SEQ. ID. NO. | Source | Type | Amino Acid Sequence |
| 30 | *Macaca mulatta* | Amino Acid | MQRWKAAALA SVLCSSVLSI WMCREGLLLS HRLGPALVPL RRLPRTLDTR IARLAQYRAL LQGAPDAVEL RELTPWAGRP PGPRRRAGPR RRRARARSGA RPCGLRELEV RVSELGYASD ETVLFRYCAG ACEAAARVYD LGLRRLRQRR RLRRERVRAQ PCCRPTAYED EVSFLDAHSR YHTVHELSAR ECACV |
| 31 | Human | Amino acid | RRLRQRRRLRRER |

What is claimed is:

1. A method of treating cellular degeneration or insufficiency comprising administering to a patient in need of such treatment a therapeutically effective amount of a neurturin polypeptide comprising the amino acid sequence shown in SEQ ID NO: 4;

wherein the neurturin polypeptide has a decreased affinity to heparin compared to the mature wild type neurturin (SEQ ID NO: 5).

2. The method of claim 1, wherein the patient has a disease or disorder selected from the group consisting of peripheral neuropathy, amyotrophic lateral sclerosis, Alzheimer's disease, Parkinson's disease, Huntington's disease, ischemic stroke, acute brain injury, acute spinal cord injury, neuropathic pain, diabetes, erectile dysfunction, hair loss, Hirschsprung's disease nervous systems tumors, multiple sclerosis, hearing loss, retinopathy and infection.

3. The method of claim 1 or 2, wherein the neurturin polypeptide is administered by systemic administration.

4. The method of claim 1 or 2, wherein the neurturin polypeptide is administered by intrathecal administration.

5. The method of claim 1 or 2, wherein the neurturin polypeptide is administered by intranasal administration.

6. The method of claim 1 or 2, wherein the neurturin polypeptide is administered by intraparenchymal administration.

* * * * *

SEQUENCE LISTING

<160> NUMBER OF SEQ ID NOS: 31

<210> SEQ ID NO 1
<211> LENGTH: 102
<212> TYPE: PRT
<213> ORGANISM: ARTIFICIAL SEQUENCE
<220> FEATURE:
<223> OTHER INFORMATION: Synthesized

<400> SEQUENCE: 1

```
Ala Arg Leu Gly Ala Arg Pro Cys Gly Leu Arg Glu Leu Glu Val Arg
 1               5                  10                  15

Val Ser Glu Leu Gly Leu Gly Tyr Ala Ser Asp Glu Thr Val Leu Phe
            20                  25                  30

Arg Tyr Cys Ala Gly Ala Cys Glu Ala Ala Ala Arg Val Tyr Asp Leu
        35                  40                  45

Gly Leu Arg Ala Leu Arg Gln Ala Arg Ala Leu Arg Arg Glu Arg Val
    50                  55                  60

Arg Ala Gln Pro Cys Cys Arg Pro Thr Ala Tyr Glu Asp Glu Val Ser
65                  70                  75                  80

Phe Leu Asp Ala His Ser Arg Tyr His Thr Val His Glu Leu Ser Ala
                85                  90                  95

Arg Glu Cys Ala Cys Val
            100
```

<210> SEQ ID NO 2
<211> LENGTH: 102
<212> TYPE: PRT
<213> ORGANISM: ARTIFICIAL SEQUENCE
<220> FEATURE:
<223> OTHER INFORMATION: Synthesized

<400> SEQUENCE: 2

```
Ala Arg Leu Gly Ala Arg Pro Cys Gly Leu Arg Glu Leu Glu Val Arg
 1               5                  10                  15

Val Ser Glu Leu Gly Leu Gly Tyr Ala Ser Asp Glu Thr Val Leu Phe
            20                  25                  30

Arg Tyr Cys Ala Gly Ala Cys Glu Ala Ala Ala Arg Val Tyr Asp Leu
        35                  40                  45

Gly Leu Arg Arg Leu Ala Gln Arg Arg Arg Leu Arg Ala Glu Ala Val
    50                  55                  60

Arg Ala Gln Pro Cys Cys Arg Pro Thr Ala Tyr Glu Asp Glu Val Ser
65                  70                  75                  80

Phe Leu Asp Ala His Ser Arg Tyr His Thr Val His Glu Leu Ser Ala
```

```
                        85                  90                  95

Arg Glu Cys Ala Cys Val
            100

<210> SEQ ID NO 3
<211> LENGTH: 102
<212> TYPE: PRT
<213> ORGANISM: ARTIFICIAL SEQUENCE
<220> FEATURE:
<223> OTHER INFORMATION: Synthesized

<400> SEQUENCE: 3

Ala Arg Leu Gly Ala Arg Pro Cys Gly Leu Arg Glu Leu Glu Val Arg
1               5                   10                  15

Val Ser Glu Leu Gly Leu Gly Tyr Ala Ser Asp Glu Thr Val Leu Phe
            20                  25                  30

Arg Tyr Cys Ala Gly Ala Cys Glu Ala Ala Arg Val Tyr Asp Leu
        35                  40                  45

Gly Leu Arg Ala Leu Ala Gln Ala Arg Ala Leu Arg Ala Glu Arg Val
    50                  55                  60

Arg Ala Gln Pro Cys Cys Arg Pro Thr Ala Tyr Glu Asp Glu Val Ser
65                  70                  75                  80

Phe Leu Asp Ala His Ser Arg Tyr His Thr Val His Glu Leu Ser Ala
                85                  90                  95

Arg Glu Cys Ala Cys Val
            100

<210> SEQ ID NO 4
<211> LENGTH: 102
<212> TYPE: PRT
<213> ORGANISM: ARTIFICIAL SEQUENCE
<220> FEATURE:
<223> OTHER INFORMATION: Synthesized

<400> SEQUENCE: 4

Ala Arg Leu Gly Ala Arg Pro Cys Gly Leu Arg Glu Leu Glu Val Arg
1               5                   10                  15

Val Ser Glu Leu Gly Leu Gly Tyr Ala Ser Asp Glu Thr Val Leu Phe
            20                  25                  30

Arg Tyr Cys Ala Gly Ala Cys Glu Ala Ala Arg Val Tyr Asp Leu
        35                  40                  45

Gly Leu Ala Arg Leu Gln Gly Gln Ala Leu Val Gly Ser Arg Val
    50                  55                  60

Arg Ala Gln Pro Cys Cys Arg Pro Thr Ala Tyr Glu Asp Glu Val Ser
65                  70                  75                  80

Phe Leu Asp Ala His Ser Arg Tyr His Thr Val His Glu Leu Ser Ala
                85                  90                  95

Arg Glu Cys Ala Cys Val
            100

<210> SEQ ID NO 5
<211> LENGTH: 102
<212> TYPE: PRT
<213> ORGANISM: HOMO SAPIENS

<400> SEQUENCE: 5

Ala Arg Leu Gly Ala Arg Pro Cys Gly Leu Arg Glu Leu Glu Val Arg
1               5                   10                  15

Val Ser Glu Leu Gly Leu Gly Tyr Ala Ser Asp Glu Thr Val Leu Phe
```

```
                 20                  25                  30
Arg Tyr Cys Ala Gly Ala Cys Glu Ala Ala Arg Val Tyr Asp Leu
             35                  40                  45

Gly Leu Arg Leu Arg Gln Arg Arg Leu Arg Arg Glu Arg Val
         50                  55                  60

Arg Ala Gln Pro Cys Cys Arg Pro Thr Ala Tyr Glu Asp Glu Val Ser
65                  70                  75                  80

Phe Leu Asp Ala His Ser Arg Tyr His Thr Val His Glu Leu Ser Ala
                 85                  90                  95

Arg Glu Cys Ala Cys Val
             100

<210> SEQ ID NO 6
<211> LENGTH: 309
<212> TYPE: DNA
<213> ORGANISM: ARTIFICIAL SEQUENCE
<220> FEATURE:
<223> OTHER INFORMATION: Synthesized

<400> SEQUENCE: 6
gcgcggttgg gggcgcggcc ttgcgggctg cgcgagctgg aggtgcgcgt gagcgagctg      60
ggcctgggct acgcgtccga cgagacggtg ctgttccgct actgcgcagg cgcctgcgag     120
gctgccgcgc gcgtctacga cctcgggctg cgagcactgc gccaggcgcg ggccctgcgg     180
cgggagcggg tgcgcgcgca gccctgctgc cgcccgacgg cctacgagga cgaggtgtcc     240
ttcctggacg cgcacagccg ctaccacacg gtgcacgagc tgtcggcgcg cgagtgcgcc     300
tgcgtgtga                                                             309

<210> SEQ ID NO 7
<211> LENGTH: 309
<212> TYPE: DNA
<213> ORGANISM: ARTIFICIAL SEQUENCE
<220> FEATURE:
<223> OTHER INFORMATION: Synthesized

<400> SEQUENCE: 7
gcgcggttgg gggcgcggcc ttgcgggctg cgcgagctgg aggtgcgcgt gagcgagctg      60
ggcctgggct acgcgtccga cgagacggtg ctgttccgct actgcgcagg cgcctgcgag     120
gctgccgcgc gcgtctacga cctcgggctg cgacgactgg cccagcggcg cgcgcctgcgg    180 gcggaggcgg tgcgcgcgca gccctgctgc cgcccgacgg cctacgagga cgaggtgtcc     240
ttcctggacg cgcacagccg ctaccacacg gtgcacgagc tgtcggcgcg cgagtgcgcc     300
tgcgtgtga                                                             309

<210> SEQ ID NO 8
<211> LENGTH: 309
<212> TYPE: DNA
<213> ORGANISM: ARTIFICIAL SEQUENCE
<220> FEATURE:
<223> OTHER INFORMATION: Synthesized

<400> SEQUENCE: 8
gcgcggttgg gggcgcggcc ttgcgggctg cgcgagctgg aggtgcgcgt gagcgagctg      60
ggcctgggct acgcgtccga cgagacggtg ctgttccgct actgcgcagg cgcctgcgag     120
gctgccgcgc gcgtctacga cctcgggctg cgagcactgg cccagcggcg ggccctgcgg     180
gcggagcggg tgcgcgcgca gccctgctgc cgcccgacgg cctacgagga cgaggtgtcc     240
```

```
ttcctggacg cgcacagccg ctaccacacg gtgcacgagc tgtcggcgcg cgagtgcgcc    300
tgcgtgtga                                                            309
```

<210> SEQ ID NO 9
<211> LENGTH: 309
<212> TYPE: DNA
<213> ORGANISM: ARTIFICIAL SEQUENCE
<220> FEATURE:
<223> OTHER INFORMATION: Synthesized

<400> SEQUENCE: 9

```
gcgcggttgg gggcgcggcc ttgcgggctg cgcgagctgg aggtgcgcgt gagcgagctg     60
ggcctgggct acgcgtccga cgagacggtg ctgttccgct actgcgcagg cgcctgcgag    120
gctgccgcgc gcgtctacga cctcgggctg cacgactgc agggtcaggg cgccctggtg     180
gggtcccggg tgcgcgcgca gccctgctgc cgcccgacgg cctacgagga cgaggtgtcc    240
ttcctggacg cgcacagccg ctaccacacg gtgcacgagc tgtcggcgcg cgagtgcgcc    300
tgcgtgtga                                                            309
```

<210> SEQ ID NO 10
<211> LENGTH: 309
<212> TYPE: DNA
<213> ORGANISM: HOMO SAPIENS

<400> SEQUENCE: 10

```
gcgcggttgg gggcgcggcc ttgcgggctg cgcgagctgg aggtgcgcgt gagcgagctg     60
ggcctgggct acgcgtccga cgagacggtg ctgttccgct actgcgcagg cgcctgcgag    120
gctgccgcgc gcgtctacga cctcgggctg cgacgactgc gccagcggcg cgcctgcgg    180 cgggagcggg tgcgcgcgca gccctgctgc cgcccgacgg cctacgagga cgaggtgtcc    240
ttcctggacg cgcacagccg ctaccacacg gtgcacgagc tgtcggcgcg cgagtgcgcc    300
tgcgtgtga                                                            309
```

<210> SEQ ID NO 11
<211> LENGTH: 32
<212> TYPE: DNA
<213> ORGANISM: ARTIFICIAL SEQUENCE
<220> FEATURE:
<223> OTHER INFORMATION: Synthesized

<400> SEQUENCE: 11

```
aggcgcgggc cctgcggcgg gagcgggtgc gc                                   32
```

<210> SEQ ID NO 12
<211> LENGTH: 32
<212> TYPE: DNA
<213> ORGANISM: ARTIFICIAL SEQUENCE
<220> FEATURE:
<223> OTHER INFORMATION: Synthesized

<400> SEQUENCE: 12

```
ggcgcagtgc tcgcagcccg aggtcgtaga cg                                   32
```

<210> SEQ ID NO 13
<211> LENGTH: 36
<212> TYPE: DNA
<213> ORGANISM: ARTIFICIAL SEQUENCE
<220> FEATURE:
<223> OTHER INFORMATION: Synthesized

<400> SEQUENCE: 13
ctgcgggcgg aggcggtgcg cgcgcagccc tgctgc        36

<210> SEQ ID NO 14
<211> LENGTH: 37
<212> TYPE: DNA
<213> ORGANISM: ARTIFICIAL SEQUENCE
<220> FEATURE:
<223> OTHER INFORMATION: Synthesized

<400> SEQUENCE: 14
gcgccgccgc tgggccagtc gtcgcagccc gaggtcg        37

<210> SEQ ID NO 15
<211> LENGTH: 36
<212> TYPE: DNA
<213> ORGANISM: ARTIFICIAL SEQUENCE
<220> FEATURE:
<223> OTHER INFORMATION: Synthesized

<400> SEQUENCE: 15
cgggccctgc gggcggagcg ggtgcgcgcg cagccc        36

<210> SEQ ID NO 16
<211> LENGTH: 37
<212> TYPE: DNA
<213> ORGANISM: ARTIFICIAL SEQUENCE
<220> FEATURE:
<223> OTHER INFORMATION: Synthesized

<400> SEQUENCE: 16
cgcctgggcc agtgctcgca gcccgaggtc gtagacg        37

<210> SEQ ID NO 17
<211> LENGTH: 39
<212> TYPE: DNA
<213> ORGANISM: ARTIFICIAL SEQUENCE
<220> FEATURE:
<223> OTHER INFORMATION: Synthesized

<400> SEQUENCE: 17
ggcgccctgg tggggtcccg ggtgcgcgcg cagccctgc      39

<210> SEQ ID NO 18
<211> LENGTH: 40
<212> TYPE: DNA
<213> ORGANISM: ARTIFICIAL SEQUENCE
<220> FEATURE:
<223> OTHER INFORMATION: Synthesized

<400> SEQUENCE: 18
ctgaccctgc agtcgtgcca gcccgaggtc gtagacgcgc     40

<210> SEQ ID NO 19
<211> LENGTH: 14
<212> TYPE: PRT
<213> ORGANISM: ARTIFICIAL SEQUENCE
<220> FEATURE:
<223> OTHER INFORMATION: Synthesized

<400> SEQUENCE: 19

Gly Lys Pro Ile Pro Asn Pro Leu Leu Gly Leu Asp Ser Thr
1               5                   10

<210> SEQ ID NO 20
<211> LENGTH: 50

<212> TYPE: DNA
<213> ORGANISM: HOMO SAPIENS

<400> SEQUENCE: 20
ctcctcggtc tcgattctac gtcgggggcg cggttggggg cgcggccttg        50

<210> SEQ ID NO 21
<211> LENGTH: 54
<212> TYPE: DNA
<213> ORGANISM: HOMO SAPIENS

<400> SEQUENCE: 21
agggttaggg ataggcttac cccgcgccga attcacccct gtagaaagaa aggc    54

<210> SEQ ID NO 22
<211> LENGTH: 8
<212> TYPE: PRT
<213> ORGANISM: ARTIFICIAL SEQUENCE
<220> FEATURE:
<223> OTHER INFORMATION: Synthesized

<400> SEQUENCE: 22

Arg Ala Leu Arg Gln Ala Arg Ala
1               5

<210> SEQ ID NO 23
<211> LENGTH: 13
<212> TYPE: PRT
<213> ORGANISM: ARTIFICIAL SEQUENCE
<220> FEATURE:
<223> OTHER INFORMATION: Synthesized

<400> SEQUENCE: 23

Arg Arg Leu Ala Gln Arg Arg Arg Leu Arg Ala Glu Ala
1               5                   10

<210> SEQ ID NO 24
<211> LENGTH: 11
<212> TYPE: PRT
<213> ORGANISM: ARTIFICIAL SEQUENCE
<220> FEATURE:
<223> OTHER INFORMATION: Synthesized

<400> SEQUENCE: 24

Arg Ala Leu Ala Gln Ala Arg Ala Leu Arg Ala
1               5                   10

<210> SEQ ID NO 25
<211> LENGTH: 12
<212> TYPE: PRT
<213> ORGANISM: ARTIFICIAL SEQUENCE
<220> FEATURE:
<223> OTHER INFORMATION: Synthesized

<400> SEQUENCE: 25

Ala Arg Leu Gln Gly Gln Gly Ala Leu Val Gly Ser
1               5                   10

<210> SEQ ID NO 26
<211> LENGTH: 197
<212> TYPE: PRT
<213> ORGANISM: HOMO SAPIENS

<400> SEQUENCE: 26

Met Gln Arg Trp Lys Ala Ala Ala Leu Ala Ser Val Leu Cys Ser Ser
1               5                   10                  15

```
Val Leu Ser Ile Trp Met Cys Arg Glu Gly Leu Leu Leu Ser His Arg
         20                  25                  30

Leu Gly Pro Ala Leu Val Pro Leu His Arg Leu Pro Arg Thr Leu Asp
             35                  40                  45

Ala Arg Ile Ala Arg Leu Ala Gln Tyr Arg Ala Leu Leu Gln Gly Ala
 50                  55                  60

Pro Asp Ala Met Glu Leu Arg Glu Leu Thr Pro Trp Ala Gly Arg Pro
 65                  70                  75                  80

Pro Gly Pro Arg Arg Arg Ala Gly Pro Arg Arg Arg Ala Arg Ala
                 85                  90                  95

Arg Leu Gly Ala Arg Pro Cys Gly Leu Arg Glu Leu Glu Val Arg Val
                100                 105                 110

Ser Glu Leu Gly Leu Gly Tyr Ala Ser Asp Glu Thr Val Leu Phe Arg
            115                 120                 125

Tyr Cys Ala Gly Ala Cys Glu Ala Ala Arg Val Tyr Asp Leu Gly
 130                 135                 140

Leu Arg Arg Leu Arg Gln Arg Arg Leu Arg Arg Glu Arg Val Arg
145                 150                 155                 160

Ala Gln Pro Cys Cys Arg Pro Thr Ala Tyr Glu Asp Glu Val Ser Phe
                165                 170                 175

Leu Asp Ala His Ser Arg Tyr His Thr Val His Glu Leu Ser Ala Arg
            180                 185                 190

Glu Cys Ala Cys Val
            195

<210> SEQ ID NO 27
<211> LENGTH: 102
<212> TYPE: PRT
<213> ORGANISM: HOMO SAPIENS

<400> SEQUENCE: 27

Ser Arg Leu Gly Ala Arg Pro Cys Gly Leu Arg Glu Leu Glu Val Arg
 1               5                  10                  15

Val Ser Glu Leu Gly Leu Gly Tyr Ala Ser Asp Glu Thr Val Leu Phe
             20                  25                  30

Arg Tyr Cys Ala Gly Ala Cys Glu Ala Ala Arg Val Tyr Asp Leu
                 35                  40                  45

Gly Leu Arg Arg Leu Arg Gln Arg Arg Leu Arg Arg Glu Arg Val
             50                  55                  60

Arg Ala Gln Pro Cys Cys Arg Pro Thr Ala Tyr Glu Asp Glu Val Ser
 65                  70                  75                  80

Phe Leu Asp Ala His Ser Arg Tyr His Thr Val His Glu Leu Ser Ala
                 85                  90                  95

Arg Glu Cys Ala Cys Val
            100

<210> SEQ ID NO 28
<211> LENGTH: 445
<212> TYPE: PRT
<213> ORGANISM: CANIS FAMILIARIS

<400> SEQUENCE: 28

Met Ser Ala Gly Ser Gly Gly His Gly Ser Ala His Gly Gly Gly
 1               5                  10                  15

Glu Val Gly Arg Ala Ala Arg Ala Arg Cys Asp Gly Ala Gly Ala Pro
             20                  25                  30
```

-continued

```
Leu Arg Pro Trp Thr Ser Lys Cys Ala Ser Glu Ala Gly Trp Ala Arg
         35                  40                  45
Gly Gly Arg Gly Gly Ser Arg Asn Pro Leu Cys Ser Leu Cys Glu Gly
 50                  55                  60
Glu Pro Gln Thr Pro Arg Cys Leu Ala Val Arg Arg Gly Pro Trp Gly
 65                  70                  75                  80
Ala Ser Gly Pro Gln Thr Pro Ala Gly Glu Leu Pro Ser Ala Gln Leu
                 85                  90                  95
Arg Ala Glu Val Asn Ile Cys Gln Trp Arg Val Pro Ala Ala Ala Ala
                100                 105                 110
Ser Gly Asp Thr Val Ser Gly Cys Pro Gln Ala Tyr Trp Ala Pro
             115                 120                 125
Ala Thr Ala Ala Ser Gly Cys Met Gly Pro Arg Trp Ser Val Gln Ala
             130                 135                 140
Arg Ala Leu Ala Pro Ala Ala Pro Arg Cys Cys Asp Ala Ser Val Leu
145                 150                 155                 160
Cys Leu Ala Glu Met Pro Ser Ser Leu Phe Gly Ser Gln Leu Pro Trp
                 165                 170                 175
Leu Phe Arg Glu Ala Leu Trp Asp Pro Arg Met Gly Val Leu Pro Leu
             180                 185                 190
Pro Pro Pro Ala Arg His Pro Pro Ser Ser Arg Ala Ala Phe Phe Thr
             195                 200                 205
Thr Leu Cys Ser Gly Phe Leu Met Asn Arg Val Asp Val Met Thr Asp
210                 215                 220
His Tyr Ala Glu Val Asp Gly Asn Gln Gly Pro Arg Arg Ala Pro Gly
225                 230                 235                 240
Ala Trp Pro Ser Ala Leu Phe Ala Pro Arg Met Gln Arg Trp Lys Ala
                 245                 250                 255
Ala Ala Leu Ala Ser Val Leu Cys Ser Ser Val Leu Ser Ile Trp Met
             260                 265                 270
Cys Arg Asp Gly Leu Leu Leu Ser His Arg Leu Gly Pro Ala Leu Ala
             275                 280                 285
Pro Leu Arg Arg Pro Pro Arg Thr Leu Asp Ala Arg Ile Ala Arg Leu
             290                 295                 300
Ala Gln Tyr Arg Ala Leu Leu Gln Gly Ala Pro Asp Ala Val Glu Leu
305                 310                 315                 320
Arg Gln Leu Thr Pro Trp Ala Gly Gly Ala Gly Pro Arg Arg
                 325                 330                 335
Ala Gly Pro Arg Arg Arg Ala Arg Thr Gly Ser Arg Pro Cys Gly
             340                 345                 350
Leu Arg Glu Leu Glu Val Arg Val Ser Glu Leu Gly Leu Gly Tyr Ala
             355                 360                 365
Ser Asp Glu Thr Val Leu Phe Arg Tyr Cys Ala Gly Ala Cys Glu Ala
             370                 375                 380
Ala Ala Arg Val Tyr Asp Leu Gly Leu Arg Arg Leu Arg Gln Arg Arg
385                 390                 395                 400
Arg Val Arg Arg Glu Arg Val Arg Ala Gln Pro Cys Cys Arg Pro Thr
                 405                 410                 415
Ala Tyr Glu Asp Glu Val Ser Phe Leu Asp Ala His Ser Arg Tyr His
             420                 425                 430
Thr Val His Glu Leu Ser Ala Arg Glu Cys Ala Cys Val
             435                 440                 445
```

<210> SEQ ID NO 29
<211> LENGTH: 197
<212> TYPE: PRT
<213> ORGANISM: BOS TAURUS

<400> SEQUENCE: 29

Met Gln Arg Trp Lys Ala Ala Leu Ala Ser Val Leu Cys Ser Ser
1               5                   10                  15

Val Leu Ser Ile Trp Met Cys Arg Glu Gly Leu Leu Gly His Arg
            20                  25                  30

Leu Gly Pro Ala Leu Ala Pro Leu Arg Arg Pro Pro Arg Thr Leu Asp
        35                  40                  45

Ala Arg Ile Ala Arg Leu Ala Gln Tyr Arg Ala Leu Leu Gln Gly Ala
    50                  55                  60

Pro Asp Ala Val Glu Leu Arg Glu Leu Thr Pro Trp Ala Gly Arg Ser
65                  70                  75                  80

Pro Gly Pro Arg Arg Pro Gly Pro Arg Arg Arg Ala Arg Ala
            85                  90                  95

Arg Ser Gly Thr Arg Pro Cys Gly Leu Arg Glu Leu Glu Val Arg Val
                100                 105                 110

Ser Glu Leu Gly Leu Gly Tyr Ala Ser Glu Glu Thr Val Leu Phe Arg
            115                 120                 125

Tyr Cys Ala Gly Ala Cys Glu Ala Ala Ala Arg Val Tyr Asp Leu Gly
        130                 135                 140

Leu Arg Arg Leu Arg Gln Arg Arg Val Arg Arg Glu Arg Val Arg
145                 150                 155                 160

Ala Gln Pro Cys Cys Arg Pro Thr Ala Tyr Glu Asp Glu Val Ser Phe
                165                 170                 175

Leu Asp Thr His Ser Arg Tyr His Thr Val His Glu Leu Ser Ala Arg
            180                 185                 190

Glu Cys Ala Cys Val
        195

<210> SEQ ID NO 30
<211> LENGTH: 195
<212> TYPE: PRT
<213> ORGANISM: MACACA MULATTA

<400> SEQUENCE: 30

Met Gln Arg Trp Lys Ala Ala Ala Leu Ala Ser Val Leu Cys Ser Ser
1               5                   10                  15

Val Leu Ser Ile Trp Met Cys Arg Glu Gly Leu Leu Leu Ser His Arg
            20                  25                  30

Leu Gly Pro Ala Leu Val Pro Leu Arg Arg Leu Pro Arg Thr Leu Asp
        35                  40                  45

Thr Arg Ile Ala Arg Leu Ala Gln Tyr Arg Ala Leu Leu Gln Gly Ala
    50                  55                  60

Pro Asp Ala Val Glu Leu Arg Glu Leu Thr Pro Trp Ala Gly Arg Pro
65                  70                  75                  80

Pro Gly Pro Arg Arg Arg Ala Gly Pro Arg Arg Arg Ala Arg Ala
            85                  90                  95

Arg Ser Gly Ala Arg Pro Cys Gly Leu Arg Glu Leu Glu Val Arg Val
                100                 105                 110

Ser Glu Leu Gly Leu Gly Tyr Ala Ser Asp Glu Thr Val Leu Phe Arg Tyr Cys
            115                 120                 125

-continued

```
Ala Gly Ala Cys Glu Ala Ala Ala Arg Val Tyr Asp Leu Gly Leu Arg
    130                 135                 140
Arg Leu Arg Gln Arg Arg Arg Leu Arg Arg Glu Arg Val Arg Ala Gln
145                 150                 155                 160
Pro Cys Cys Arg Pro Thr Ala Tyr Glu Asp Glu Val Ser Phe Leu Asp
                165                 170                 175
Ala His Ser Arg Tyr His Thr Val His Glu Leu Ser Ala Arg Glu Cys
            180                 185                 190
Ala Cys Val
        195

<210> SEQ ID NO 31
<211> LENGTH: 13
<212> TYPE: PRT
<213> ORGANISM: HOMO SAPIENS

<400> SEQUENCE: 31

Arg Arg Leu Arg Gln Arg Arg Arg Leu Arg Arg Glu Arg
1               5                   10
```